(12) United States Patent
Yager et al.

(10) Patent No.: US 6,984,652 B2
(45) Date of Patent: Jan. 10, 2006

(54) GYRASE INHIBITORS

(75) Inventors: Kraig Yager, Oceanside, CA (US); Shaosong Chu, Encinitas, CA (US); Krzysztof Appelt, Rancho Santa Fe, CA (US); Xiaoming Li, San Diego, CA (US)

(73) Assignee: Warner-Lambert Company LLC, Ann Arbor, MI (US)

( * ) Notice: Subject to any disclaimer, the term of this patent is extended or adjusted under 35 U.S.C. 154(b) by 41 days.

(21) Appl. No.: 10/848,474

(22) Filed: May 17, 2004

(65) Prior Publication Data

US 2005/0054697 A1 Mar. 10, 2005

Related U.S. Application Data

(60) Provisional application No. 60/500,416, filed on Sep. 5, 2003, provisional application No. 60/523,436, filed on Nov. 19, 2003, and provisional application No. 60/565,886, filed on Apr. 27, 2004.

(51) Int. Cl.
 A61K 31/427 (2006.01)
 C07D 417/04 (2006.01)
 C07D 401/14 (2006.01)

(52) U.S. Cl. .................. 514/365; 514/316; 514/338; 514/318; 514/253.01; 514/255.01; 514/237.5; 514/238.8; 514/235.5; 514/236.8; 514/269; 514/211.08; 540/575; 544/369; 544/133; 544/333; 544/124; 544/364; 546/270.4; 546/193; 546/187; 548/181

(58) Field of Classification Search .............. 548/181; 546/270.4, 193, 187; 544/369, 133, 333, 544/124, 364; 540/575; 514/365, 316, 338, 514/318, 253.01, 255.01, 237.5, 238.8, 235.5, 514/236.8, 269, 211.08
See application file for complete search history.

(56) References Cited

U.S. PATENT DOCUMENTS

| | | | |
|---|---|---|---|
| 3,995,044 A | 11/1976 | Kabbe et al. | |
| 4,909,827 A | 3/1990 | Gehring et al. | |
| 5,140,034 A | 8/1992 | Baker et al. | |
| 5,174,808 A | 12/1992 | Wroblowsky et al. | |
| 5,208,248 A | 5/1993 | Baker et al. | |
| 5,569,669 A | 10/1996 | Guillaumet et al. | |
| 6,077,954 A | 6/2000 | Cook et al. | |
| 6,166,027 A | 12/2000 | Straub et al. | |
| 6,391,872 B1 | 5/2002 | Marfat | |
| 6,451,805 B1 | 9/2002 | Straub et al. | |
| 6,455,525 B1 | 9/2002 | Singh et al. | |
| 6,555,539 B2 | 4/2003 | Reich et al. | |
| 6,608,087 B1 | 8/2003 | Badia et al. | |
| 6,716,978 B2 | 4/2004 | Marfat | |
| 2002/0058687 A1 | 5/2002 | Marfat | |
| 2002/0099208 A1 | 7/2002 | Yu et al. | |
| 2003/0119868 A1 | 6/2003 | Badia et al. | |
| 2003/0171403 A1 | 9/2003 | Garthwaite et al. | |
| 2003/0187026 A1 | 10/2003 | Li et al. | |
| 2003/0199511 A1 | 10/2003 | Li et al. | |
| 2004/0087642 A1 | 5/2004 | Zeldis et al. | |
| 2004/0092568 A1 | 5/2004 | Zeldis | |
| 2004/0110815 A1 | 6/2004 | Cournoyer et al. | |

FOREIGN PATENT DOCUMENTS

| | | |
|---|---|---|
| EP | 1040829 A2 | 10/2000 |
| EP | 1346982 | 9/2003 |
| EP | 01380576 A1 | 1/2004 |
| JP | 02007066 | 1/1990 |
| JP | 03206042 | 9/1991 |
| JP | 2003231687 | 8/2003 |
| WO | WO 92/12149 | 7/1992 |
| WO | WO 93/02677 | 2/1993 |
| WO | WO99/23076 | 5/1999 |
| WO | WO99/23077 | 5/1999 |
| WO | WO01/57024 A1 | 8/2001 |
| WO | WO03/024397 A2 | 3/2003 |
| WO | WO03/035625 A1 | 5/2003 |
| WO | WO 2003/051366 | 6/2003 |
| WO | WO03/068754 A1 | 8/2003 |
| WO | WO 2003/101968 | 12/2003 |
| WO | WO2004/060318 A2 | 7/2004 |
| WO | WO2004/087699 A2 | 10/2004 |
| WO | WO2004/094388 A2 | 11/2004 |

OTHER PUBLICATIONS

Shafiee A. et al., "Syntheses, Antibacterial and Antifungal Activities of Substituted–Thiazolo–1, 3, 4–thiadiazoles, 1, 3, 4–oxadiazoles and 1, 2, 4–triazoles," Iranian Journal of Chemistry and Chemical Engineering. Cultural Division of Jihad Daneshgahi, Tehran, IR, vol. 17, No. 1, 1998, pp. 14–20.

International Search Report and Written Opinion for Application No. PCT/US2004/019174 dated Oct. 26, 2004.

Soos, T. et al.; "Novel Thermal Rearrangement of Fused Diaryl–v–Triazolium Salts to Neutral Indazole Derivatives. Fused Azolium Salts. 16.;" Journal of Organic Chemistry (1977), 62(4), 1136–1138.

*Primary Examiner*—Laura L. Stockton
(74) *Attorney, Agent, or Firm*—J. Michael Dixon; Charles W. Ashbrook

(57) ABSTRACT

Compounds comprising an indazolyl group and a thiazolyl group, preferably 7-substituted 3-(thiazol-2-yl)-1H-indazole compounds in which the indazolyl group and a thiazolyl group are each independently optionally substituted, are useful for the treatment or prophylaxis of bacterial infections in mammals. The compounds are believed to function by inhibiting gyrase B.

35 Claims, No Drawings

GYRASE INHIBITORS

RELATED APPLICATION INFORMATION

This application claims priority to U.S. Provisional Application No. 60/500,416, filed Sep. 5, 2003, U.S. Provisional Application No. 60/523,436, filed on Nov. 19, 2003, and U.S. Provisional Application No. 60/565,886, filed on Apr. 27, 2004, each of which is hereby incorporated by reference in its entirety.

BACKGROUND OF THE INVENTION

1. Field of the Invention

This invention relates to anti-bacterial compounds and methods of using them to treat bacterial infections.

2. Description of the Related Art

Bacterial resistance to drugs drives a continuing need for new anti-bacterial agents that to which the bacteria have not yet developed resistance. DNA gyrase is an enzyme found in many gram-positive and gram-negative bacteria. It is believed that DNA gyrase participates in the unfolding of the DNA double helix that takes before DNA replication by catalyzing ATP-dependent negative super-coiling of the DNA. DNA gyrase is believed to contain a complex of dimeric subunits, called gyrases A and B, that form an $A_2B_2$ active enzyme complex. It is further believed that the $A_2$ subunit carries out DNA binding, cleavage, and rejoining, while the $B_2$ subunit mediates ATPase activity.

Anti-bacterial agents that target the A subunit, such as quinolones, now face growing resistance among clinically important bacterial pathogens. Attempts to inhibit the B subunit of gyrase instead have not been entirely successful. Agents that inhibit catalysis of ATP hydrolysis by the B subunit (e.g., coumarins, such as novobiocin, and the cyclothialidines) were found to have low antimicrobial activities and unfavorable toxicity profiles (not related to the mechanism of action). U.S. Pat. Nos. 6,608,087 and 6,632,809, both of which are hereby incorporated by reference, describe other gyrase inhibitors. U.S. Pat. Nos. 5,140,034; 5,208,248 and 6,555,539, each of which is incorporated by reference in its entirety, disclose thiazolyl indazoles and their use as therapeutic agents, but these compounds are not known to be useful for inhibiting the B subunit of gyrase.

A need therefore exists for new anti-bacterial compounds, and particularly those that target the B subunit of bacterial DNA gyrase while overcoming the drawbacks of the existing inhibitors.

SUMMARY OF THE INVENTION

The present invention provides compounds comprising an indazolyl group and a thiazolyl group, preferably 7-substituted 3-(thiazol-2-yl)-1H-indazole compounds in which the indazolyl group and the thiazolyl group are each independently optionally substituted. In preferred embodiments, the compounds are useful for the treatment or prophylaxis of bacterial infections in mammals.

A preferred embodiment provides a compound comprising an indazolyl group and a thiazolyl group, the compound being represented by the structure

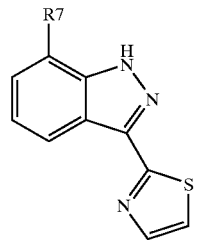

wherein R7 is selected from the group consisting of $C_1$–$C_6$ hydrocarbon, lower alkoxy, lower thioalkoxy, CN, $NO_2$, halogen, $CF_3$, and $OCF_3$; and wherein the $C_1$–$C_6$ hydrocarbon, indazolyl group, and thiazolyl group are optionally substituted on carbon; or a pharmaceutically acceptable salt, ester, solvate or prodrug thereof. Preferably, the compound of the formula (I) is synthetically produced. A compound of the formula (I) in an isolated, purified form is preferred.

Another embodiment provides a composition comprising the compound of claim 1 and a pharmaceutically acceptable carrier.

Another preferred embodiment provides method of treating or preventing a bacterial infection in a mammal, comprising administering to the mammal an effective amount of a compound of the formula (I) or composition thereof.

Another preferred embodiment provides a method for making a compound of the formula (I), comprising: treating an optionally substituted indazole represented by the formula

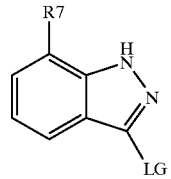

wherein R7 is selected from the group consisting of $C_1$–$C_6$ hydrocarbon, lower alkoxy, lower thioalkoxy, CN, $NO_2$, halogen, $CF_3$, and $OCF_3$; wherein the $C_1$–$C_6$ hydrocarbon is optionally substituted; and wherein LG represents a leaving group; with a cyanide salt to form an optionally substituted indazole nitrile represented by the formula

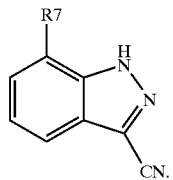

These and other embodiments are described in greater detail below.

DETAILED DESCRIPTION OF THE PREFERRED EMBODIMENTS

Definitions

Technical terms used herein have the meanings ascribed to them in the McGraw-Hill Dictionary of Scientific and Technical Terms, 6th ed., McGraw-Hill, New York, 2003, unless otherwise noted.

"Hydrocarbon" as used here includes alkyl, cycloalkyl, alkenyl, alkynyl, aryl, and combinations thereof.

"Alkoxy" or "alkoxyl" refers to hydrocarbon groups attached to the parent structure through an oxygen atom. "Lower alkoxy" refers to groups containing one to four carbon atoms.

"Aryl" refers to monocyclic 5- or 6-membered, bicyclic 9- or 10-membered, and tricyclic 13- or 14-membered aromatic carbocyclic rings, optionally bearing one or more substituents. Non-limiting examples of such rings include benzene, naphthalene, indane, tetralin, and fluorene, and of suitable substituents include halogen, —$R^1$, —$OR^1$, —OH, —SH, —$SR^1$, protected OH (such as acyloxy), optionally substituted phenyl (Ph), optionally substituted heterocycles, —$NO_2$, —CN, optionally substituted amino groups, optionally substituted carboxamido groups, —$NHCONHR^1$, —$NHCONR^1R^2$, —$NR^1COR^2$, —$NHCO_2R^1$, —$CO_2R^1$, —$CO_2H$, —$COR^1$, —$CONHR^1$, —$CONR^1R^2$, —$S(O)_2R^1$, —$SONH_2$, —$S(O)R^1$, —$SO_2NHR^1$, and —$NHSO_2R^1$, where $R^1$ and $R^2$ are optionally substituted aliphatic groups.

"Heteroaryl" refers to aryl groups containing up to three N, O, and/or S heteroatoms. Non-limiting examples include imidazole, pyridine, indole, thiophene, benzopyranone, thiazole, thiadiazole, furan, benzimidazole, quinoline, isoquinoline, quinoxaline, pyrimidine, pyrazine, tetrazole and pyrazole.

"Heterocycle" refers to a cycloalkyl or aryl group in which from one to three carbon atoms is replaced by N, O and/or S heteroatoms. The nitrogen and sulfur heteroatoms may optionally be oxidized, and the nitrogen heteroatom may optionally be quaternized or substituted with substituents such as $R^1$, $COR^1$, $SO_2R^1$, and $CO_2R^1$, where $R^1$ is an optionally substituted aliphatic group. In addition to the heteroaryl groups listed above, examples of heterocycles include piperidine, morpholine, thiomorpholine, piperazine, pyrrolidine, pyrrole, pyridazine, oxazole, oxadiazole, oxazoline, isoxazole, dioxane, tetrahydrofuran; and phenothiazine.

"Substituted" in reference to, e.g., an alkyl or other group refers to replacement of H atoms in that group with one or more of the following: lower alkyl; allyl; halogen; haloalkyl; hydroxy; lower alkoxy; hydroxy lower alkyl; carboxy; carboalkoxy (also referred to as alkoxycarbonyl); carboxyalkoxy; carboxamido (also referred to as alkylaminocarbonyl); cyano; formyl; acyl; nitro; amino; alkylamino; dialkylamino; anilino; mercapto; alkylthio; sulfoxide; sulfone; acylamino; amidino; phenyl; benzyl; heteroaryl; heterocycle; phenoxy; benzoyl; benzoyl substituted with amino, hydroxy, methoxy, methyl or halo; benzyloxy and heteroaryloxy. When the group that is substituted contains an alkyl segment, two hydrogen atoms on the same carbon atom may be replaced by oxo (=O). A substitutable nitrogen atom on a heterocyclic ring may be optionally substituted with substituents such as $R^1$, $COR^1$, $SO_2R^1$, and $CO_2R^1$, where $R^1$ is an aliphatic group or a substituted aliphatic group.

"Synthetically produced" means produced in a laboratory or manufacturing process, as opposed to produced in vivo through a naturally-occurring process.

"Aliphatic" as used here means straight chained, branched or cyclic $C_1$–$C_{12}$ hydrocarbons whether saturated or unsaturated. Non limiting examples of aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl) alkenyl.

"Pharmaceutically acceptable salt" as used herein refers to salts that are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 1977, 66: 1–19. The salts can be prepared in situ during the final isolation and purification of compounds of the formula (I) as described below, or separately by reaction of the free base with a suitable organic acid. Representative, acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

"Pharmaceutically acceptable ester" as used herein refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

"Pharmaceutically acceptable solvate" as used herein refers to an aggregate that comprises one or more molecules of the solute, such as a formula (I) compound, with one or more molecules of a solvent. When the solvent is water, the resulting solvate may be referred to as a "hydrate."

"Pharmaceutically acceptable carrier" as used herein refers to a non-toxic carrier that may be administered to a patient, together with a compound of this invention, and that does not adversely affect the pharmacological activity of the compound.

"Prodrug" as used herein refers compounds that are transformed in vivo to yield a compound of the formula (1) below, or a salt or metabolite thereof. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the formula (I) contains a carboxylic acid functional group, a prodrug can comprise an ester formed by the replacement of the hydrogen atom of the acid group with a group such as ($C_1$–$C_8$)alkyl, ($C_2$–$C_{12}$) alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$–$C_2$)alkylamino($C_2$–$C_3$) alkyl (such as b-dimethylaminoethyl), carbamoyl-($C_1$–$C_2$) alkyl, N,N-di($C_1$–$C_2$)alkylcarbamoyl-($C_1$–$C_2$)alkyl and piperidino-, pyrrolidino- or morpholino($C_2$–$C_3$)alkyl.

Similarly, if a compound of the formula (I) comprises an alcohol functional group, a prodrug can be formed by the replacement of the hydrogen atom of the alcohol group with a group such as ($C_1$–$C_6$)alkanoyloxymethyl, 1-(($C_1$–$C_6$) alkanoyloxy)ethyl, 1-methyl-1-(($C_1$–$C_6$)alkanoyloxy)ethyl, ($C_1$-$C_6$)alkoxycarbonyloxymethyl, N—($C_1$–$C_6$) alkoxycarbonylaminomethyl, succinoyl, ($C_1$–$C_6$)alkanoyl, α-amino($C_1$–$C_4$)alkanoyl, arylacyl and α-aminoacyl, or α-aminoacyl-a-aminoacyl, where each α-aminoacyl group is independently-selected from the naturally-occurring L-amino acids, $P(O)(OH)_2$, —$P(O)(O(C_1$–$C_6)alkyl)_2$ or glycosyl (the radical resulting from the removal of a hydroxyl group of the hemiacetal form of a carbohydrate).

If a compound of the formula (I) comprises an amine functional group, a prodrug can be formed by the replacement of a hydrogen atom in the amine group with a group such as R-carbonyl, RO-carbonyl, NRR'-carbonyl where R and R' are each independently (($C_1$–$C_{10}$)alkyl, ($C_3$–$C_7$) cycloalkyl, benzyl, or R-carbonyl is a natural α-aminoacyl or natural α-aminoacyl-natural α-aminoacyl, —C(OH)C(O) OY wherein (Y is H, ($C_1$–$C_6$)alkyl or benzyl), —$C(OY_0)Y_1$ wherein $Y_0$ is ($C_1$–$C_4$) alkyl and $Y_1$ is (($C_1$–$C_6$)alkyl, carboxy($C_1$–$C_6$)alkyl, amino($C_1$–$C_4$)alkyl or mono-N— or di-N,N— ($C_1$–$C_6$)alkylaminoalkyl, —$C(Y_2)Y_3$ wherein $Y_2$ is H or methyl and $Y_3$ is mono-N- or di-N,N-($C_1$-$C_6$) alkylamino, morpholino, piperidin-1-yl or pyrrolidin-1-yl.

Compounds and Compositions

A preferred embodiment provides compounds of the formula (I) comprising an indazolyl group and a thiazolyl group:

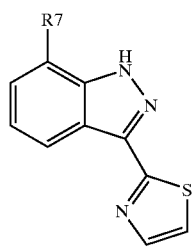

(I)

In formula (I), R7 is preferably selected from the group consisting of $C_1$–$C_6$ hydrocarbon, lower alkoxy, lower thioalkoxy, CN, $NO_2$, halogen, $CF_3$, and $OCF_3$. More preferably, R7 is selected from the group consisting of methyl, ethyl, propyl, allyl, F, Cl, and Br. The $C_1$–$C_6$ hydrocarbon, indazolyl group, and thiazolyl group are optionally substituted, preferably substituted on carbon. The indazolyl group preferably bears at least one substituent selected from the group consisting of optionally substituted $C_1$–$C_6$ hydrocarbon (e.g., methyl, ethyl, propyl, allyl, methylcyclopropyl), lower alkoxy, optionally substituted heterocycle, CN, $NO_2$, halogen (e.g., F, Cl, Br, I), $CF_3$, and $OCF_3$. Preferably, the substituent is attached to a carbon atom of the indazolyl group rather than a nitrogen atom.

The thiazolyl group preferably bears at least one substituent selected from the group consisting of optionally substituted $C_1$–$C_{10}$ hydrocarbon (e.g., methyl, ethyl), optionally substituted $C_1$–$C_{10}$ heterocycle, optionally substituted carboxamido, optionally substituted aminocarboxy, optionally substituted $C_1$–$C_6$ alkoxy, optionally substituted $C_1$–$C_6$ alkoxycarbonyl (e.g., $COOCH_3$, $COOCH_2CH_3$), OH, COOH, $COOR^3$, and $CONR^8R^9$; wherein $R^3$ is selected from the group consisting of optionally substituted heterocycle and $C_1$–$C_6$ alkyl substituted by heterocycle; wherein $R^8$ and $R^9$ are independently selected from the group consisting of H, optionally substituted heterocycle, and optionally substituted $C_1$–$C_6$ hydrocarbon, wherein $R^8$ and $R^9$ may together form a four-, five-, or six-membered optionally substituted heterocyclic ring including the N atom to which $R^8$ and $R^9$ are attached, and wherein for said ring one to three carbon atoms may optionally each independently be replaced by an atom selected from the group consisting of N, O, and S. Examples of substituents thus include methyl, ethyl, OH, phenyl, COOH, $COOCH_3$, $COOCH_2CH_3$, and $N(CH_3)(CH_2CH_3)$. In preferred embodiments, the thiazolyl group is attached to a carbonyl carbon of at least one substituent represented by a structure selected from the group consisting of

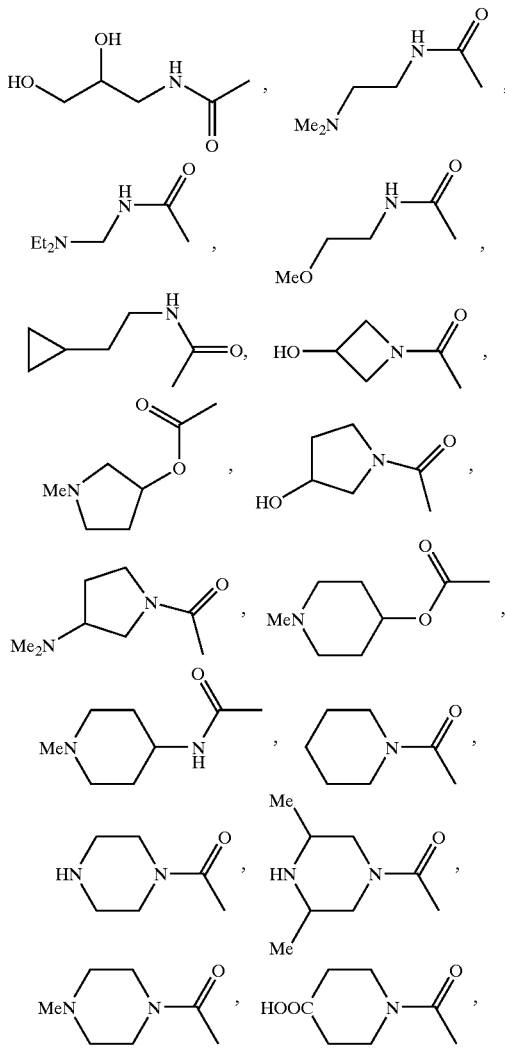

-continued

For compounds of the formula (I) in which the thiazolyl group bears a phenyl substituent, the phenyl is optionally substituted with at least one substituent selected from the group consisting of OH, OCH$_3$, F, Cl, Br, optionally substituted piperazin-1-yl, and optionally substituted morpholin-4-yl. Examples of phenyl groups include 3-hydroxyphenyl, 4-hydroxyphenyl, 3-methoxyphenyl, 3-fluorophenyl, 4-fluorophenyl, 4-fluoro-3-hydroxy-phenyl, 3,4-difluoro-phenyl, 3,5-difluoro-phenyl, 4-bromo-3-methoxy-phenyl, 4-(4-methyl-piperazin-1-yl)-phenyl, and 4-(morpholin-4-yl)-phenyl. For compounds of the formula (I) in which the thiazolyl group bears a pyridyl substituent, the pyridyl is optionally substituted with at least one substituent selected from the group consisting of $C_1$–$C_6$ alkyl, F, Cl, Br, I, CF$_3$, 3,5-dimethyl-piperazin-1-yl, and morpholin-4-yl. Examples of pyridyl groups include pyridin-3-yl, 6-methyl-pyridin-3-yl, 6-chloro-pyridin-3-yl, and 6-trifluoromethyl-pyridin-3-yl It is apparent from the foregoing that the thiazolyl group may optionally bear two substituents. Preferably, each of the two substituents on the thiazolyl group is independently selected from the group consisting of optionally substituted $C_1$–$C_{10}$ hydrocarbon, COOH, optionally substituted $C_1$–$C_6$ alkoxycarbonyl, OH, COOR$^3$, and CONR$^8$R$^9$, wherein R$^3$ is selected from the group consisting of optionally substituted heterocycle and $C_1$–$C_6$ alkyl substituted by heterocycle; wherein R$^8$ and R$^9$ are independently selected from the group consisting of H, optionally substituted heterocycle, and optionally substituted $C_1$–$C_6$ hydrocarbon, wherein R$^8$ and R$^9$ may together form a four-, five-, or six-membered optionally substituted heterocyclic ring including the N atom to which R and R' are attached, and wherein for said ring one to three carbon atoms may optionally each independently be replaced by an atom selected from the group consisting of N, O, and S.

Those skilled in the art will recognize that certain compounds of the formula (I) may exist in tautomeric forms, all such forms of the compounds being within the scope of the invention. Unless otherwise stated, structures depicted herein also encompass all stereochemical forms of the structure, including the R and S configurations for each asymmetric center. Therefore, single stereochemical isomers as well as enantiomeric and diastereomeric mixtures of the present compounds are within the scope of the invention. Preferred compounds of the formula (I) are synthetically produced to provide an isolated, substantially pure form according to the synthetic methods described below.

Those skilled in the art will understand that the in vivo effects resulting from administration of the compounds of the formula (I) may result not from the compounds themselves, but instead by one or more products of degradation, such as by a metabolic process. Thus, those skilled in the art will understand that reference herein to a compound of the formula (I) includes pharmacologically acceptable esters, amides, salts (e.g., metal salts), hydrates, and other derivatives thereof (known in the art as "pro-drugs") that undergo biotransformation to yield the active drug. Pro-drugs are described generally in, e.g., Goodman and Gilman's "Biotransformation of Drugs," in the Pharmacological Basis of Therapeutics, 8$^{th}$ Ed., McGraw Hill, Int. Ed. 1992, pages 13–15, which is hereby incorporated by reference in its entirety. Particularly favored derivatives or prodrugs are those that increase the bioavailability of the compounds of the formula (I) when such compounds are administered to a mammal (e.g., by allowing an orally administered compound to be more readily absorbed into the blood) or that enhance delivery of the parent compound to a biological compartment (e.g., the brain or lymphatic system) relative to the parent species.

A preferred embodiment provides compositions comprising a compound of the formula (I) and a pharmaceutically acceptable carrier. Pharmaceutically acceptable carriers useful in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as a-tocopherol, polyethyleneglycol 1000 succinate, or other similar polymeric delivery matrices.

Certain compounds of the formula (I) possess an acidic or basic group, and may therefore form salts with pharmaceutically-acceptable cations or anions. All such pharmaceutically-acceptable salts are contemplated in the present invention. The identities of pharmaceutically-acceptable cations and anions are well-known in the art, and appear in such compendia as the Physicians' Desk Reference, 56th ed., Medical Economics Company, Inc., Montvale, N.J., 2002. The compounds may also form hydrates or exist in a substantially anhydrous form.

Pharmaceutical compositions for parenteral administration, such as by injection intravenously, preferably contain a pharmaceutically acceptable amount of a compound of the formula (I) as a soluble salt dissolved in a pharmaceutically acceptable liquid carrier such as, for example, water-for-injection and a buffer to provide a suitably buffered isotonic solution having, for example, a pH of about 3.5–6. Suitable buffering agents include, for example, trisodium orthophosphate, sodium bicarbonate, sodium citrate, N-methylglucamine, L(+)-lysine and L(+)-arginine. The compounds of the formula (I) generally will be dissolved in the carrier in an amount sufficient to provide a pharmaceutically acceptable injectable concentration in the range of about 1 mg/mL to about 400 mg/mL of solution. The resulting liquid pharmaceutical composition will be so administered as to obtain a dosage effective against bacteria.

Nonlimiting examples of preferred compounds of the formula (I) include:

1-[2-(5,7-dimethyl-1H-indazol-3-yl)-5-pyridin-3-yl-thiazol-4-yl]-2-(1-methyl-piperidin-4-yl)-ethanone;

[2-(5,7-Dimethyl-1H-indazol-3-yl)-5-pyridin-3-yl-thiazol-4-yl]-(4-methyl-piperazin-1-yl)-methanone;

(3-dimethylamino-pyrrolidin-1-yl)-[2-(6-fluoro-7-methyl-1H-indazol-3-yl)-5-pyridin-3-yl-thiazol-4-yl]-methanone;

(3-dimethylamino-pyrrolidin-1-yl)-[2-(6-fluoro-7-methyl-1H-indazol-3yl)-5-(6-methyl-pyridin-3-yl)-thiazol-4-yl]-methanone;

(3-dimethylamino-pyrrolidin-1-yl)-[2-(7-methyl-1H-indazol-3-yl)-5-pyridin-3-yl-thiazol-4-yl]-methanone;

(3-dimethylamino-pyrrolidin-1-yl)-[2-(7-methyl-1H-indazol-3-yl)-5-(6-methyl-pyridin-3-yl)-thiazol-4-yl]-methanone;

(3,5-dimethyl-piperidin-1-yl)-[2-(7-methyl-1H-indazol-3-yl)-5-pyridin-3-yl-thiazol-4-yl]-methanone;

(3-dimethylamino-pyrrolidin-1-yl)-[2-(7-methyl-1H-indazol-3-yl)-5-(6-trifluoromethyl-pyridin-3-yl)-thiazol-4-yl]-methanone;

(3-dimethylamino-pyrrolidin-1-yl)-[2-(7-methyl-1H-indazol-3-yl)-5-pyridin-3-yl-thiazol-4-yl]-methanone;

(3-dimethylamino-pyrrolidin-1-yl)-[5-(3-methoxy-phenyl)-2-(7-methyl-1H-indazol-3-yl)-thiazol-4-yl]-methanone;

(3-dimethylamino-pyrrolidin-1-yl)-[5-(4-hydroxy-phenyl)-2-(7-methyl-1H-indazol-3-yl)-thiazol-4-yl]-methanone;

(3-hydroxy-azetidin-1-yl)-[2-(7-methyl-1H-indazol-3-yl)-5-pyridin-3-yl-thiazol-4-yl]-methanone;

(3-hydroxy-pyrrolidin-1-yl)-[2-(7-methyl-1H-indazol-3-yl)-5-(6-morpholin-4-yl-pyridin-3-yl)-thiazol-4-yl]-methanone;

(3-hydroxy-pyrrolidin-1-yl)-[2-(7-methyl-1H-indazol-3-yl)-5-pyridin-3-yl-thiazol-4-yl]-methanone;

[2-(6-chloro-7-methyl-1H-indazol-3-yl)-5-pyridin-3-yl-thiazol-4-yl]-(4-methyl-piperazin-1-yl)-methanone;

[2-(6-chloro-7-methyl-1H-indazol-3-yl)-5-pyridin-3-yl-thiazol-4-yl]-(3-hydroxy-pyrrohidin-1-yl)-methanone;

[2-(6-chloro-7-methyl-1H-indazol-3-yl)-5-pyridin-3-yl-thiazol-4-yl]-(3-dimethylamino-pyrrolidin-1-yl)-methanone;

[2-(7-methyl-1H-indazol-3-yl)-5-pyridin-3-yl-thiazol-4-yl]-(4-methyl-piperazin-1-yl)-methanone;

[2-(7-methyl-1H-indazol-3-yl)-5-pyridin-3-yl-thiazol-4-yl]-(4-pyridin-4-yl-piperazin-1-yl)-methanone;

[2-(7-methyl-1H-indazol-3-yl)-5-pyridin-3-yl-thiazol-4-yl]-morpholin-4-yl-methanone;

[2-(7-methyl-1H-indazol-3-yl)-5-pyridin-3-yl-thiazol-4-yl]-piperidin-1-yl-methanone;

[5-(3,4-difluoro-phenyl)-2-(7-methyl-1H-indazol-3-yl)-thiazol-4-yl]-(3-dimethylamino-pyrrolidin-1-yl)-methanone;

[5-(3,4-difluoro-phenyl)-2-(7-methyl-1H-indazol-3-yl)-thiazol-4-yl]-(3-hydroxy-pyrrolidin-1-yl)-methanone;

[5-(3,4-difluoro-phenyl)-2-(7-methyl-1H-indazol-3-yl)-thiazol-4-yl]-(4-methyl-piperazin-1-yl)-methanone;

[5-(3,5-difluoro-phenyl)-2-(7-methyl-1H-indazol-3-yl)-thiazol-4-yl]-(3-hydroxy-pyrrolidin-1-yl)-methanone;

[5-(3,5-difluoro-phenyl)-2-(7-methyl-1H-indazol-3-yl)-thiazol-4-yl]-(4-methyl-piperazin-1-yl)-methanone;

[5-(3-fluoro-phenyl)-2-(7-methyl-1H-indazol-3-yl)-thiazol-4-yl]-(4-methyl-piperazin-1-yl)-methanone;

[5-(4-fluoro-3-hydroxy-phenyl)-2-(7-methyl-1H-indazol-3-yl)-thiazol-4-yl]-(4-methyl-piperazin-1-yl)-methanone;

[5-(4-fluoro-phenyl)-2-(7-methyl-1H-indazol-3-yl)-thiazol-4-yl]-(3-hydroxy-pyrrolidin-1-yl)-methanone;

[5-(4-fluoro-phenyl)-2-(7-methyl-1H-indazol-3-yl)-thiazol-4-yl]-(4-methyl-piperazin-1-yl)-methanone;

[5-(6-chloro-pyridin-3-yl)-2-(7-methyl-1H-indazol-3-yl)-thiazol-4-yl]-dimethylamino-pyrrolidin-1-yl)-methanone;

[5-(6-chloro-pyridin-3-yl)-2-(7-methyl-1H-indazol-3-yl)-thiazol-4-yl]-(3-hydroxy-pyrrolidin-1-yl)-methanone;

[5-[6-(3,5-dimethyl-piperazin-1-yl)-pyridin-3-yl]-2-(7-methyl-1H-indazol-3-yl)-thiazol-4-yl]-(3-hydroxy-pyrrolidin-1-yl)-methanone;

{4-[2-(1H-indazol-3-yl)-thiazol-4-yl]-phenyl}-(4-methyl-piperazin-1-yl)-methanone;

{4-[2-(1H-indazol-3-yl)-thiazol-4-yl]-phenyl}-morpholin-4-yl-methanone;

1-[2-(7-methyl-1H-indazol-3-yl)-5-pyridin-3-yl-thiazole-4-carbonyl]-piperidine-4-carboxylic acid;

2-(1H-indazol-3-yl)-4-phenyl-thiazole-5-carboxylic acid ethyl ester;

2-(1H-indazol-3-yl)-5-phenyl-thiazol-4-ol;

2-(1H-indazol-3-yl)-5-phenyl-thiazole-4-carboxylic acid (2,3-dihydroxy-propyl)-amide;

2-(1H-indazol-3-yl)-5-phenyl-thiazole-4-carboxylic acid (2-dimethyl-amino-ethyl)-amide;

2-(1H-indazol-3-yl)-5-phenyl-thiazole-4-carboxylic acid (2-methoxy-ethyl)-amide;

2-(1H-indazol-3-yl)-5-phenyl-thiazole-4-carboxylic acid cyclopropylmethyl-amide;

2-(1H-indazol-3-yl)-5-phenyl-thiazole-4-carboxylic acid methyl ester;

2-(4-chloro-7-methyl-1H-indazol-3-yl)-5-pyridin-3-yl-thiazole-4-carboxylic acid methyl ester;

2-(6-chloro-7-methyl-1H-indazol-3-yl)-5-pyridin-3-yl-thiazole-4-carboxylic acid methyl ester;

2-(7-ethyl-1H-indazol-3-yl)-5-phenyl-thiazole-4-carboxylic acid methyl ester;

2-(7-methyl-1H-indazol-3-yl)-5-(6-trifluoromethyl-pyridin-3-yl)-thiazole-4-carboxylic acid methyl ester;

2-(7-methyl-1H-indazol-3-yl)-5-phenyl-thiazole-4-carboxylic acid 2-morpholin-4-yl-ethyl ester;

2-(7-methyl-1H-indazol-3-yl)-5-phenyl-thiazole-4-carboxylic acid methyl ester;

2-(7-methyl-1H-indazol-3-yl)-5-pyridin-3-yl-thiazole-4-carboxylic acid ethyl-methyl-amide;

2-(7-methyl-1H-indazol-3-yl)-5-pyridin-3-yl-thiazole-4-carboxylic acid 1-methyl-piperidin-4-yl ester;
2-(7-methyl-1H-indazol-3-yl)-5-pyridin-3-yl-thiazole-4-carboxylic acid 1-methyl-pyrrolidin-3-yl ester;
2-(7-methyl-1H-indazol-3-yl)-5-pyridin-3-yl-thiazole-4-carboxylic acid (2-dimethylamino-ethyl)-methyl-amide;
2-(7-methyl-1H-indazol-3-yl)-5-pyridin-3-yl-thiazole-4-carboxylic acid (1-methyl-piperidin-4-yl)-amide;
2-(7-methyl-1H-indazol-3-yl)-5-pyridin-3-yl-thiazole-4-carboxylic acid;
2-(7-methyl-1H-indazol-3-yl)-5-pyridin-3-yl-thiazole-4-carboxylic acid (2-diethylamino-ethyl)-amide;
2-(7-methyl-1H-indazol-3-yl)-5-pyridin-3-yl-thiazole-4-carboxylic acid methyl ester;
2-(7-methyl-1H-indazol-3-yl)-5-pyridin-3-yl-thiazole-4-carboxylic acid ethyl ester;
2-[2-(1H-indazol-3-yl)-thiazol-4-yl]-phenol;
2-bromo-5-[2-(1H-indazol-3-yl)-4-methyl-thiazol-5-yl]-phenol;
2-hydroxy-5-[2-(1H-indazol-3-yl)-5-methyl-thiazol-4-yl]-benzoic acid;
3-(4,5-diphenyl-thiazol-2-yl)-1H-indazole;
3-(4-ethyl-5-phenyl-thiazol-2-yl)-1H-indazole;
3-(4-ethyl-thiazol-2-yl)-1H-indazole;
3-(4-naphthalen-2-yl-thiazol-2-yl)-1H-indazole;
3-(4-phenyl-thiazol-2-yl)-1H-indazole;
3-(4-p-tolyl-thiazol-2-yl)-1H-indazole;
3-(4-pyridin-2-yl-thiazol-2-yl)-1H-indazole;
3-(4-pyridin-3-yl-thiazol-2-yl)-1H-indazole;
3-(5-methyl-4-phenyl-thiazol-2-yl)-1H-indazole;
3-(5-phenyl-thiazol-2-yl)-1H-indazole;
3-(5-phenyl-thiazol-2-yl)-1H-indazole;
3-[2-(1H-indazol-3-yl)-4-methyl-thiazol-5-yl]-phenol;
3-[2-(1H-indazol-3-yl)-4-methyl-thiazol-5-yl]-phenol;
3-[2-(1H-indazol-3-yl)-thiazol-4-yl]-benzoic acid;
3-[2-(7-chloro-1H-indazol-3-yl)-4-methyl-thiazol-5-yl]-phenol;
3-[4-(2,5-dimethyl-phenyl)-thiazol-2-yl]-1H-indazole;
3-[4-(2-fluoro-phenyl)-thiazol-2-yl]-1H-indazole;
3-[4-(2-methoxy-phenyl)-thiazol-2-yl]-1H-indazole;
3-[4-(3,4-dichloro-phenyl)-thiazol-2-yl]-1H-indazole;
3-[4-(3,4-difluoro-phenyl)-thiazol-2-yl]-1H-indazole;
3-[4-(3-bromo-phenyl)-thiazol-2-yl]-1H-indazole;
3-[4-(3-fluoro-phenyl)-thiazol-2-yl]-1H-indazole;
3-[4-(3-methoxy-phenyl)-thiazol-2-yl]-1H-indazole;
3-[4-(4-chloro-phenyl)-thiazol-2-yl]-1H-indazole;
3-[4-(4-methanesulfonyl-phenyl)-thiazol-2-yl]-1H-indazole;
3-[4-(4-methoxy-phenyl)-thiazol-2-yl]-1H-indazole;
3-[4-(4-morpholin-4-yl-phenyl)-thiazol-2-yl]-1H-indazole;
3-[4-(4-pyrrolidin-1-yl-phenyl)-thiazol-2-yl]-1H-indazole;
3-[4-methyl-5-(4-morpholin-4-yl-phenyl)-thiazol-2-yl]-1H-indazole;
3-[5-(3-methoxy-phenyl)-4-methyl-thiazol-2-yl]-1H-indazole;
3-[5-(3-methoxy-phenyl)-4-methyl-thiazol-2-yl]-1H-indazole;
3-[5-(4-bromo-3-methoxy-phenyl)-4-methyl-thiazol-2-yl]-1H-indazole;
3-[5-(6-chloro-pyridin-3-yl)-4-methyl-thiazol-2-yl]-1H-indazole;
3-{4-methyl-5-[4-(4-methyl-piperazin-1-yl)-phenyl]-thiazol-2-yl}-1H-indazole;
4-[2-(1H-indazol-3-yl)-thiazol-4-yl]-benzoic acid methyl ester;
4-[2-(1H-indazol-3-yl)-thiazol-4-yl]-benzoic acid;
4-[2-(1H-indazol-3-yl)-thiazol-4-yl]-benzonitrile;
5-(3-fluoro-phenyl)-2-(7-methyl-1H-indazol-3-yl)-thiazole-4-carboxylic acid methyl ester;
5-(4-fluoro-phenyl)-2-(7-methyl-1H-indazol-3-yl)-thiazole-4-carboxylic acid ethyl ester;
5-(4-hydroxy-phenyl)-2-(7-methyl-1H-indazol-3-yl)-thiazole-4-carboxylic acid methyl ester;
5-(6-chloro-pyridin-3-yl)-2-(7-methyl-1H-indazol-3-yl)-thiazole-4-carboxylic acid methyl ester;
7-chloro-3-[5-(3-methoxy-benzyl)-thiazol-2-yl]-1H-indazole;
7-chloro-3-[5-(3-methoxy-phenyl)-4-methyl-thiazol-2-yl]-1H-indazole;
diethyl-{4-[2-(1H-indazol-3-yl)-thiazol-4-yl]-phenyl}-amine;
N-(2-dimethylamino-ethyl)-3-[2-(1H-indazol-3-yl)-thiazol-4-yl]-benzamide.

Methods of Making Compounds and Compositions

Compounds of the formula (I) are preferably prepared according to the following synthetic scheme:

Acetylation

Acetylation preferably comprises reacting an aryl amine with an acetyl halide to form an optionally substituted aryl amide represented by the formula (II):

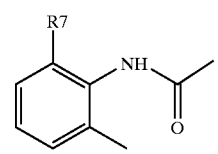

(II)

R7 is preferably selected from the group consisting of $C_1-C_6$ hydrocarbon, lower alkoxy, lower thioalkoxy, CN, $NO_2$, halogen, $CF_3$, and $OCF_3$; wherein the $C_1-C_6$ hydrocarbon and the aryl ring of the aryl amide are optionally substituted. Acetylation is illustrated by the following: An aryl amine such as aniline (82.5 mmoles) is dissolved in 400 mL of dichloromethane and cooled to 0° C. To this solution is added dropwise acetyl chloride (71 mL, 1 mole) followed by a 200 mL solution of triethyl amine (140 mL, 1 mole). This solution is stirred until reaction is complete. The resulting solid is filtered off and the filtrate poured into brine, extracted twice with dichloromethane, dry filtered and concentrated to give the acetylated amine.

Cyclization

Cyclization preferably comprises reacting the optionally substituted aryl amide with an alkyl nitrite in the presence of an acid to form an optionally substituted indazole represented by the formula (III):

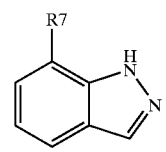

(III)

Cyclization is illustrated by the following: An acetylated amine such as N-(2,6-dimethylphenyl)-acetamide (1 eq) is dissolved in dichloroethane. To this solution is added acetic acid (1.1 eq) followed by the dropwise addition of isoamyl nitrite (1.1 eq). The reaction is then heated to reflux overnight, poured into water and extracted two additional times with dichloromethane. The extracts are combined, washed with saturated bicarbonate, then brine, and dried with magnesium sulfate filter before being concentrated to a solid. Yields typically 80%.

Iodination

Iodination preferably comprises reacting the optionally substituted indazole with iodine in the presence of a base to form an optionally substituted iodinated indazole represented by the formula (IV):

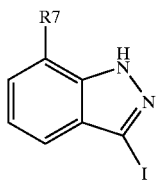

(IV)

Iodination is illustrated by the following: The optionally substituted indazole represented by the formula (III) (1 eq) is dissolved in DMF (0.5 M) and to this solution is added iodine crystals (3 eq) and KOH pellets (5 eq). This reaction is allowed to stir at RT until complete by thin layer chromatography (TLC), approximately 3 hours. The solution is concentrated to about one third volume, and then poured into a 5% $NaHSO_3$ solution and extracted with ether 3 times. The ether extracts are washed with water followed by saturated brine solution and dried over magnesium sulfate. The drying agent is removed by filtration and the ether solution concentrated to an orange solid to quantitative yields of the 3-iodo-indazole.

Those skilled in the art will appreciate that iodine is a leaving group (LG), and that other leaving groups may be used in place of the iodine in the compound represented by the formula (IV), thereby forming a compound represented by the formula (V):

(V)

For the compound represented by the formula (V), LG represents a leaving group. Preferred leaving groups include chloro, bromo, iodo, trifluoromethanesulfonate, methanesulfonate, p-toluenesulfonate, and trifluoroacetate. Iodo is a highly preferred leaving group.

Nitrile Displacement

Nitrile displacement preferably comprises reacting the optionally substituted iodinated indazole with a cyanide salt to form an optionally substituted indazole nitrile represented by the formula (VI):

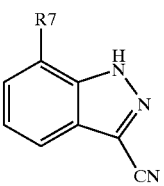

(VI)

Nitrile displacement is illustrated by the following: The optionally substituted iodinated indazole is dissolved in anhydrous N-methylpyrrolidinone (0.5 M). To this solution is added sodium cyanide (2 equivalents) and copper (I) cyanide (3 equivalents). The solution is heated to 135° C. for 6 hours or until complete by TLC or HPLC. The reaction is then concentrated to 1/3 volume and partitioned between ether and water. The resulting suspension is filtered through diatomaceous earth. The filtrate is separated and extracted with two additional portions of ether. The combined extracts are washed with water and brine, dried over magnesium sulfate, filtered and concentrated to an off white solid. (50% yield).

Those skilled in the art will understand that iodine is an example of a leaving group, and thus that nitrile displacement may also be carried out in a similar fashion using compounds of the formula (V).

Thioamide Formation

Thioamide formation preferably comprises reacting the optionally substituted indazole nitrile with hydrogen sulfide in the presence of a base to form an optionally substituted indazole thioamide represented by the formula (VII):

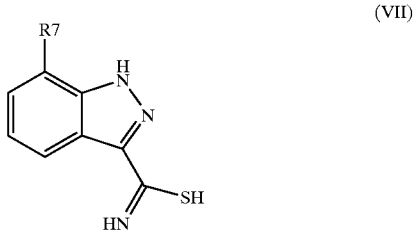

(VII)

Thioamide formation is illustrated by the following: The optionally substituted indazole nitrile is dissolved in 20% triethyl amine in pyridine and cooled to 0° C. The solution is then saturated for 10 minutes with hydrogen sulfide gas. The reactor is sealed and allowed to stir while warming to room temperature. After 3 hours, or when the reaction is complete by TLC, it is de-gassed with a light vacuum before being concentrated to a yellow solid. The solid is suspended in hexane and filtered under vacuum. The solid is then dried under high vacuum with $P_2O_5$ until dried to a constant weight.

Cyclization

Cyclization preferably comprises reacting the optionally substituted indazole thioamide with a carbonyl compound to form a compound of the formula (I). Preferably, the carbonyl compound is substituted with a leaving group in the position alpha to the carbonyl. Preferred carbonyl compounds include optionally substituted α-LG aldehyde, optionally substituted α-LG ketone, and optionally substituted α-LG ester. Cyclization is illustrated in Examples 3–4 below.

It will be understood by those skilled in the art that additional or alternate chemical reactions or process steps may be employed in addition to or instead of those set forth in the synthetic scheme outlined above. Thus, the knowledge of those skilled in the art may be combined with the teachings provided herein to prepare a wide variety of compounds of the formula (I). For example, Table 1 provides the names and structures of various preferred compounds of the formula (I) prepared in accordance with the methods described herein.

TABLE 1

| No. | Name | Structure |
|-----|------|-----------|
| 1. | 2-(1H-Indazol-3-yl)-5-phenyl-thiazol-4-ol | 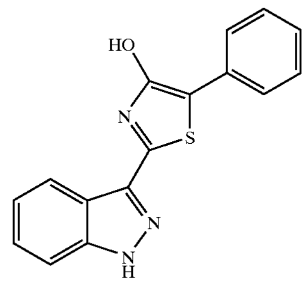 |
| 2. | 3-(4-Pyridin-3-yl-thiazol-2-yl)-1H-indazole | 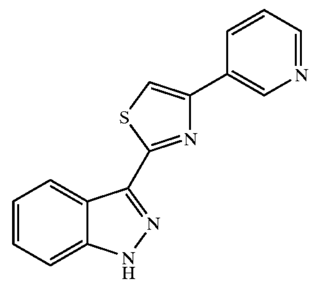 |
| 3. | 3-(4-Phenyl-thiazol-2-yl)-1H-indazole | 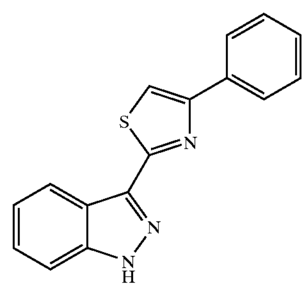 |
| 4. | 3-(5-Phenyl-thiazol-2-yl)-1H-indazole | 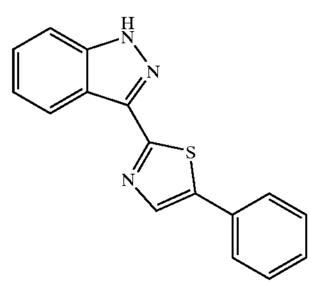 |
| 5. | 2-(1H-Indazol-3-yl)-4-phenyl-thiazole-5-carboxylic acid ethyl ester | 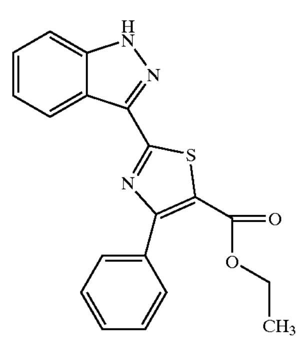 |

TABLE 1-continued

| No. | Name | Structure |
|---|---|---|
| 6. | 4-[2-(1H-Indazol-3-yl)-thiazol-4-yl]-benzoic acid | 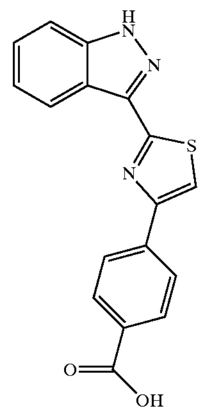 |
| 7. | 4-[2-(1H-Indazol-3-yl)-thiazol-4-yl]-benzoic acid methyl ester | 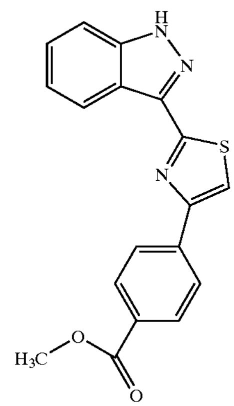 |
| 8. | N-(2-Dimethylamino-ethyl)-4-[2-(1H-indazol-3-yl)-thiazol-4-yl]-benzamide | 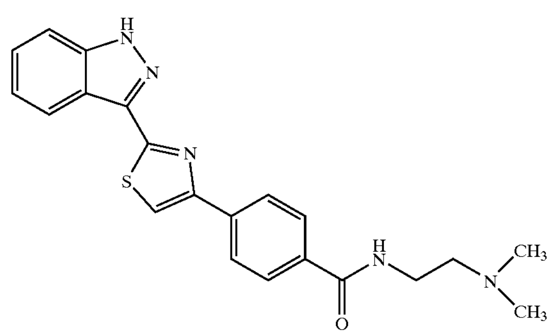 |
| 9. | 3-[2-(1H-Indazol-3-yl)-thiazol-4-yl]-benzoic acid | 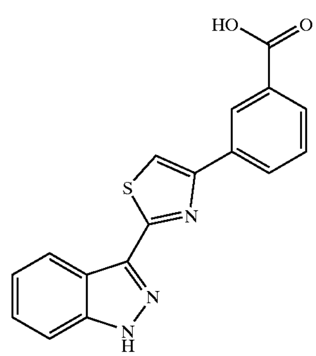 |

TABLE 1-continued

| No. | Name | Structure |
|---|---|---|
| 10. | 3-(5-Methyl-4-phenyl-thiazol-2-yl)-N-indazole | 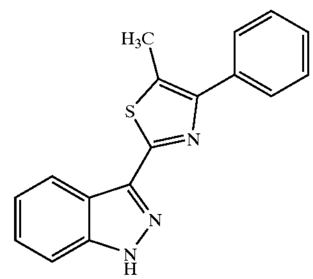 |
| 11. | N-(2-Dimethylamino-ethyl)-3-[2-(1H-indazol-3-yl)-thiazol-4-yl]-benzamide | 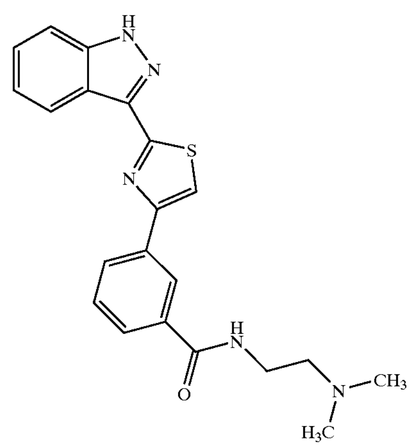 |
| 12. | {4-[2-(1H-Indazol-3-yl)-thiazol-4-yl]-phenyl}-(4-methyl-piperazin-1-yl)-methanone | 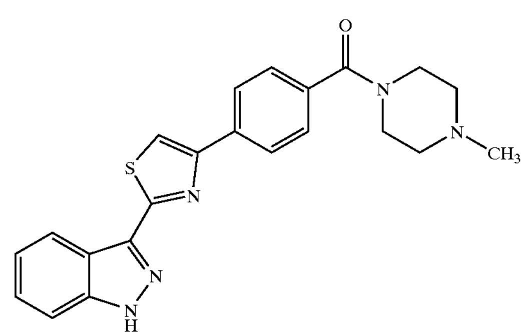 |
| 13. | {4-[2-(1H-Indazol-3-yl)-thiazol-4-yl]-phenyl}-morpholin-4-yl-methanone | 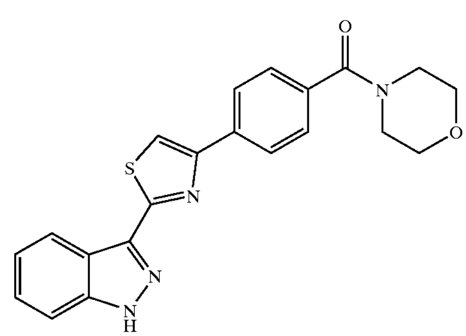 |

TABLE 1-continued

| No. | Name | Structure |
| --- | --- | --- |
| 14. | 3-[5-(3-Methoxy-phenyl)-4-methyl-thiazol-2-yl]-1H-indazole | 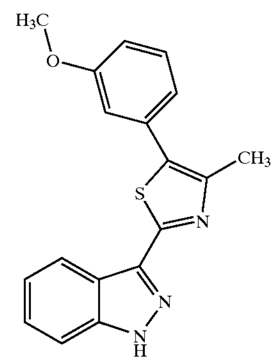 |
| 15. | 3-[4-(4-Bromo-phenyl)-5-methyl-thiazol-2-yl]-1H-indazole | 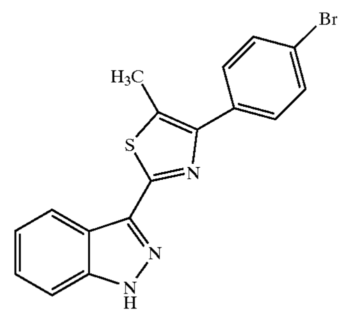 |
| 16. | 3-[5-Methyl-4-(4-morpholin-4-yl-phenyl)-thiazol-2-yl]-1H-indazole | 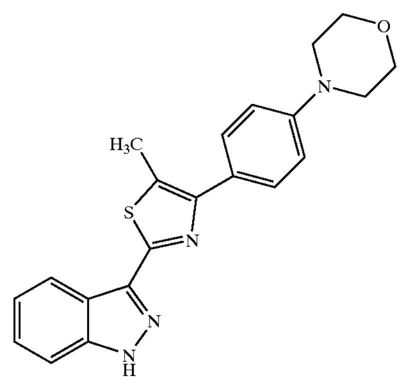 |
| 17. | 3-[2-(1H-Indazol-3-yl)-4-methyl-thiazol-5-yl]-phenol | 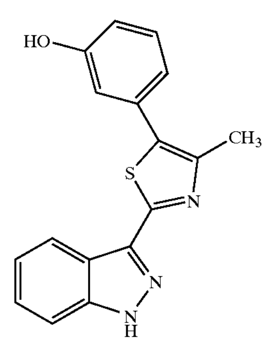 |

TABLE 1-continued

| No. | Name | Structure |
|---|---|---|
| 18. | 3-{5-Methyl-4-[4-(4-methyl-piperazin-1-yl)-phenyl]-thiazol-2-yl}-1H-indazole | 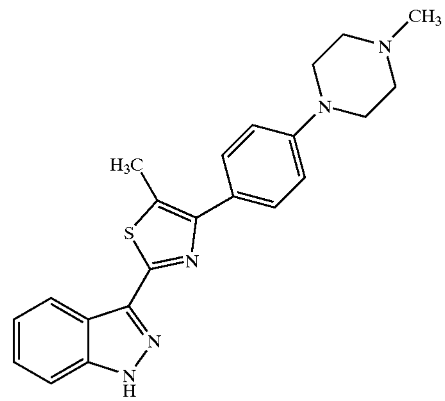 |
| 19. | 2-Hydroxy-5-[2-(1H-indazol-3-yl)-5-methyl-thiazol-4-yl]-benzoic acid | 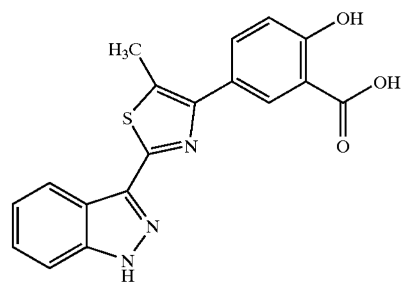 |
| 20. | 2-(7-Fluoro-1H-indazol-3-yl)-5-phenyl-thiazol-4-ol | 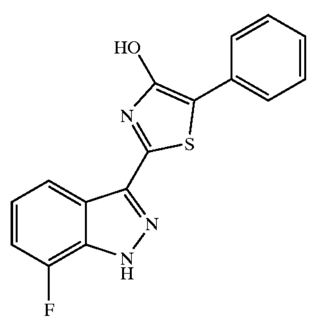 |
| 21. | 5-[2-(1H-Indazol-3-yl)-5-methyl-thiazol-4-yl]-2-morpholin-4-yl-benzoic acid | 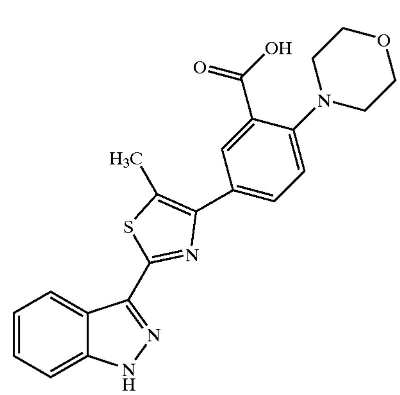 |

TABLE 1-continued
| No. | Name | Structure |
|---|---|---|
| 22. | 5-[2-(1H-Indazol-3-yl)-5-methyl-thiazol-4-yl]-2-morpholin-4-yl-benzoic acid methyl ester | 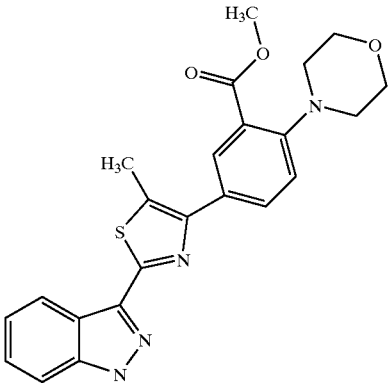 |
| 23. | 3-[4-(4-Bromo-phenyl)-5-methyl-thiazol-2-yl]-7-fluoro-1H-indazole | 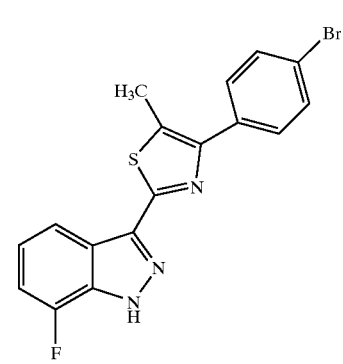 |
| 24. | 7-Fluoro-3-{5-methyl-4-[4-(4-methyl-piperazin-1-yl)-phenyl]-thiazol-2-yl}-1H-indazole | 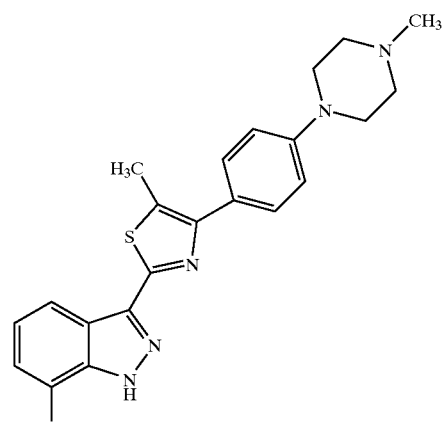 |
| 25. | 3-[5-(4-Bromo-3-methoxy-phenyl)-4-methyl-thiazol-2-yl]-1H-indazole | 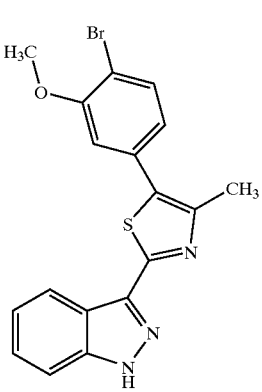 |

TABLE 1-continued

| No. | Name | Structure |
|-----|------|-----------|
| 26. | 7-Chloro-3-[5-(3-methoxy-phenyl)-4-methyl-thiazol-2-yl]-1H-indazole | 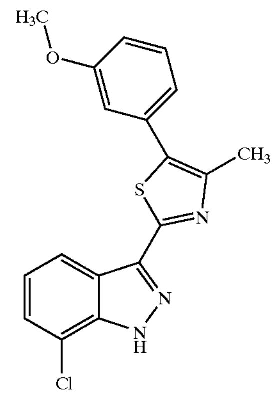 |
| 27. | 7-Chloro-3-[5-(3-methoxy-benzyl)-thiazol-2-yl]-1H-indazole | 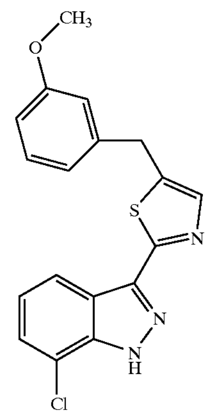 |
| 28. | 3-[2-(7-Chloro-1H-indazol-3-yl)-4-methyl-thiazol-5-yl]-phenol | 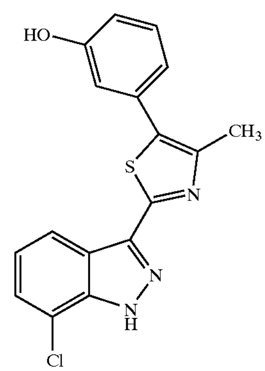 |
| 29. | [2-(1H-Indazol-3-yl)-4-phenyl-thiazol-5-yl]-methanol | 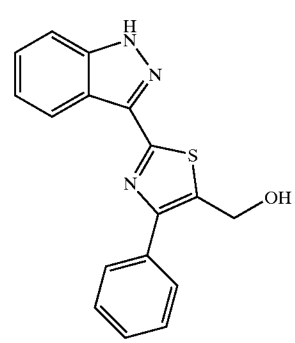 |

TABLE 1-continued

| No. | Name | Structure |
|---|---|---|
| 30. | 3-[5-(4-Bromo-phenyl)-4-methyl-thiazol-2-yl]-1H-indazole | 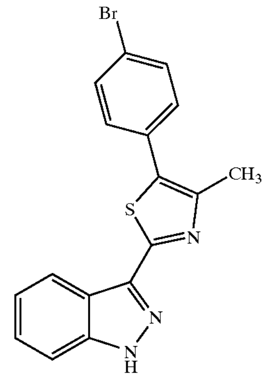 |
| 31. | 2-(1H-Indazol-3-yl)-4-phenyl-thiazole-5-carboxylic acid | 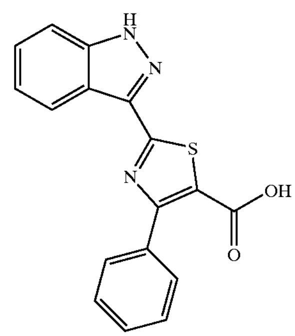 |
| 32. | 4-[2-(1H-Indazol-3-yl)-5-methyl-thiazol-4-yl]-2-methoxy-phenol | 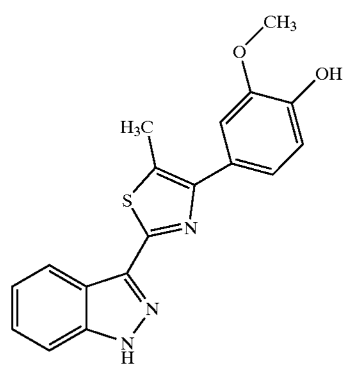 |
| 33. | 3-[4-(6-Bromo-pyridin-3-yl)-5-methyl-thiazol-2-yl]-1H-indazole | 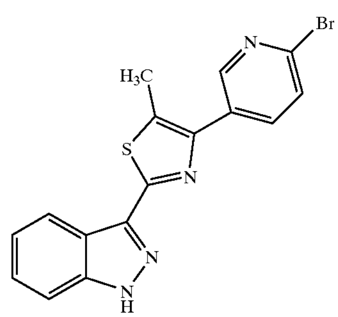 |

TABLE 1-continued

| No. | Name | Structure |
|---|---|---|
| 34. | 3-[4-Methyl-5-(4-morpholin-4-yl-phenyl)-thiazol-2-yl]-1H-indazole | 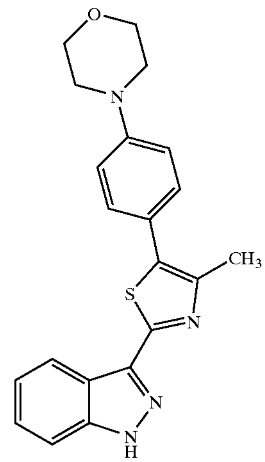 |
| 35. | 3-{4-Methyl-5-[4-(4-methyl-piperazin-1-yl)-phenyl]-thiazol-2-yl)-1H-indazole | 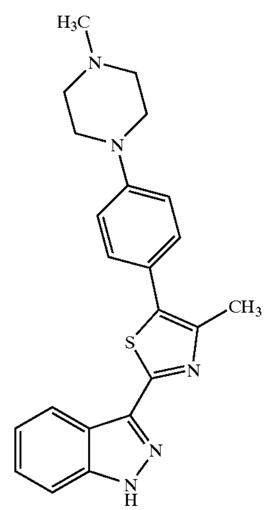 |
| 36. | 3-(5-Methyl-4-(6-morpholin-4-yl-pyridin-3-yl)-thiazol-2-yl]-1H- | 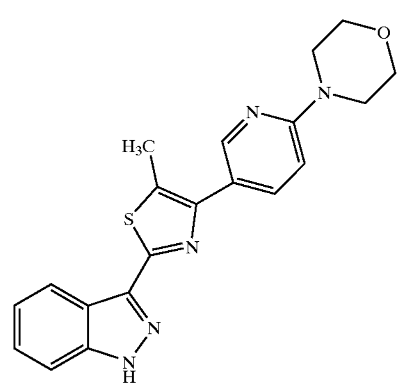 |

TABLE 1-continued

| No. | Name | Structure |
|---|---|---|
| 37. | {4-[2-(1H-Indazol-3-yl)-5-methyl-thiazol-4-yl]-phenyl}-piperazin-1-yl-methanone | 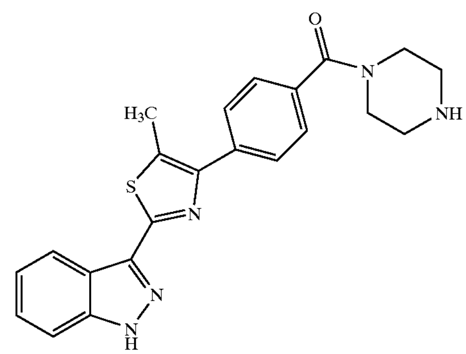 |
| 38. | 3-{5-Methyl-4-[6-(2-morpholin-4-yl-ethoxy)-pyridin-3-yl]-thiazol-2-yl}-1H-indazole | 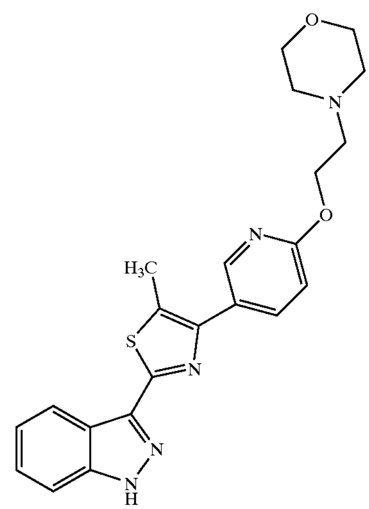 |
| 39. | 3-(5-Methyl-4-pyridin-3-yl-thiazol-2-yl)-1H-indazole | 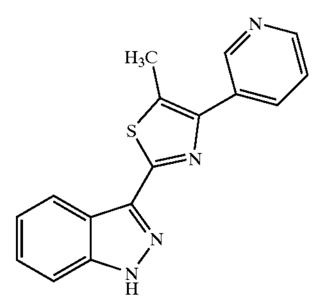 |
| 40. | 3-{4-[6-(3,5-Dimethyl-piperazin-1-yl)-pyridin-3-yl]-5-methyl-thiazol-2-yl}-1H-indazole | 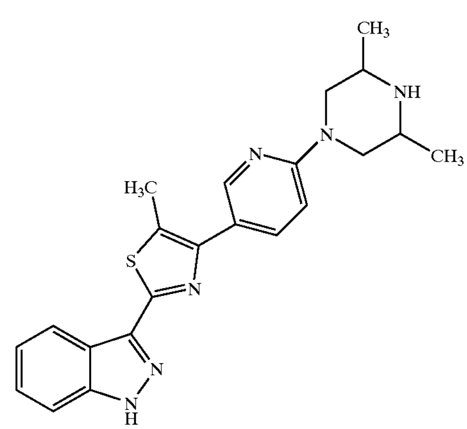 |

TABLE 1-continued
| No. | Name | Structure |
|---|---|---|
| 41. | 3-{4-[6-(4-Cyclopentyl-piperazin-1-yl)-pyridin-3-yl]-5-methyl-thiazol-2-yl}-1H-indazole | 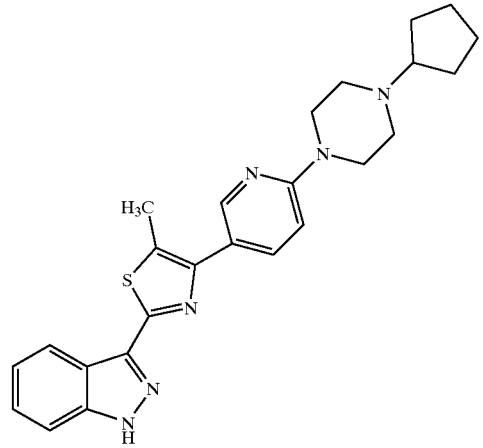 |
| 42. | 3-{4-[6-(4-Isopropyl-piperazin-1-yl)-pyridin-3-yl]-5-methyl-thiazol-2-yl}-1H-indazole | 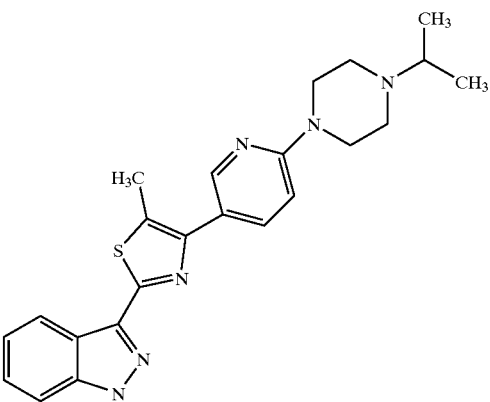 |
| 43. | (2-{5-[2-(1H-Indazol-3-yl)-5-methyl-thiazol-4-yl]-pyridin-2-yloxy}-ethyl)-dimethyl-amine | 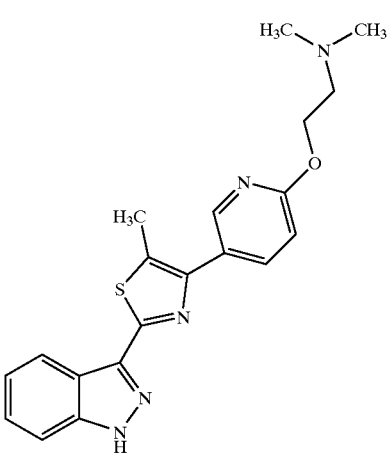 |

TABLE 1-continued

| No. | Name | Structure |
|---|---|---|
| 44. | 3-[5-Methyl-4-(6-piperazin-1-yl-pyridin-3-yl)-thiazol-2-yl]-1H-indazole | 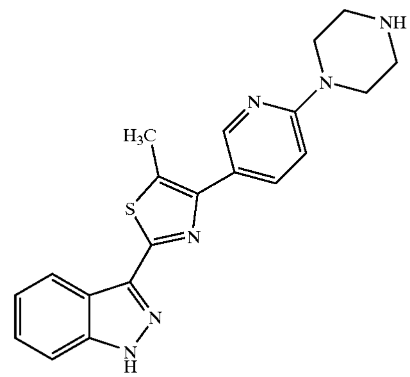 |
| 45. | 1-(4-{5-[2-(1H-Indazol-3-yl)-5-methyl-thiazol-4-yl]-pyridin-2-yl}-piperazin-1-yl)-ethanone | 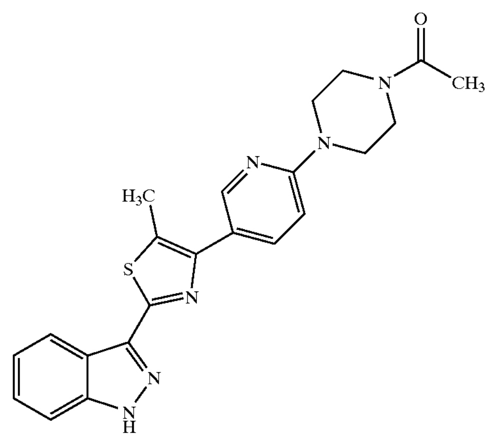 |
| 46. | 3-(4-Ethyl-5-phenyl-thiazol-2-yl)-1H-indazole | 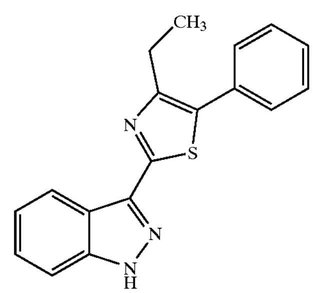 |
| 47. | 1-{5-[2-(1H-Indazol-3-yl)-5-methyl-thiazol-4-yl]-pyridin-2-yl}-pyrrolidin-3-ol | 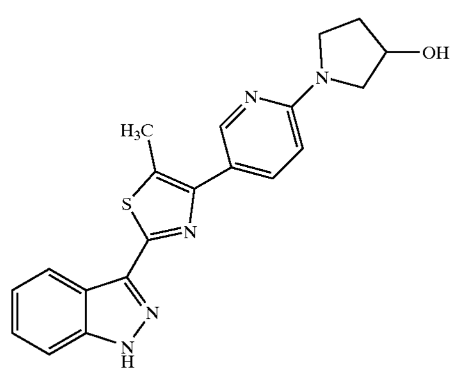 |

TABLE 1-continued

| No. | Name | Structure |
|---|---|---|
| 48. | 3-{5-Methyl-4-[6-(4-methyl-piperazin-1-yl)-pyridin-3-yl]-thiazol-2-yl}-1H-indazole | 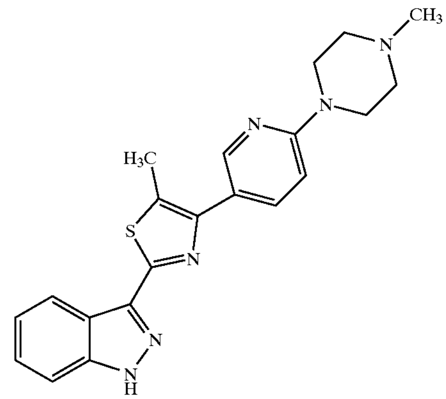 |
| 49. | 2-{5-[2-(1H-Indazol-3-yl)-5-methyl-thiazol-4-yl]-pyridin-2-yloxy}-ethanol | 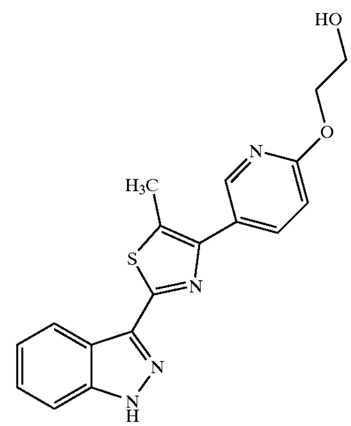 |
| 50. | 3-[5-(6-Chloro-pyridin-3-yl)-4-methyl-thiazol-2-yl]-1H-indazole | 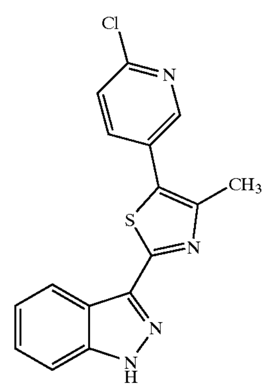 |
| 51. | 3-(4,5-Diphenyl-thiazol-2-yl)-1H-indazole | 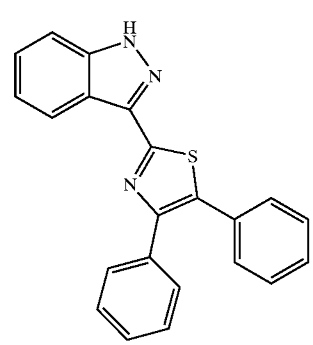 |

TABLE 1-continued

| No. | Name | Structure |
|---|---|---|
| 52. | 2-(1H-Indazol-3-yl)-5-phenyl-thiazole-4-carboxylic acid methyl | 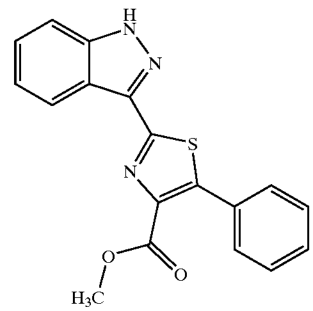 |
| 53. | 3-Diethylamino-1-(4-{5-[2-(1H-indazol-3-yl)-5-methyl-thiazol-4-yl]-pyridin-2-yl}-piperazin-1-yl)-propan-1-one | 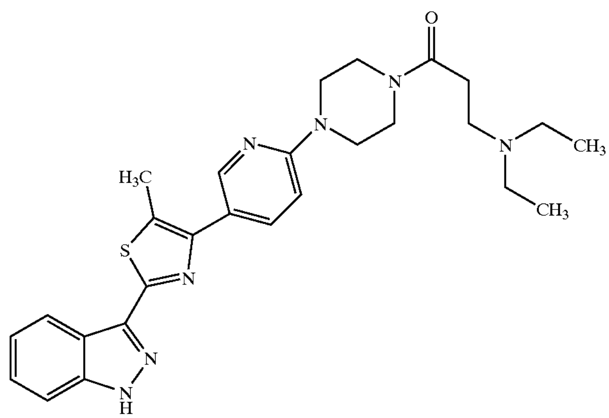 |
| 54. | 3-{4-Methyl-5-[6-(4-methyl-piperazin-1-yl)-pyridin-3-yl]-thiazol-2-yl}-1H-indazole | 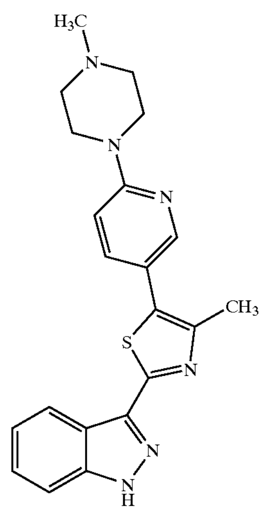 |

TABLE 1-continued

| No. | Name | Structure |
|---|---|---|
| 55. | (2-{5-[2-(1H-Indazol-3-yl)-4-methyl-thiazol-5-yl]-pyridin-2-yloxy}-ethyl)-dimethyl-amine | 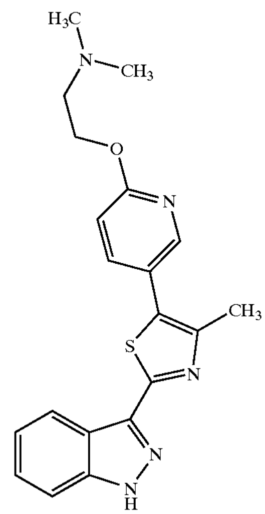 |
| 56. | 5-(2-Hydroxy-phenyl)-2-(1H-indazol-3-yl)-thiazol-4-ol | 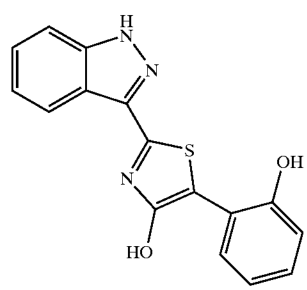 |
| 57. | 2-(1H-Indazol-3-yl)-5-phenyl-thiazole-4-carboxylic acid | 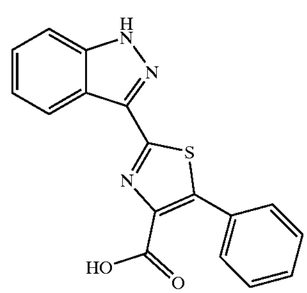 |
| 58. | 3-[5-Methyl-4-(6-piperazin-1-yl-pyridin-3-yl)-thiazol-2-yl]-7-trifluoromethyl-1H-indazole | 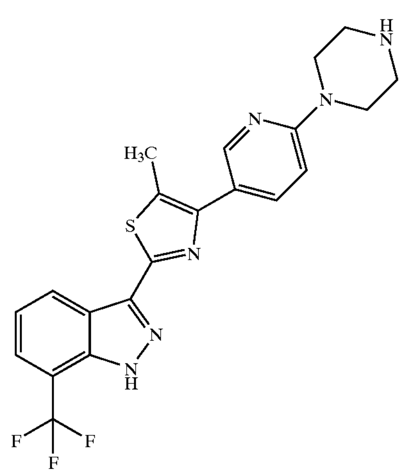 |

TABLE 1-continued

| No. | Name | Structure |
|---|---|---|
| 59. | 2-(1H-Indazol-3-yl)-5-phenyl-thiazole-4-carboxylic acid (2-methoxy-ethyl)-amide | 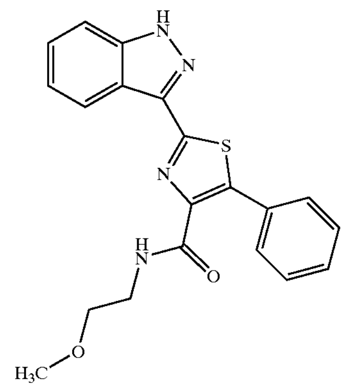 |
| 60. | 2-(1H-Indazol-3-yl)-5-phenyl-thiazole-4-carboxylic acid (2-dimethylamino-ethyl)-amide | 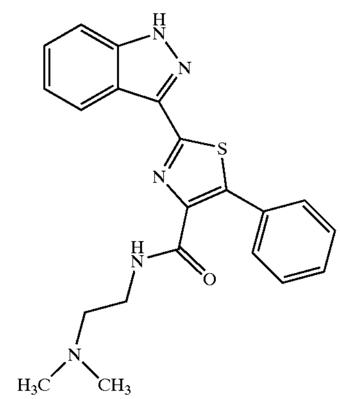 |
| 61. | 2-(1H-Indazol-3-yl)-5-phenyl-thiazole-4-carboxylic acid (2,3-dihydroxy-propyl)-amide | 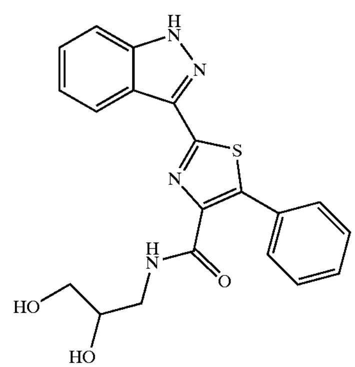 |
| 62. | 2-(1H-Indazol-3-yl)-5-phenyl-thiazole-4-carboxylic acid cyclopropylmethyl-amide | 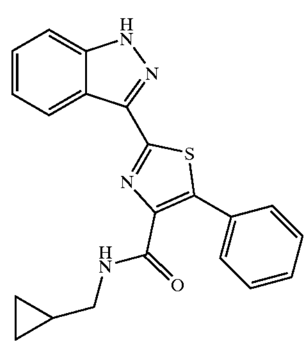 |

TABLE 1-continued

| No. | Name | Structure |
|---|---|---|
| 63. | 3-{4-[6-(3,5-Dimethyl-piperazin-1-yl)-pyridin-3-yl]-5-methyl-thiazol-2-yl}-7-trifluoromethyl-1H-indazole | 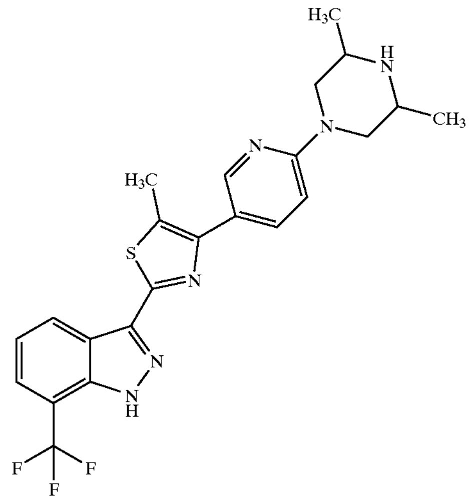 |
| 64. | 2-Dimethylamino-1-(4-{5-[2-(1H-indazol-3-yl)-5-methyl-thiazol-4-yl]-pyridin-2-yl}-piperazin-1-yl)-ethanone | 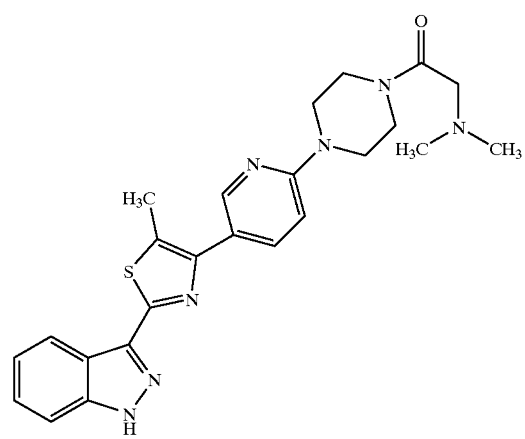 |
| 65. | 2-Bromo-5-[2-(1H-indazol-3-yl)-4-methyl-thiazol-5-yl]-phenol | 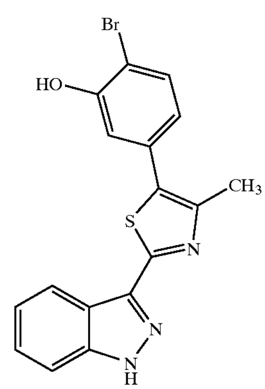 |

TABLE 1-continued

| No. | Name | Structure |
|---|---|---|
| 66. | 2-(7-Methyl-1H-indazol-3-yl)-5-phenyl-thiazole-4-carboxylic acid | 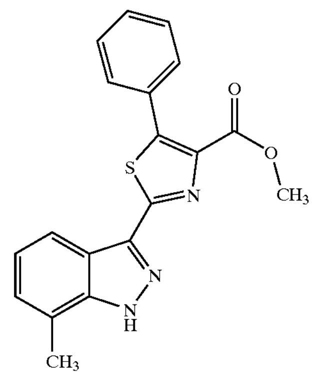 |
| 67. | 2-(7-Chloro-1H-indazol-3-yl)-5-phenyl-thiazole-4-carboxylic acid methyl ester | 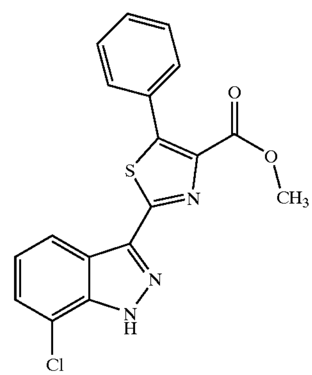 |
| 68. | 7-Methyl-3-[5-methyl-4-(6-piperazin-1-yl-pyridin-3-yl)-thiazol-2-l]-1H-indazole | 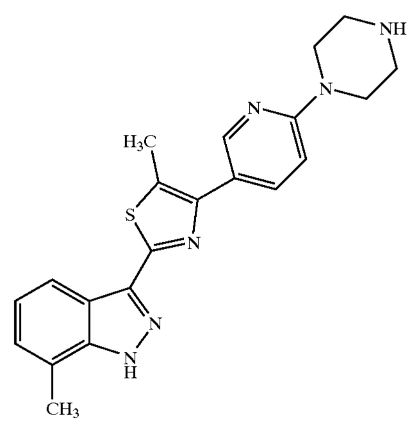 |

TABLE 1-continued

| No. | Name | Structure |
|---|---|---|
| 69. | 3-{4-[6-(3,5-Dimethyl-piperazin-1-yl)-pyridin-3-yl]-5-methyl-thiazol-2-yl}-7-methyl-1H-indazole | 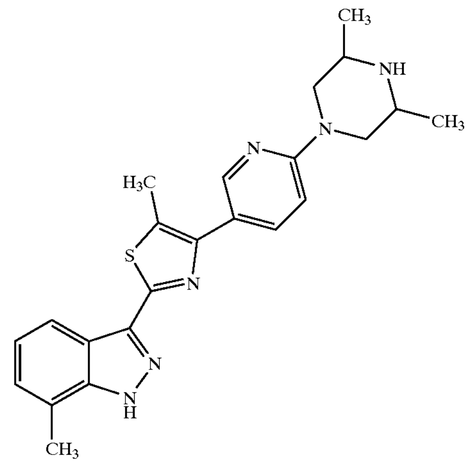 |
| 70. | 2-(7-Ethyl-1H-indazol-3-yl)-5-phenyl-thiazole-4-carboxylic acid methyl ester | 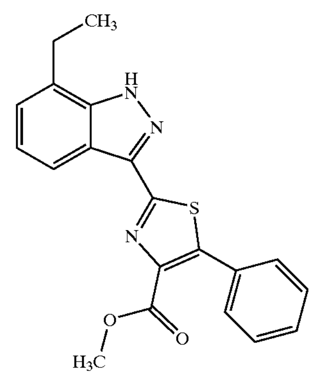 |
| 71. | 2-(7-Methyl-1H-indazol-3-yl)-5-pyridin-3-yl-thiazole-4-carboxylic acid ethyl ester | 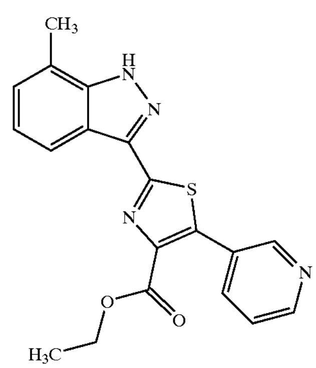 |
| 72. | 2-(7-Methyl-1H-indazol-3-yl)-5-pyridin-3-yl-thiazole-4-carboxylic acid methyl ester | 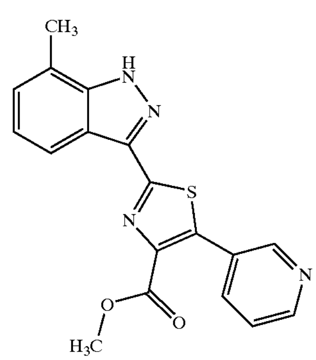 |

TABLE 1-continued

| No. | Name | Structure |
|---|---|---|
| 73. | 4-[2-(1H-Indazol-3-yl)-5-methyl-thiazol-4-yl]-N-pyridin-3-yl-benzamide | 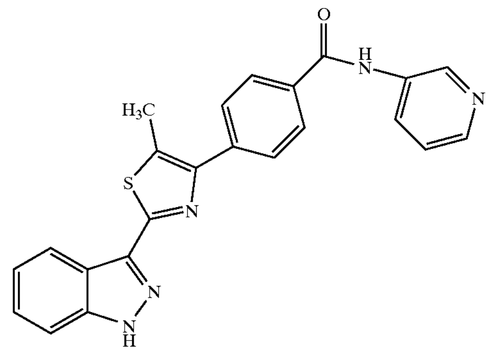 |
| 74. | 2-(7-Methyl-1H-indazol-3-yl)-5-pyridin-3-yl-thiazole-4-carboxylic acid (2-diethylamino-ethyl)-amide | 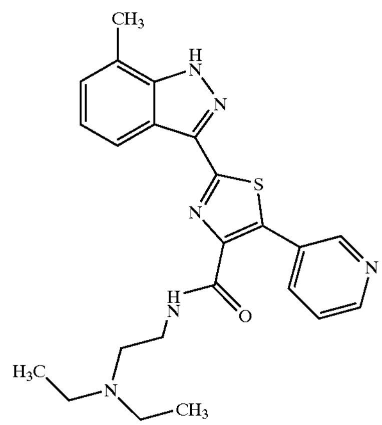 |
| 75. | 2-(7-Methyl-1H-indazol-3-yl)-5-phenyl-thiazole-4-carboxylic acid 2-morpholin-4-yl-ethyl ester | 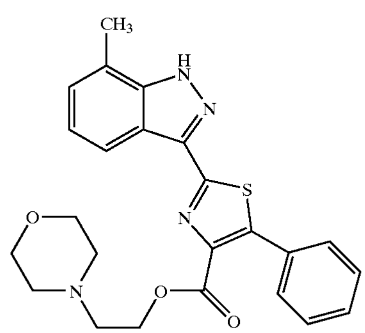 |
| 76. | 2-(7-Methyl-1H-indazol-3-yl)-5-pyridin-3-yl-thiazole-4-carboxylic acid | 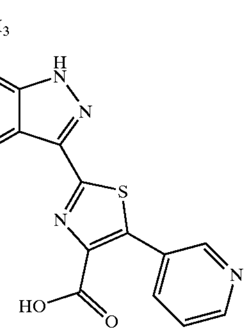 |

TABLE 1-continued
| No. | Name | Structure |
|---|---|---|
| 77. | 2-(7-Methyl-1H-indazol-3-yl)-5-pyridin-3-yl-thiazole-4-carboxylic acid (1-methyl-piperidin-4-yl)-amide | 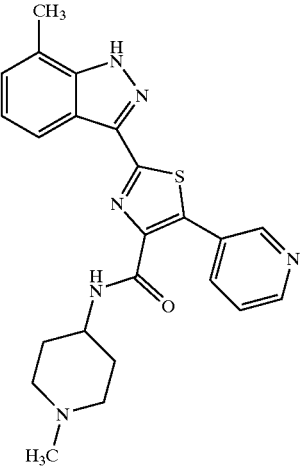 |
| 78. | 2-(7-Methyl-1H-indazol-3-yl)-5-pyridin-3-yl-thiazole-4-carboxylic acid (2-dimethylamino-ethyl)-methyl-amide | 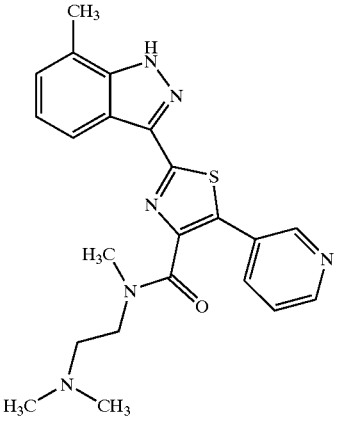 |
| 79. | [2-(7-Methyl-1H-indazol-3-yl)-5-pyridin-3-yl-thiazol-4-yl]-(4-pyridin-4-yl-piperazin-1-yl)-methanone | 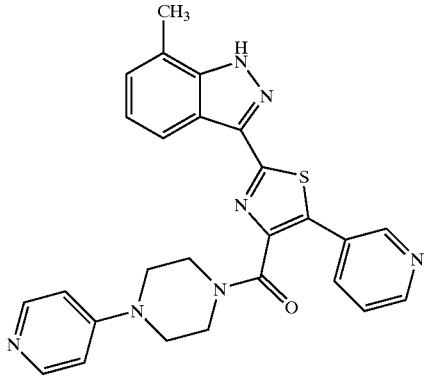 |

TABLE 1-continued

| No. | Name | Structure |
|---|---|---|
| 80. | (3-Dimethylamino-pyrrolidin-1-yl)-[2-(7-methyl-1H-indazol-3-yl)-5-pyridin-3-yl-thiazol-4-yl]-methanone | 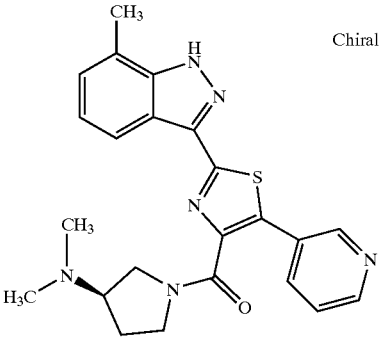 Chiral |
| 81. | (3-Dimethylamino-pyrrolidin-1-yl)-[2-(7-methyl-1H-indazol-3-yl)-5-pyridin-3-yl-thiazol-4-yl]-methanone | 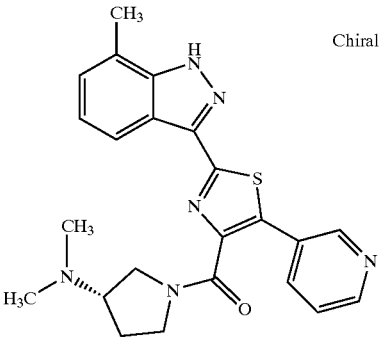 Chiral |
| 82. | [2-(7-Methyl-1H-indazol-3-yl)-5-pyridin-3-yl-thiazol-4-yl]-(4-methyl-piperazin-1-yl)-methanone | 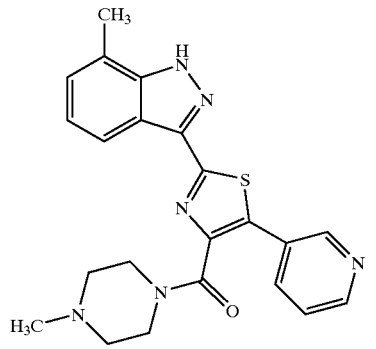 |
| 83. | 5-(6-Chloro-pyridin-3-yl)-2-(7-methyl-1H-indazol-3-yl)-thiazole-4-carboxylic acid methyl ester | 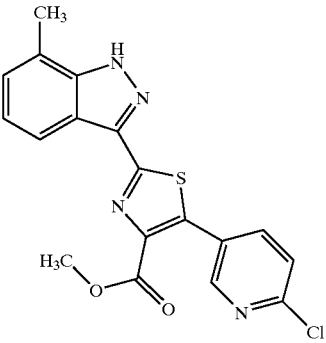 |

TABLE 1-continued
| No. | Name | Structure |
|---|---|---|
| 84. | (3-Hydroxy-pyrrolidin-1-yl)-[2-(7-methyl-1H-indazol-3-yl)-5-pyridin-3-yl-thiazol-4-yl]-methanone | 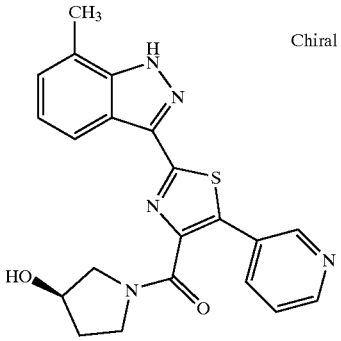 |
| 85. | 2-(7-Methyl-1H-indazol-3-yl)-5-(6-trifluoromethyl-pyridin-3-yl)-thiazole-4-carboxylic acid methyl ester | 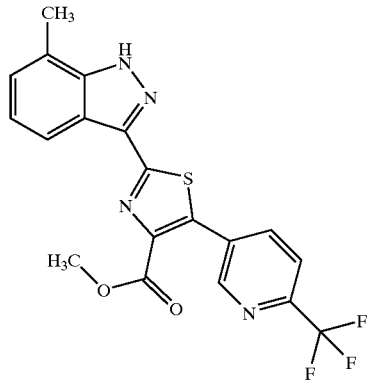 |
| 86. | 2-(7-Methyl-1H-indazol-3-yl)-5-pyridin-3-yl-thiazole-4-carboxylic acid 1-methyl-pyrrolidin-3-yl ester | 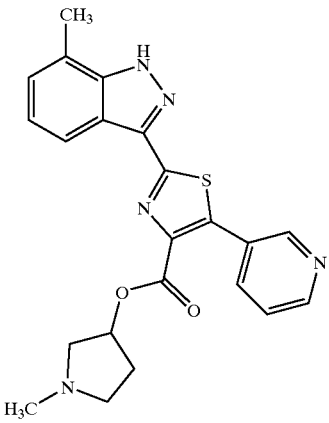 |

TABLE 1-continued

| No. | Name | Structure |
|---|---|---|
| 87. | 2-(7-Methyl-1H-indazol-3-yl)-5-pyridin-3-yi-thiazole-4-carboxylic acid 1-methyl-piperidin-4-yl ester | 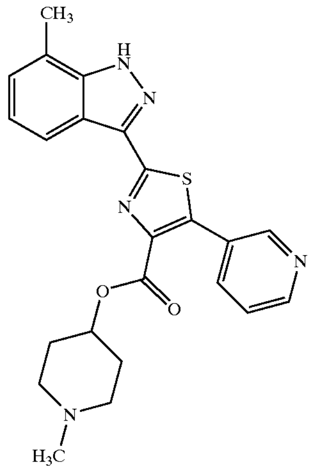 |
| 88. | (3,5-Dimethyl-piperazin-1-yl)-[2-(7-methyl-1H-indazol-3-yl)-5-pyridin-3-yl-thiazol-4-yl]-methanone | 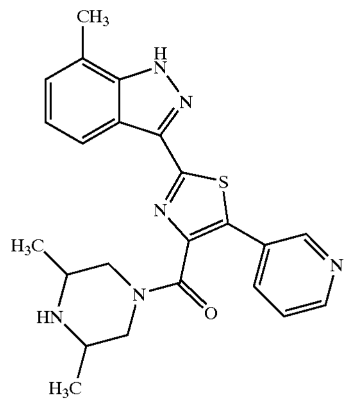 |
| 89. | [5-(6-Chloro-pyridin-3-yl)-2-(7-methyl-1H-indazol-3-yl)-thiazol-4-yl]-(3-hydroxy-pyrrolidin-1-yl)-methanone | Chiral |

TABLE 1-continued
| No. | Name | Structure |
|---|---|---|
| 90. | (3-Hydroxy-pyrrolidin-1-yl)-[2-(7-methyl-1H-indazol-3-yl)-5-(6-morpholin-4-yl-pyridin-3-yl)-thiazol-4-yl]-methanone | 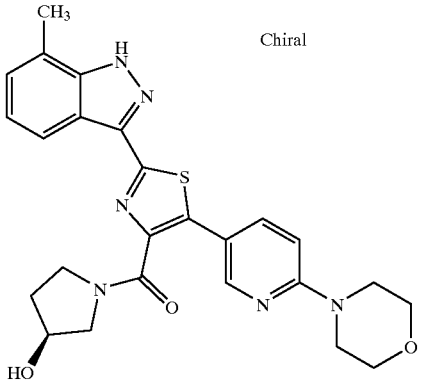 Chiral |
| 91. | [5-[6-(3,5-Dimethyl-piperazin-1-yl)-pyridin-3-yl]-2-(7-methyl-1H-indazol-3-yl)-thiazol-4-yl]-(3-hydroxy-pyrrolidin-1-yl)-methanone | 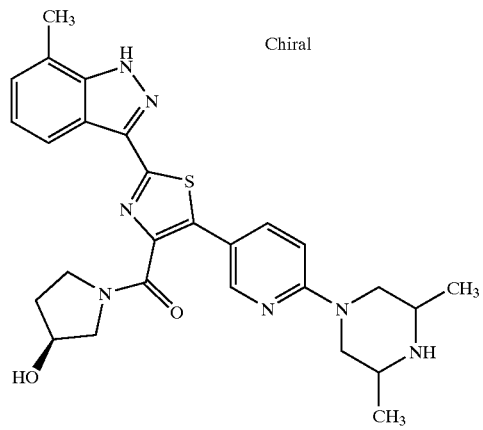 Chiral |
| 92. | (3-Dimethylamino-pyrrolidin-1-yl)-[2-(7-methyl-1H-indazol-3-yl)-5-(6-trifluoromethyl-pyridin-3-yl)-thiazol-4-yl]-methanone | 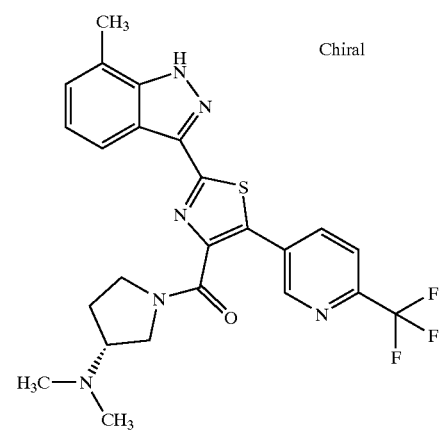 Chiral |

TABLE 1-continued
| No. | Name | Structure |
|-----|------|-----------|
| 93. | [5-(6-Chloropyridin-3-yl)-2-(7-methyl-1H-indazol-3-yl)-thiazol-4-yl]-(3-dimethylamino-pyrrolidin-1-yl)-methanone | 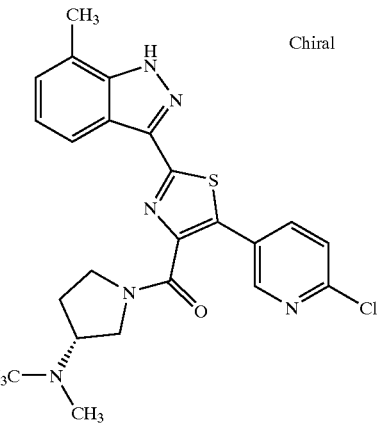 Chiral |
| 94. | [2-(7-Methyl-1H-indazol-3-yl)-5-pyridin-3-yl-thiazol-4-yl]-piperidin-1-yl-methanone | 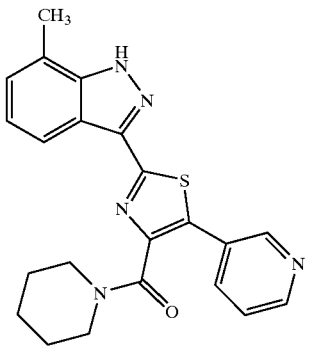 |
| 95. | (3,5-Dimethyl-piperidin-1-yl)-[2-(7-methyl-1H-indazol-3-yl)-5-pyridin-3-yl-thiazol-4-yl]-methanone | 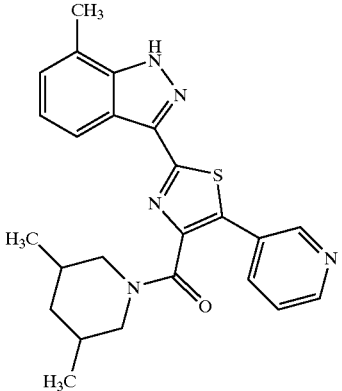 |
| 96. | [2-(7-Methyl-1H-indazol-3-yl)-5-pyridin-3-yl-thiazol-4-yl]-morpholin-4-yl-methanone | 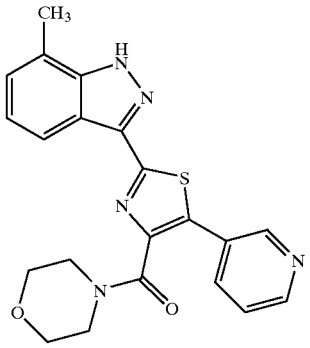 |

TABLE 1-continued

| No. | Name | Structure |
|---|---|---|
| 97. | (3-Dimethylamino-pyrrolidin-1-yl)-[5-(3-methoxy-phenyl)-2-(7-methyl-1H-indazol-3-yl)-thiazol-4-yl]-methanone | 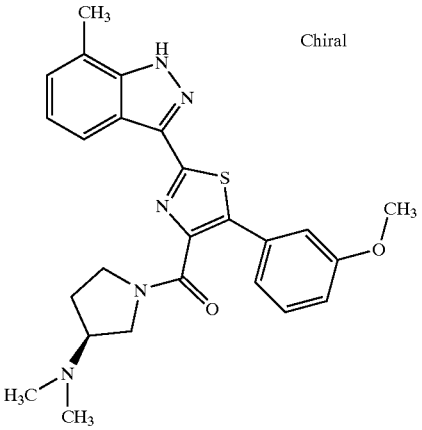 Chiral |
| 98. | 2-(6-Chloro-7-methyl-1H-indazol-3-yl)-5-pyridin-3-yl-thiazole-4-carboxylic acid methyl ester | 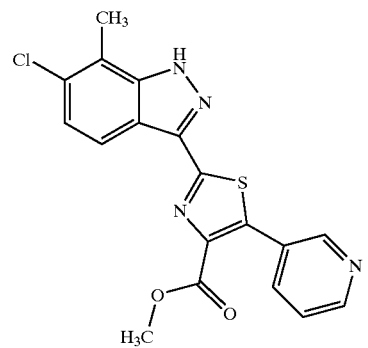 |
| 99. | [2-(6-Chloro-7-methyl-1H-thiazol-[4-yl]-(3-dimethylamino-pyrrolidin-1-yl)-methanone | 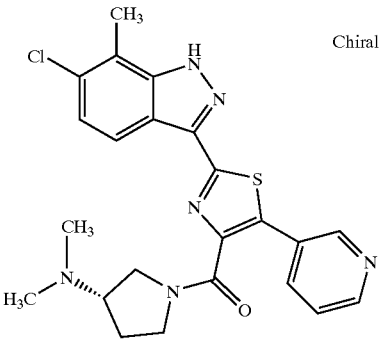 Chiral |
| 100. | [2-(6-Chloro-7-methyl-1H-indazol-3-yl)-5-pyridin-3-yl-thiazol-4-yl]-(3-hydroxy-pyrrolidin-1-yl)-methanone | 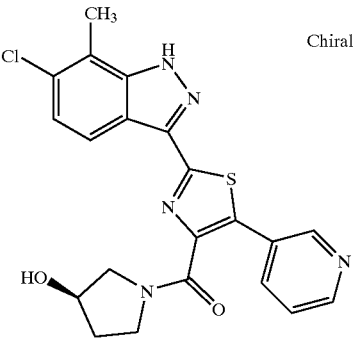 Chiral |

TABLE 1-continued
| No. | Name | Structure |
|---|---|---|
| 101. | [2-(6-Chloro-7-methyl-1H-indazol-3-yl)-5-pyridin-3-yl-thiazol-4-yl]-(4-methyl-piperazin-1-yl)-methanone | 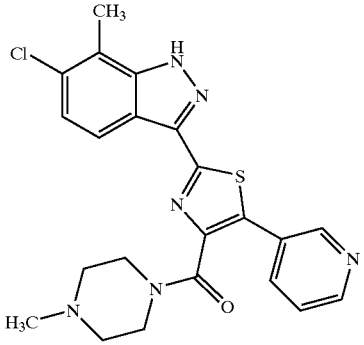 |
| 102. | 2-(7-Methyl-1H-indazol-3-yl)-5-pyridin-3-yl-thiazole-4-carboxylic acid ethyl-methyl-amide | 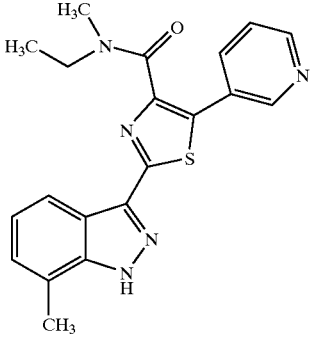 |
| 103. | 5-(4-Fluoro-phenyl)-2-(7-methyl-1H-indazol-3-yl)-thiazole-4-carboxylic acid methyl ester | 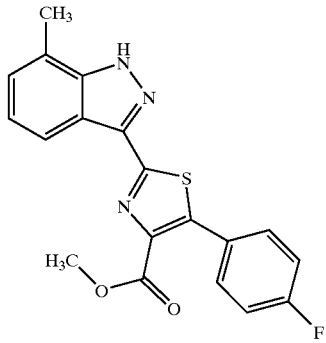 |
| 104. | 5-(4-Hydroxy-phenyl)-2-(7-methyl-1H-indazol-3-yl)-thiazole-4-carboxylic acid methyl ester | 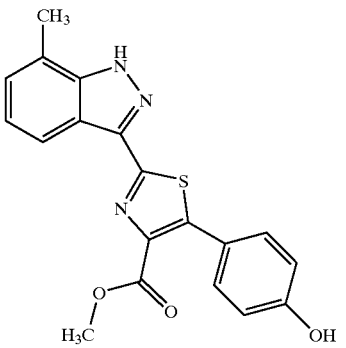 |

TABLE 1-continued

| No. | Name | Structure |
|-----|------|-----------|
| 105. | 2-(4-Chloro-7-methyl-1H-indazol-3-yl)-5-pyridin-3-yl-thiazole-4-carboxylic acid methyl ester | 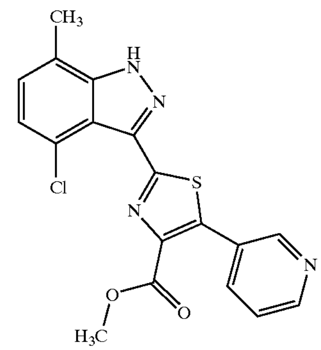 |
| 106. | [5-(4-Fluoro-phenyl)-2-(7-methyl-1H-indazol-3-yl)-thiazol-4-yl]-(4-methyl-piperazin-1-yl)-methanone | 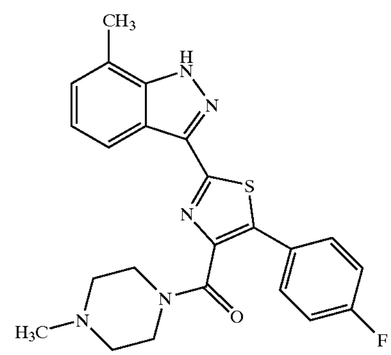 |
| 107. | [5-(4-Fluoro-phenyl)-2-(7-methyl-1H-indazol-3-yl)-thiazol-4-yl]-(3-hydroxy-pyrrolidin-1-yl)-methanone | 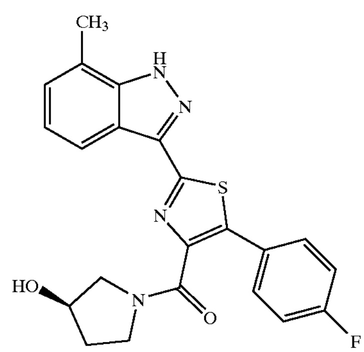 |
| 108. | 5-(3-Fluoro-phenyl)-2-(7-methyl-1H-indazol-3-yl)-thiazole-4-carboxylic acid methyl ester | 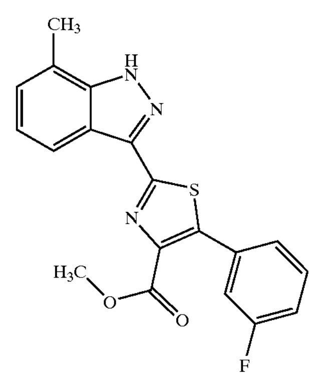 |

TABLE 1-continued

| No. | Name | Structure |
|---|---|---|
| 109. | [5-(3,5-Difluoro-phenyl)-2-(7-methyl-1H-indazol-3-yl)-thiazol-4-yl]-(4-methyl-piperazin-1-yl)-methanone | 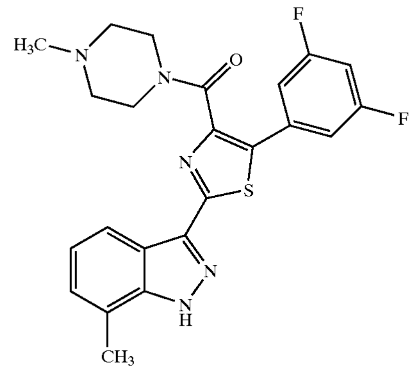 |
| 110. | [5-(3,5-Difluoro-phenyl)-2-(7-methyl-1H-indazol-3-yl)-thiazol-4-yl]-(3-hydroxy-pyrrolidin-1-yl)-methanone | Chiral |
| 111. | (3-Hydroxy-azetidin-1-yl)-[2-(7-methyl-1H-indazol-3-yl)-5-pyridin-3-yl-thiazol-4-yl]-methanone | 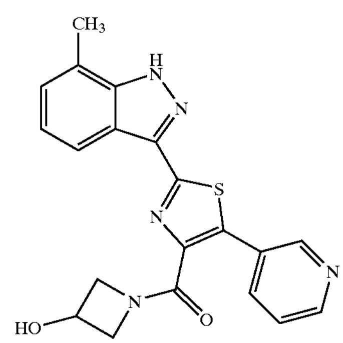 |
| 112. | [5-(3-Fluoro-phenyl)-2-(7-methyl-1H-indazol-3-yl)-thiazol-4-yl]-(4-methyl-piperazin-1-yl)-methanone | 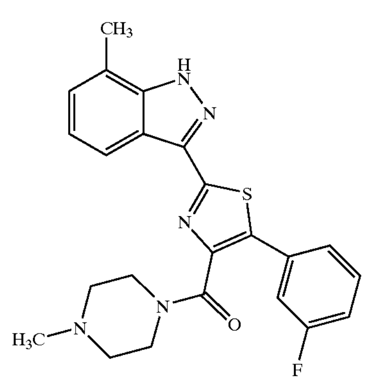 |

TABLE 1-continued

| No. | Name | Structure |
|---|---|---|
| 113. | (3-Dimethylamino-pyrrolidin-1-yl)-[5-(4-hydroxy-phenyl)-2-(7-methyl-1H-indazol-3-yl)-thiazol-4-yl]-methanone | 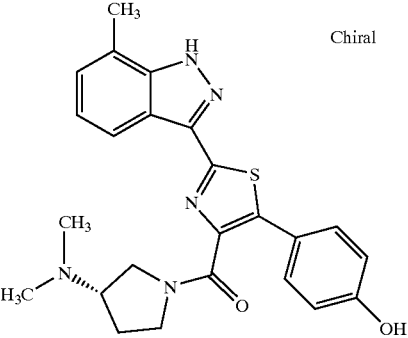 Chiral |
| 114. | [5-(3,4-Difluoro-phenyl)-2-(7-methyl-1H-indazol-3-yl)-thiazol-4-yl]-(4-methyl-piperazin-1-yl)-methanone | 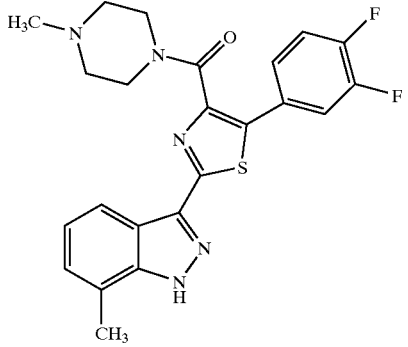 |
| 115. | [5-(3,4-Difluoro-phenyl)-2-(7-methyl-1H-indazol-3-yl)-thiazol-4-yl]-(3-hydroxy-pyrrolidin-1-yl)-methanone | 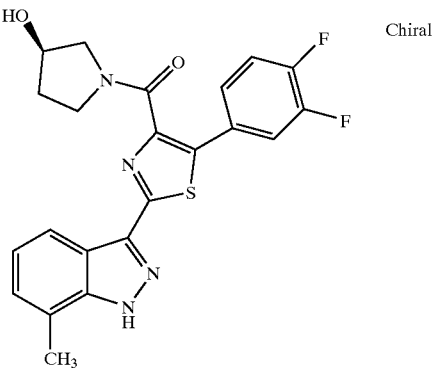 Chiral |
| 116. | [5-(3,4-Difluoro-phenyl)-2-(7-methyl-1H-indazol-3-yl)-thiazol-4-yl]-(3-dimethylamino-pyrrolidin-1-yl)-methanone | 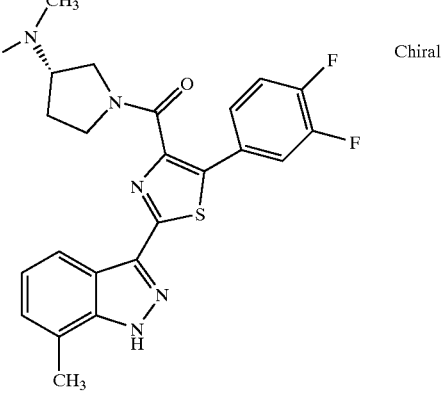 Chiral |

TABLE 1-continued

| No. | Name | Structure |
|---|---|---|
| 117. | [5-(4-Fluoro-3-hydroxy-phenyl)-2-(7-methyl-1H-indazol-3-yl)-thiazol-4-yl]-(4-methyl-piperazin-1-yl)-methanone | 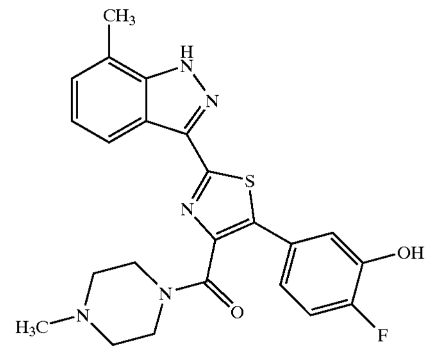 |
| 118. | [2-(6-Chloro-7-methyl-1H-indazol-3-yl)-5-pyridin-3-yl-thiazol-4-yl]-(3-hydroxy-azetidin-1-yl)-methanone | 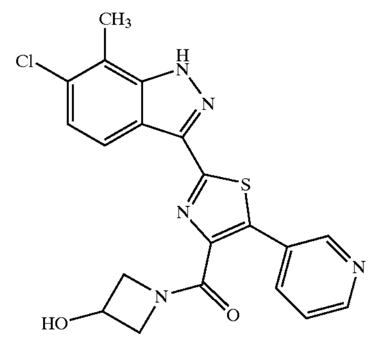 |
| 119. | [2-(6-Chloro-7-methyl-1H-indazol-3-yl )-5-pyridin-3-yl-thiazol-4-yl]-(4-pyridin-4-yl-piperazin-1-yl)-methanone | 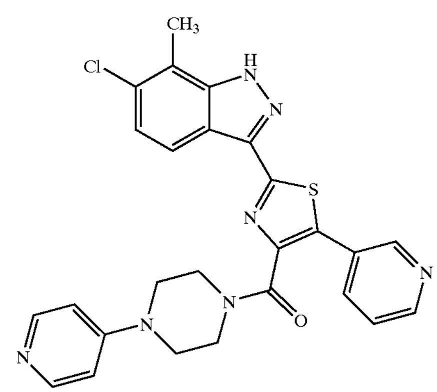 |
| 120. | 2-(6-Chloro-7-methyl-1H-indazol-3-yl)-5-pyridin-3-yl-thiazole-4-carboxylic acid (2-diethylamino-ethyl)-amide | 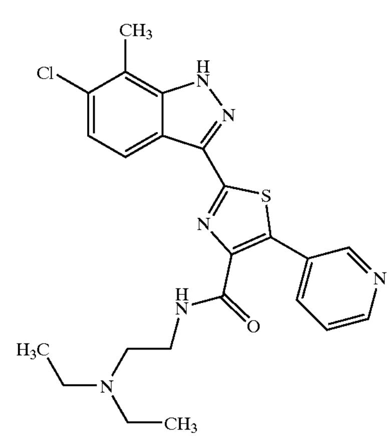 |

TABLE 1-continued

| No. | Name | Structure |
|-----|------|-----------|
| 121. | [2-(6-Fluoro-7-methyl-1H-indazol-3-yl)-5-pyridin-3-yl-thiazol-4-yl]-(4-methyl-piperazin-1-yl)-methanone | 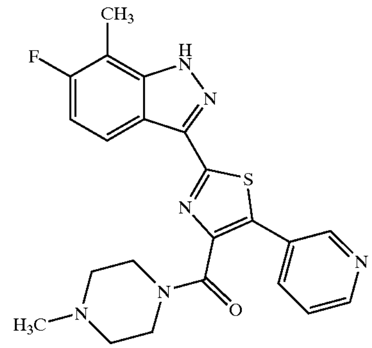 |
| 122. | [5-(6-Methoxy-pyridin-3-yl)-2-(7-methyl-1H-indazol-3-yl)-thiazol-4-yl]-(4-methyl-piperazin-1-yl)-methanone | 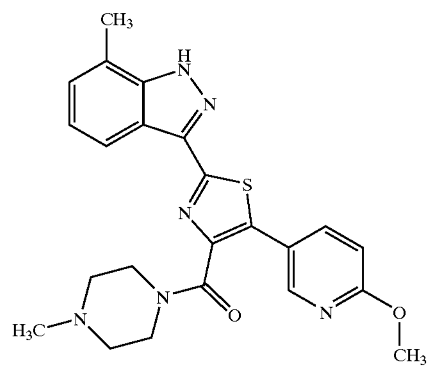 |
| 123. | [2-(6-Chloro-7-methyl-1H-indazol-3-yl)-5-pyridin-3-yl-thiazol-4-yl]-piperazin-1-yl-methanone | 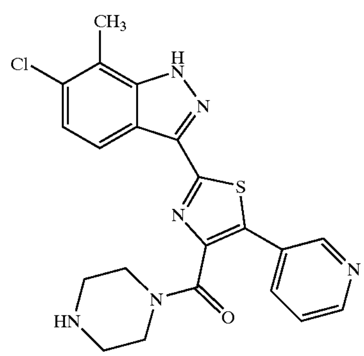 |
| 124. | [2-(6-Chloro-7-methyl-1H-indazol-3-yl)-5-pyridin-3-yl-thiazol-4-yl]-(3-hydroxy-pyrrolidin-1-yl)-methanone | Chiral |

TABLE 1-continued

| No. | Name | Structure |
|---|---|---|
| 125. | 2-(6-Chloro-7-methyl-1H-indazol-3-yl)-5-pyridin-3-yl-thiazole-4-carboxylic acid methyl-(1-methyl-pyrrolidin-3-ylmethyl)-amide | 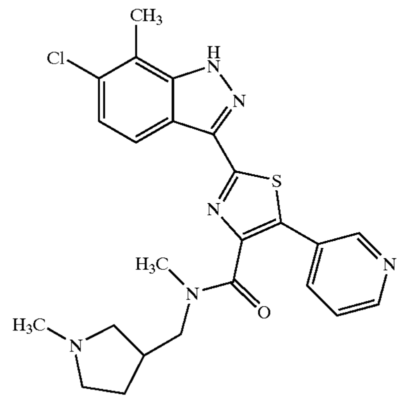 |
| 126. | [2-(7-Ethyl-1H-indazol-3-yl)-5-pyridin-3-yl-thiazol-4-yl]-(4-methyl-piperazin-1-yl)-methanone | 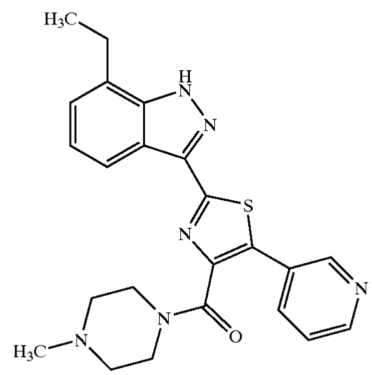 |
| 127. | (3-Dimethylamino-pyrrolidin-1-yl)-[2-(7-ethyl-1H-indazol-3-yl)-5-pyridin-3-yl-thiazol-4-yl]-methanone | Chiral |
| 128. | [2-(6-Chloro-7-methyl-1H-indazol-3-yl)-5-pyridin-3-yl-thiazol-4-yl]-(4-pyridin-2-yl-piperazin-1-yl)-methanone | 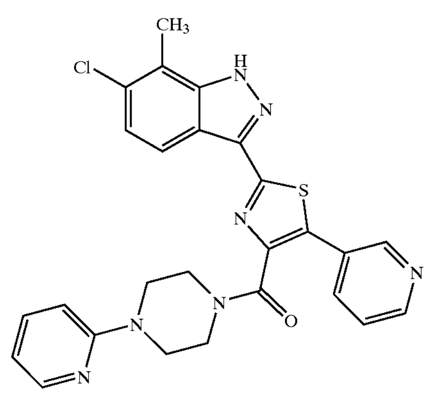 |

TABLE 1-continued

| No. | Name | Structure |
|---|---|---|
| 129. | [2-(6-Chloro-7-methyl-1H-indazol-3-yl)-5-pyridin-3-yl-thiazol-4-yl]-(4-pyridin-2-ylmethyl-piperazin-1-yl)-methanone | 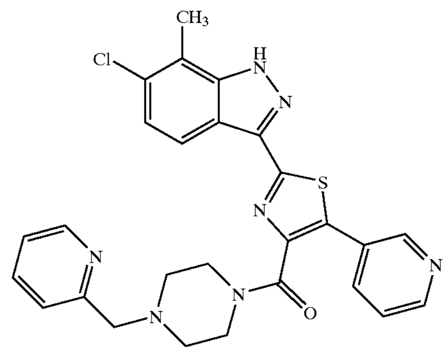 |
| 130. | [2-(6-Chloro-7-methyl-1H-indazol-3-yl)-5-pyridin-3-yl-thiazol-4-yl]-[4-(2-hydroxy-ethyl)-piperazin-1-yl]-methanone | 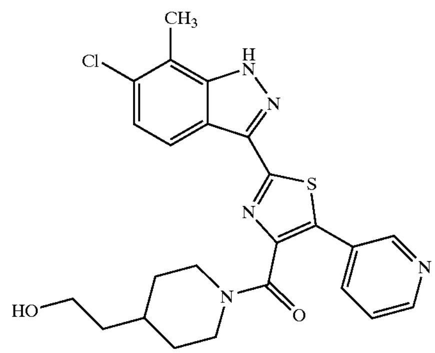 |
| 131. | 2-(6-Chloro-7-methyl-1H-indazol-3-yl)-5-pyridin-3-yl-thiazole-4-carboxylic acid (1-methyl-piperidin-4-yl)-amide | 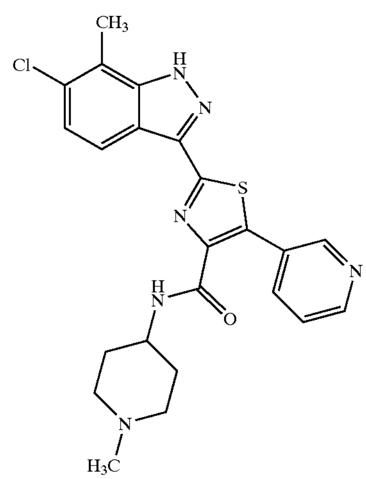 |
| 132. | [2-(6-Chloro-7-methyl-1H-indazol-3-yl)-5-pyridin-3-yl-thiazol-4-yl]-(2,3,5,6-tetrahydro-[1,2']bipyrazinyl-4-yl)-methanone | 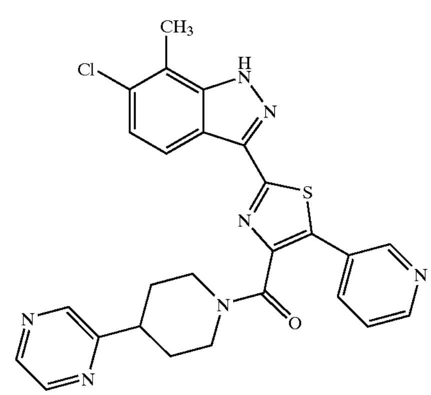 |

TABLE 1-continued
| No. | Name | Structure |
|---|---|---|
| 133. | [2-(6-Chloro-7-methyl-1H-indazol-3-yl)-5-pyridin-3-yl-thiazol-4-yl]-(4-pyrimidin-2-yl-piperazin-1-yl)-methanone | 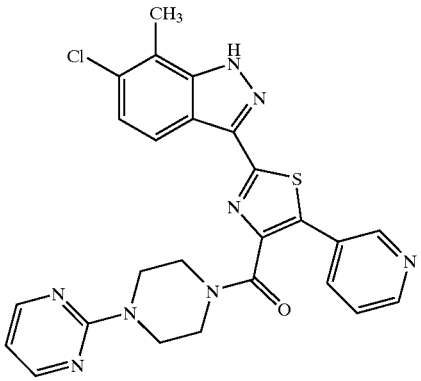 |
| 134. | [2-(6-Chloro-7-methyl-1H-indazol-3-yl)-5-pyridin-3-yl-thiazol-4-yl]-[3-(ethyl-methyl-amino)-azetidin-1-yl]-methanone | 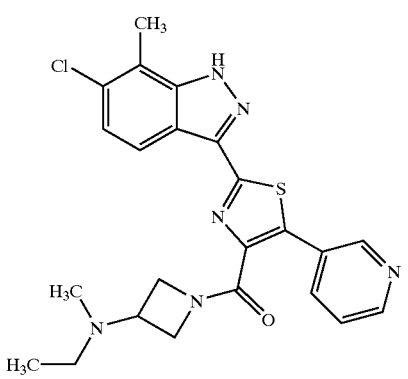 |
| 135. | 2-(6-Chloro-7-methyl-1H-indazol-3-yl)-5-pyridin-3-yl-thiazole-4-carboxylic acid methyl-(2-methylamino-ethyl)-amide | 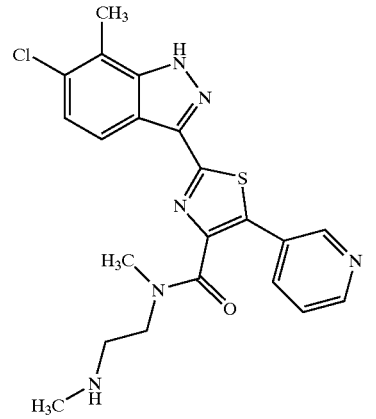 |

TABLE 1-continued

| No. | Name | Structure |
|---|---|---|
| 136. | 2-(6-Chloro-7-methyl-1H-indazol-3-yl)-5-pyridin-3-yl-thiazole-4-carboxylic acid (2-dimethylamino-1-methyl-ethyl)-amide | 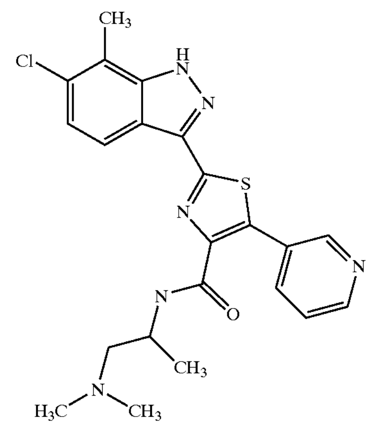 |
| 137. | 2-(6-Chloro-7-methyl-1H-indazol-3-yl)-5-pyridin-3-yl-thiazole-4-carboxylic acid (2-pyrrolidin-1-yl-ethyl)-amide | 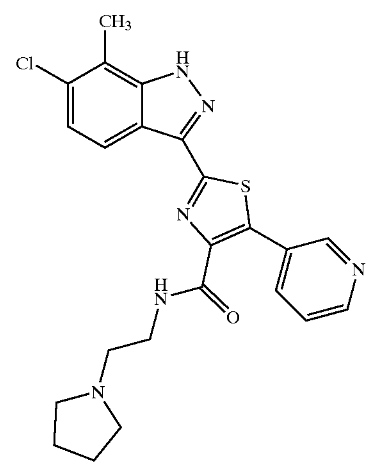 |
| 138. | [2-(6-Chloro-7-methyl-1H-indazol-3-yl)-5-pyridin-3-yl-thiazol-4-yl]-(4-isopropyl-piperazin-1-yl)-methanone | 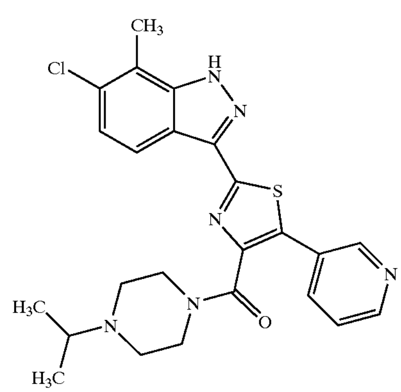 |

TABLE 1-continued

| No. | Name | Structure |
|---|---|---|
| 139. | 2-(6-Chloro-7-methyl-1H-indazol-3-yl)-5-pyridin-3-yl-thiazole-4-carboxylic acid (2-morpholin-4-yl-ethyl)-amide | 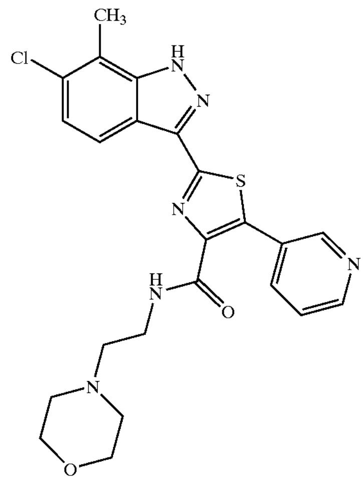 |
| 140. | 2-(6-Chloro-7-methyl-1H-indazol-3-yl)-5-pyridin-3-yl-thiazole-4-carboxylic acid [2-(1-methyl-pyrrolidin-2-yl)-ethyl]-amide | 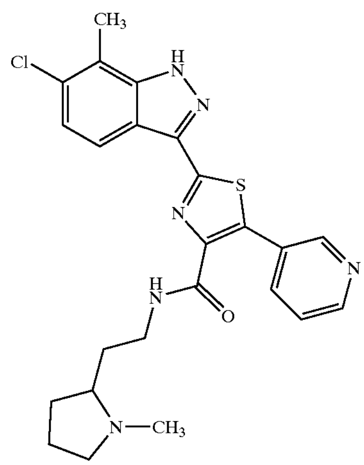 |
| 141. | 2-(6-Chloro-7-methyl-1H-indazol-3-yl)-5-pyridin-3-yl-thiazole-4-carboxylic acid (2-dimethylamino-ethyl)-methyl-amide | 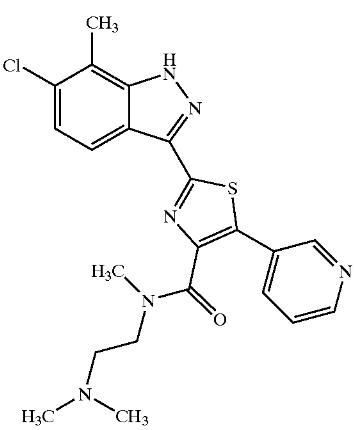 |

TABLE 1-continued

| No. | Name |
|---|---|
| 142. | [2-(6-Chloro-7-methyl-1H-indazol-3-yl)-5-pyridin-3-yl-thiazol-4-yl]-[4-(2-diethylamino-ethyl)-piperazin-1-yl]-methanone |
| 143. | 2-(6-Chloro-7-methyl-1H-indazol-3-yl)-5-pyridin-3-yl-thiazole-4-carboxylic acid [3-(5-oxo-4,5-dihydro-1H-pyrazol-4-yl)-propyl]-amide |
| 144. | [2-(6-Chloro-7-methyl-1H-indazol-3-yl)-5-pyridin-3-yl-thiazol-4-yl]-(3-methylamino-pyrrolidin-1-yl)-methanone |
| 145. | [2-(6-Chloro-7-methyl-1H-indazol-3-yl)-5-pyridin-3-yl-thiazol-4-yl]-(4-pyridin-4-ylmethyl-piperazin-1-yl)-methanone |

TABLE 1-continued

| No. | Name |
|---|---|
| 146. | [2-(7-Methyl-1H-indazol-3-yl)-5-pyridin-3-yl-thiazol-4-yl]-(4-pyridin-4-ylmethyl-piperazin-1-yl)-methanone |
| 147. | 2-(4,7-Dimethyl-1H-indazol-3-yl)-5-pyridin-3-yl-thiazole-4-carboxylic acid methyl ester |
| 148. | 2-(4,7-Dimethyl-1H-indazol-3-yl)-5-pyridin-3-yl-thiazole-4-carboxylic acid ethyl ester |
| 149. | [2-(4,7-Dimethyl-1H-indazol-3-yl)-5-pyridin-3-yl-thiazol-4-yl]-(4-methyl-piperazin-1-yl)-methanone |

TABLE 1-continued

| No. | Name | Structure |
|---|---|---|
| 150. | 2-(6-Methyl-1H-indazol-3-yl)-5-pyridin-3-yl-thiazole-4-carboxylic acid methyl ester | 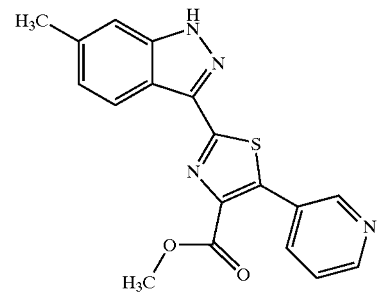 |
| 151. | 2-(4-Fluoro-7-methyl-1H-indazol-3-yl)-5-pyridin-3-yl-thiazole-4-carboxylic acid methyl ester | 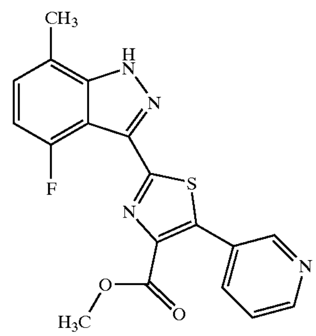 |
| 152. | 2-(6-Fluoro-7-methyl-1H-indazol-3-yl)-5-pyridin-3-yl-thiazole-4-carboxylic acid methyl-(2-methylamino-ethyl)-amide | 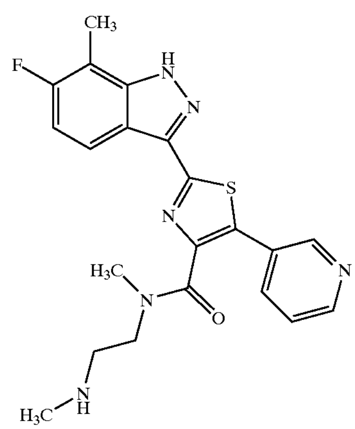 |
| 153. | [2-(6-Fluoro-7-methyl-1H-indazol-3-yl)-5-pyridin-3-yl-thiazol-4-yl]-piperazin-1-yl-methanone | 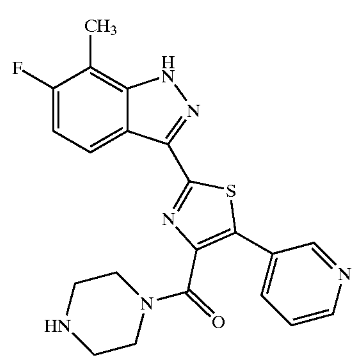 |

TABLE 1-continued

| No. | Name | Structure |
|---|---|---|
| 154. | (3-Dimethylamino-pyrrolidin-1-yl)-[2-(6-methyl-1H-indazol-3-yl)-5-pyridin-3-yl-thiazol-4-yl]-methanone | 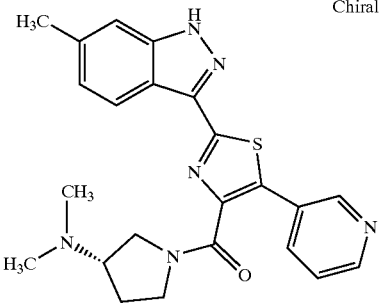 Chiral |
| 155. | (3-Dimethylamino-pyrrolidin-1-yl)-[2-(4-fluoro-7-methyl-1H-indazol-3-yl)-5-pyridin-3-yl-thiazol-4-yl]-methanone | 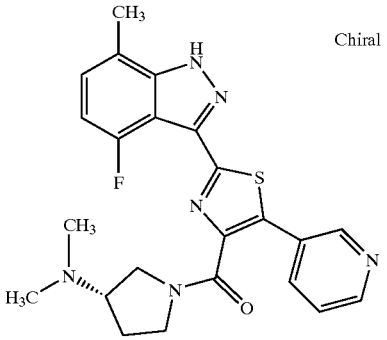 Chiral |
| 156. | [2-(6-Chloro-1H-indazol-3-yl)-5-pyridin-3-yl-thiazol-4-yl]-piperazin-1-yl-methanone | 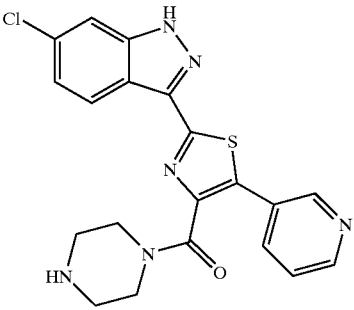 |
| 157 | [2-(6-Chloro-7-methyl-1H-indazol-3-yl)-5-pyridin-3-yl-thiazol-4-yl]-[3-(4-methyl-piperazin-1-yl)-azetidin-1-yl]-methanone | 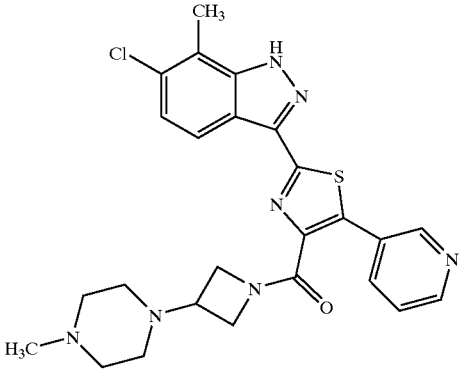 |

TABLE 1-continued

| No. | Name | Structure |
|---|---|---|
| 158. | [2-(7-Methyl-1H-indazol-3-yl)-5-pyridin-3-yl-thiazol-4-yl]-piperazin-1-yl-methanone | 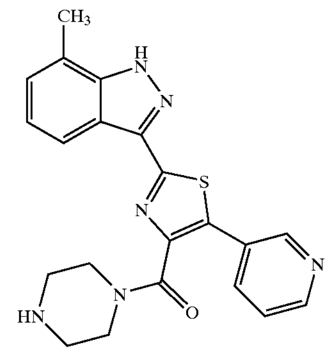 |
| 159. | (3-Dimethylamino-pyrrolidin-1-yl)-[2-(6-fluoro-7-methyl-1H-indazol-3-yl)-5-pyridin-3-yl-thiazol-4-yl]-methanone | Chiral |
| 160. | [1,4]Diazepan-1-yl-[2-(7-methyl-1H-indazol-3-yl)-5-pyridin-3-yl-thiazol-4-yl]-methanone | 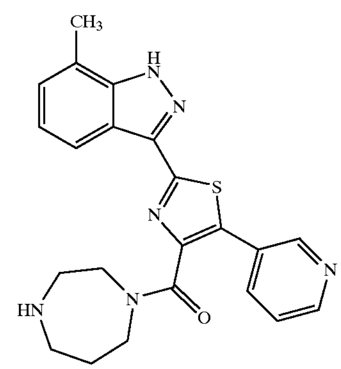 |
| 161. | (2,5-Diaza-bicyclo[2.2.1]hept-2-yl)-[2-(7-methyl-1H-indazol-3-yl)-5-pyridin-3-yl-thiazol-4-yl]-methanone | 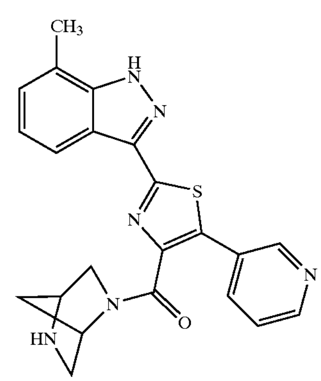 |

TABLE 1-continued

| No. | Name | Structure |
|---|---|---|
| 162. | [2-(7-Methyl-1H-indazol-3-yl)-5-pyridin-3-yl-thiazol-4-yl]-(4-morpholin-4-yl-piperidin-1-yl)-methanone | 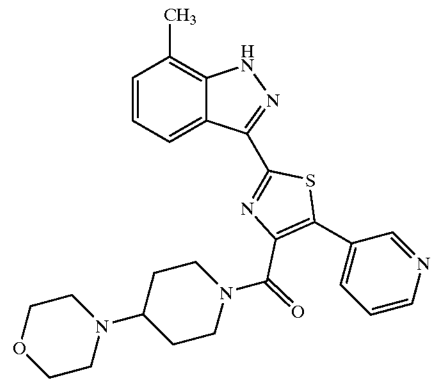 |
| 163. | [1,4']Bipiperidinyl-1'-yl-[2-(7-methyl-1H-indazol-3-yl)-5-pyridin-3-yl-thiazol-4-yl]-methanone | 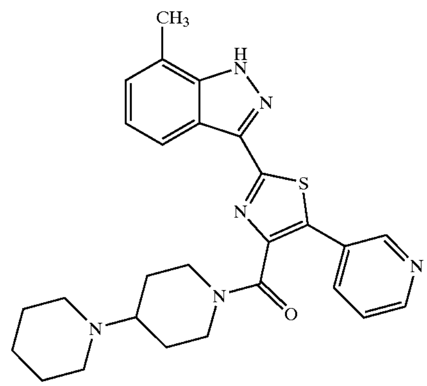 |
| 164. | [2-(7-Methyl-1H-indazol-3-yl)-5-pyridin-3-yl-thiazol-4-yl]-(4-pyrrolidin-1-yl-piperidin-1-yl)-methanone | 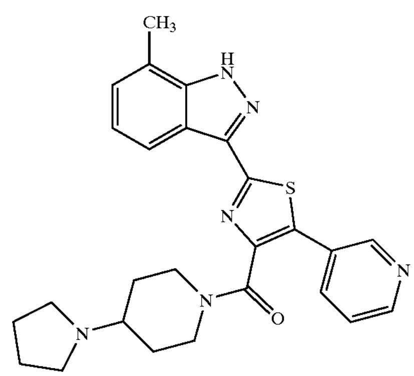 |
| 165. | (3-Dimethylamino-pyrrolidin-1-yl)-[2-(4,7-dimethyl-1H-indazol-3-yl)-5-pyridin-3-yl-thiazol-4-yl]-methanone | Chiral |

TABLE 1-continued

| No. | Name | Structure |
|---|---|---|
| 166. | (3-Dimethylamino-pyrrolidin-1-yl)-[2-(5,7-dimethyl-1H-indazol-3-yl)-5-pyridin-3-yl-thiazol-4-yl]-methanone | 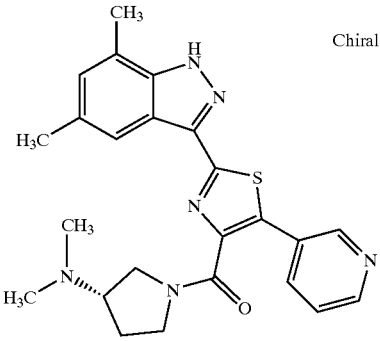 Chiral |
| 167. | [2-(5,7-Dimethyl-1H-indazol-3-yl)-5-pyridin-3-yl-thiazol-4-yl]-(4-methyl-piperazin-1-yl)-methanone | 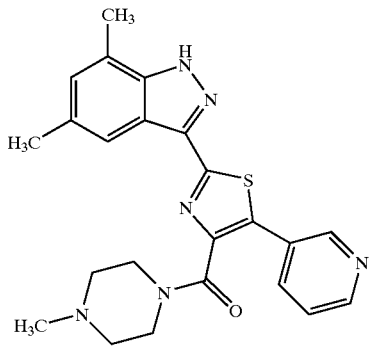 |
| 168. | [2-(5,7-Dimethyl-1H-indazol-3-yl)-5-pyridin-3-yl-thiazol-4-yl]-piperazin-1-yl-methanone | 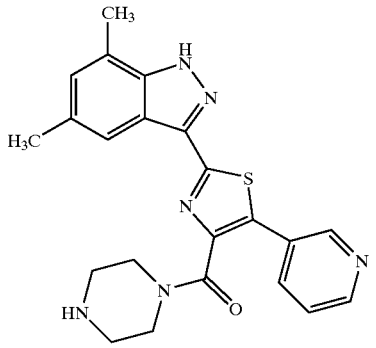 |
| 169. | (3-Dimethylamino-pyrrolidin-1-yl)-[2-(7-methyl-1H-indazol-3-yl)-5-(6-methyl-pyridin-3-yl)-thiazol-4-yl]-methanone | 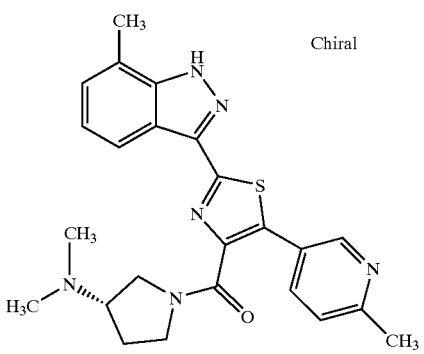 Chiral |

TABLE 1-continued

| No. | Name | Structure |
|---|---|---|
| 170. | (3-Dimethylamino-pyrrolidin-1-yl)-[2-(5-fluoro-7-methyl-1H-indazol-3-yl-5-pyridin-3-yl-thiazol-4-yl]-methanone | 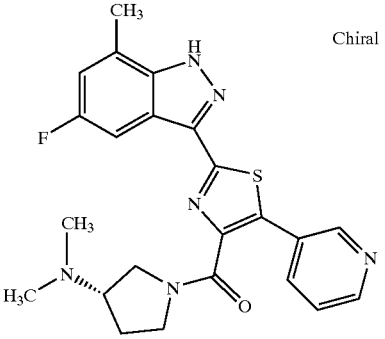 Chiral |
| 171. | 2-(7-Methyl-1H-indazol-3-yl)-5-pyridin-4-yl-thiazole-4-carboxylic acid ethyl ester | 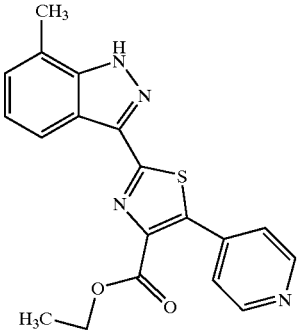 |
| 172. | (4-Dimethylamino-piperidin-1-yl)-[2-(7-methyl-1H-indazol-3-yl)-5-pyridin-3-yl-thiazol-4-yl]-methanone | 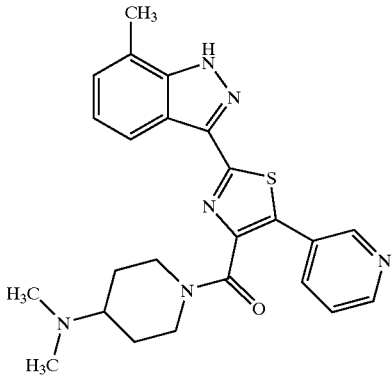 |
| 173. | (4-Dimethylamino-piperidin-1-yl)-[2-(5,7-dimethyl-1H-indazol-3-yl)-5-pyridin-3-yl-thiazol-4-yl]-methanone | 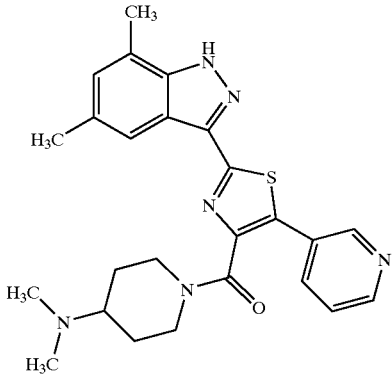 |

TABLE 1-continued
| No. | Name | Structure |
|---|---|---|
| 174. | 2-(5,7-Dimethyl-1H-indazol-3-yl)-5-pyridin-3-yl-thiazole-4-carboxylic acid methyl-(2-methylamino-ethyl)-amide | 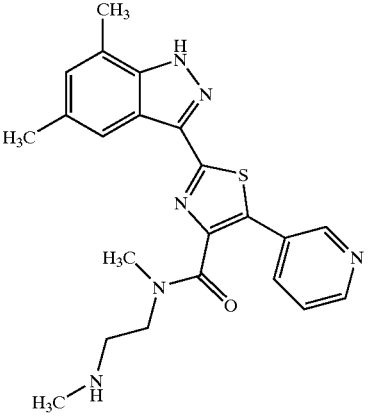 |
| 175. | 2-(5,7-Dimethyl-1H-indazol-3-yl)-5-pyridin-3-yl-thiazole-4-carboxylic acid (2-dimethylamino-ethyl)-methyl-amide | 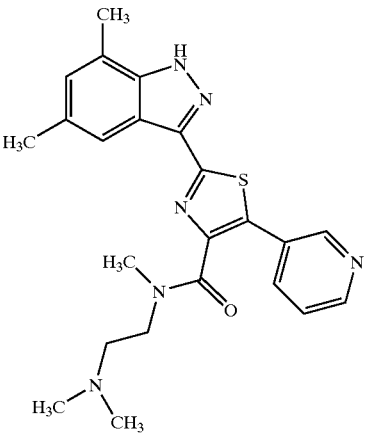 |
| 176. | [2-(5,7-Dimethyl-1H-indazol-3-yl)-5-pyridin-3-yl-thiazol-4-yl]-(4-pyridin-4-ylmethyl-piperazin-1-yl)-methanone | 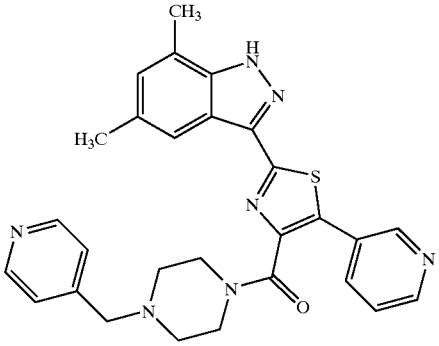 |

TABLE 1-continued

| No. | Name | Structure |
|---|---|---|
| 177. | [2-(5,7-Dimethyl-1H-indazol-3-yl)-5-pyridin-3-yl-thiazol-4-yl]-(2-pyrrolidin-1-ylmethyl-pyrrolidin-1-yl)-methanone | 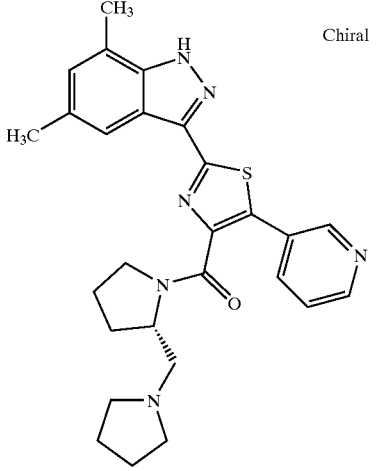 Chiral |
| 178. | [2-(5-Fluoro-7-methyl-1H-indazol-3-yl)-5-pyridin-3-yl-thiazol-4-yl]-(4-methyl-piperazin-1-yl)-methanone | 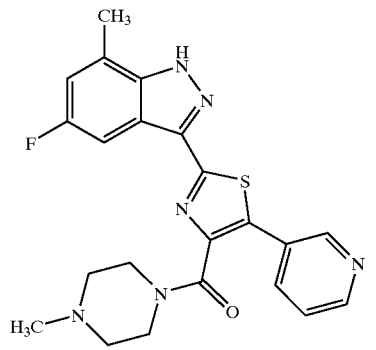 |
| 179. | [2-(5-Fluoro-7-methyl-1H-indazol-3-yl)-5-pyridin-3-yl-thiazol-4-yl]-piperazin-1-yl-methanone | 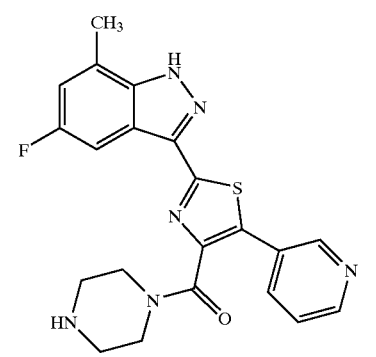 |
| 180. | (3-Methylamino-pyrrolidin-1-yl)-[2-(7-methyl-1H-indazol-3-yl)-5-pyridin-3-yl-thiazol-4-yl]-methanone | 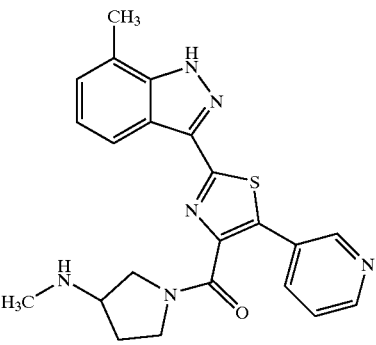 |

TABLE 1-continued

| No. | Name | Structure |
|---|---|---|
| 181. | (3-Diethylamino-pyrrolidin-1-yl)-[2-(7-methyl-1H-indazol-3-yl)-5-pyridin-3-yl-thiazol-4-yl]-methanone | 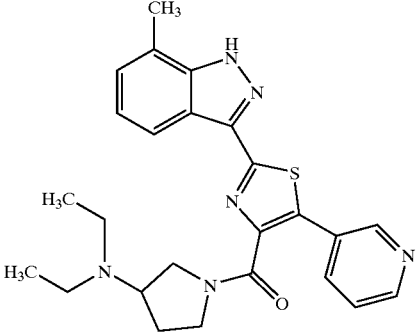 |
| 182. | (3-Diethylamino-pyrrolidin-1-yl)-[2-(5,7-dimethyl-1H-indazol-3-yl)-5-pyridin-3-yl-thiazol-4-yl]-methanone | 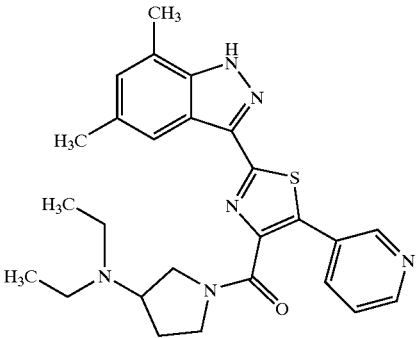 |
| 183. | [2-(5,7-Dimethyl-1H-indazol-3-yl)-5-pyridin-3-yl-thiazol-4-yl]-(2,3,5,6-tetrahydro-[1,2']bipyrazinyl-4-yl)-methanone | 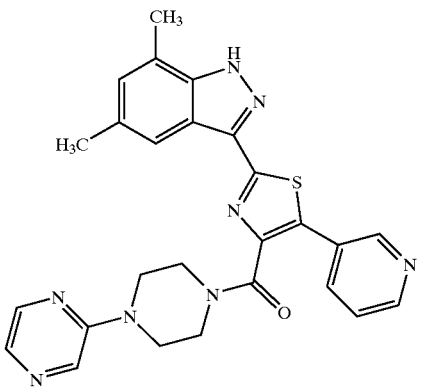 |
| 184. | 2-(5,7-Dimethyl-1H-indazol-3-yl)-5-pyridin-3-yl-thiazole-4-carboxylic acid (1-methyl-piperidin-4-yl)-amide | 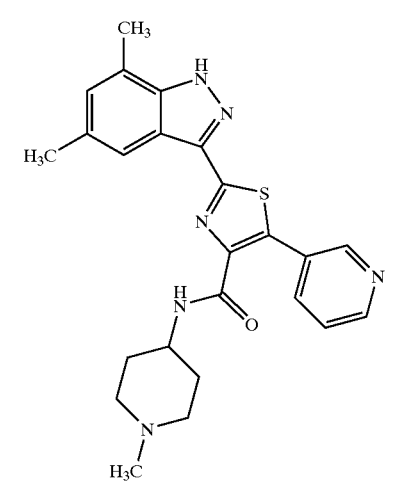 |

TABLE 1-continued

| No. | Name | Structure |
| --- | --- | --- |
| 185. | (4-Cyclopentyl-piperazin-1-yl)-[2-(5,7-dimethyl-1H-indazol-3-yl)-5-pyridin-3-yl-thiazol-4-yl]-methanone | 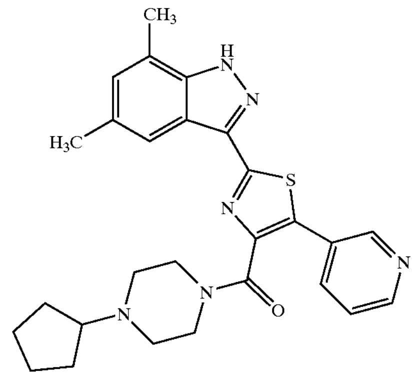 |
| 186. | [2-(5,7-Dimethyl-1H-indazol-3-yl)-5-pyridin-3-yl-thiazol-4-yl]-(4-pyridin-2-yl-piperazin-1-yl)-methanone | 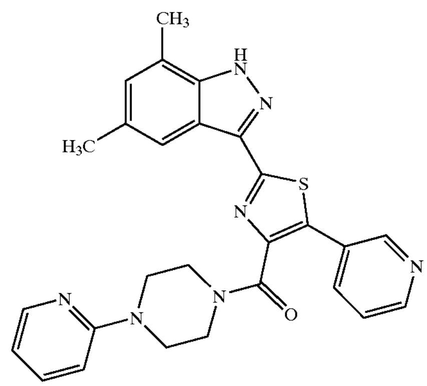 |
| 187. | [2-(5,7-Dimethyl-1H-indazol-3-yl)-5-pyridin-3-yl-thiazol-4-yl]-(4-isopropyl-piperazin-1-yl)-methanone | 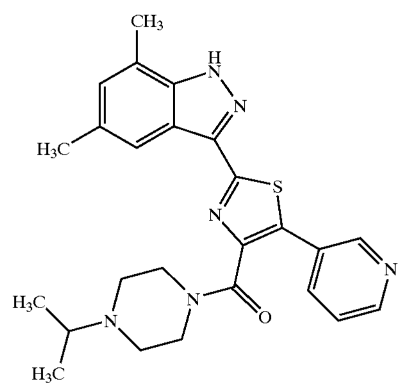 |

TABLE 1-continued

| No. | Name | Structure |
|-----|------|-----------|
| 188. | [2-(5,7-Dimethyl-1H-indazol-3-yl)-5-pyridin-3-yl-thiazol-4-yl]-(4-pyridin-2-ylmethyl-piperazin-1-yl)-methanone | 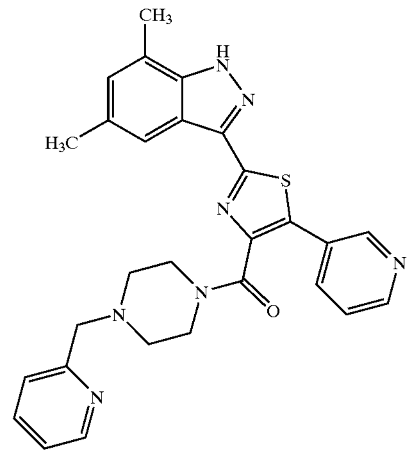 |
| 189. | [2-(5-Fluoro-7-methyl-1H-indazol-3-yl)-5-pyridin-3-yl-thiazol-4-yl]-(4-pyridin-2-yl-piperazin-1-yl)-methanone | 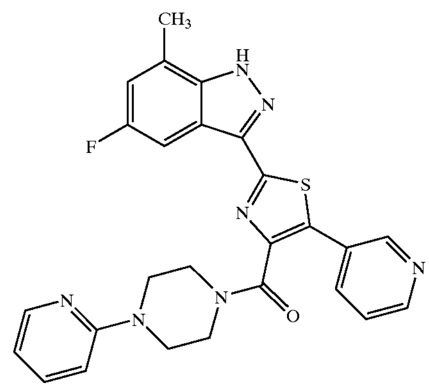 |
| 190. | 2-(5-Fluoro-7-methyl-1H-indazol-3-yl)-5-pyridin-3-yl-thiazole-4-carboxylic acid (1-methyl-piperidin-4-yl)-amide | 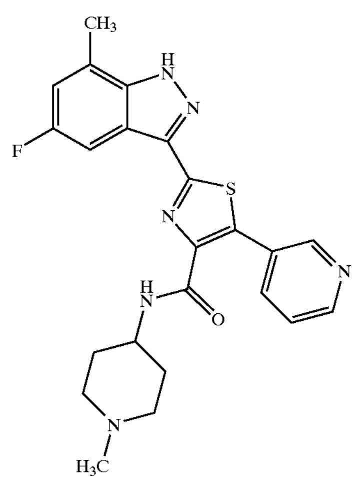 |

TABLE 1-continued

| No. | Name |
|---|---|
| 191. | [2-(5,7-Dimethyl-1H-indazol-3-yl)-5-pyridin-3-yl-thiazol-4-yl]-(4-pyridin-4-yl-piperazin-1-yl)-methanone |
| 192. | [2-(5-Fluoro-7-methyl-1H-indazol-3-yl)-5-pyridin-3-yl-thiazol-4-yl]-(4-isopropyl-piperazin-1-yl)-methanone |
| 193. | [2-(5-Fluoro-7-methyl-1H-indazol-3-yl)-5-pyridin-3-yl-thiazol-4-yl]-(4-pyridin-2-ylmethyl-piperazin-1-yl)-methanone |
| 194. | [2-(5,7-Dimethyl-1H-indazol-3-yl)-5-pyridin-3-yl-thiazol-4-yl]-[4-(2,2-dimethyl-propyl)-piperazin-1-yl]-methanone |

TABLE 1-continued

| No. | Name | Structure |
|---|---|---|
| 195. | 2-(5,7-Dimethyl-1H-indazol-3-yl)-5-pyridin-3-yl-thiazole-4-carboxylic acid [1-(2,2-dimethyl-propyl)-piperidin-4-yl]-amide | 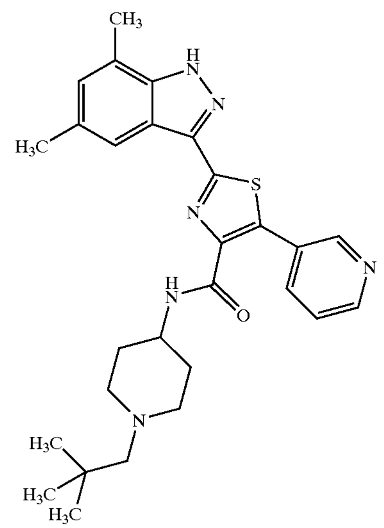 |
| 196. | 2-(5,7-Dimethyl-1H-indazol-3-yl)-5-pyridin-3-yl-thiazole-4-carboxylic acid (1-isopropyl-piperidin-4-yl)-amide | 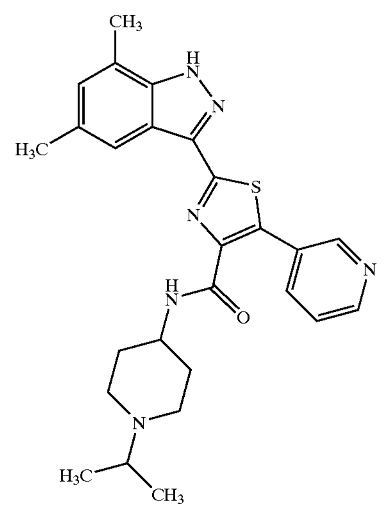 |
| 197. | [2-(5,7-Dimethyl-1H-indazol-3-yl)-5-pyridin-3-yl-thiazol-4-yl]-[3-(4-methyl-piperazin-1-yl)-azetidin-1-yl]-methanone | 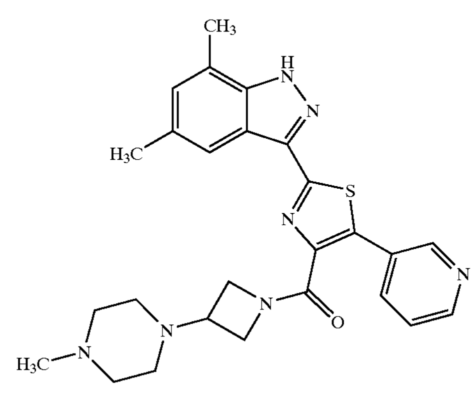 |

TABLE 1-continued

| No. | Name | Structure |
| --- | --- | --- |
| 198. | [2-(5,7-Dimethyl-1H-indazol-3-yl)-5-pyridin-3-yl-thiazol-4-yl]-(3-morpholin-4-yl-azetidin-1-yl)-methanone | 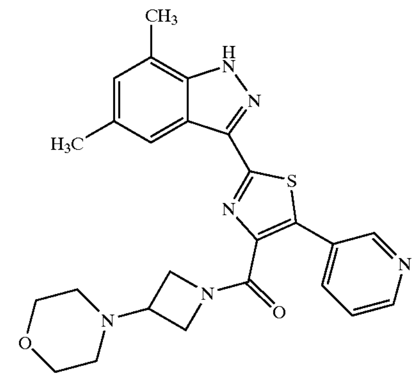 |
| 199. | [2-(5,7-Dimethyl-1H-indazol-3-yl)-5-pyridin-3-yl-thiazol-4-yl]-[3-(ethyl-methyl-amino)-azetidin-1-yl]-methanone | 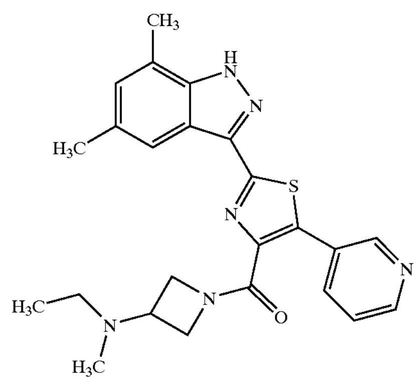 |
| 200. | (3-Methylamino-pyrrolidin-1-yl)-[2-(7-methyl-1H-indazol-3-yl)-5-pyridin-3-yl-thiazol-4-yl]-methanone | Chiral |
| 201. | 2-(5,7-Dimethyl-1H-indazol-3-yl)-5-pyridin-3-yl-thiazole-4-carboxylic acid (1,2,2,6,6-pentamethyl-piperidin-4-yl)-amide | 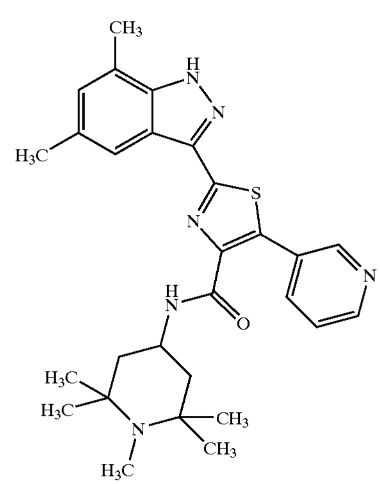 |

TABLE 1-continued

| No. | Name | Structure |
|---|---|---|
| 202. | 2-(5,7-Dimethyl-1H-indazol-3-yl)-5-pyridin-3-yl-thiazole-4-carboxylic acid piperidin-4-ylamide | 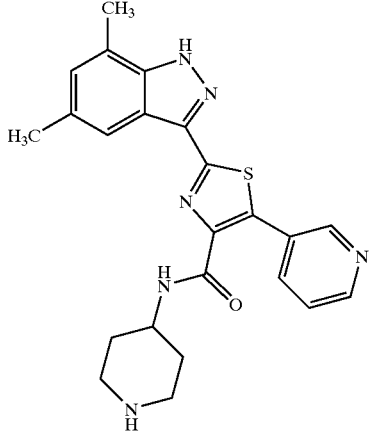 |
| 203. | [2-(5,7-Dimethyl-1H-indazol-3-yl)-5-pyridin-3-yl-thiazol-4-yl]-(3-morpholin-4-yl-pyrrolidin-1-yl)-methanone | 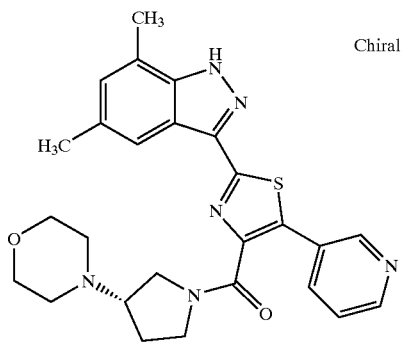 Chiral |
| 204. | [2-(5,7-Dimethyl-1H-indazol-3-yl)-5-pyridin-3-yl-thiazol-4-yl]-(3-hydroxy-[1,3']bipyrrolidinyl-1'-yl)-methanone | 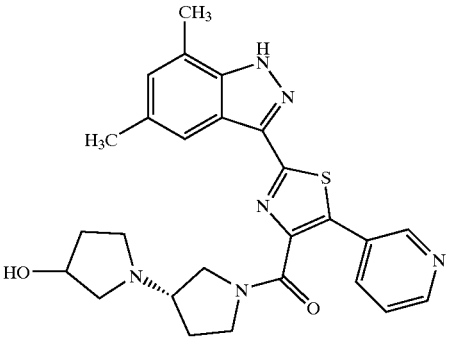 |
| 205. | [2-(5,7-Dimethyl-1H-indazol-3-yl)-5-pyridin-3-yl-thiazol-4-yl]-[3-(ethyl-methyl-amino)-pyrrolidin-1-yl]-methanone | 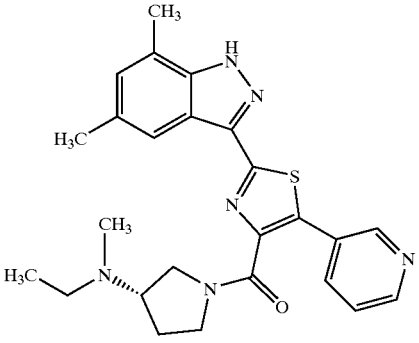 |

TABLE 1-continued

| No. | Name | Structure |
|---|---|---|
| 206. | [2-(5,7-Dimethyl-1H-indazol-3-yl)-5-pyridin-3-yl-thiazol-4-yl]-[3-(isopropyl-methyl-amino)-pyrrolidin-1-yl]-methanone | 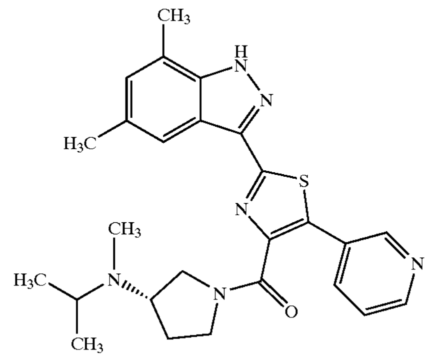 |
| 207. | 2-(5,7-Dimethyl-1H-indazol-3-yl)-5-pyridin-3-yl-thiazole-4-carboxylic acid methyl-(1-methyl-pyrrolidin-3-yl)-amide | 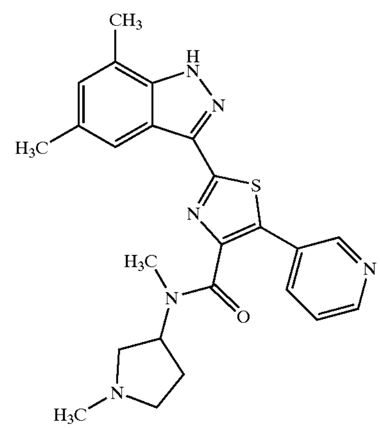 |
| 208. | [1,3']Bipyrrolidinyl-1'-yl-[2-(5,7-dimethyl-1H-indazol-3-yl)-5-pyridin-3-yl-thiazol-4-yl]-methanone | 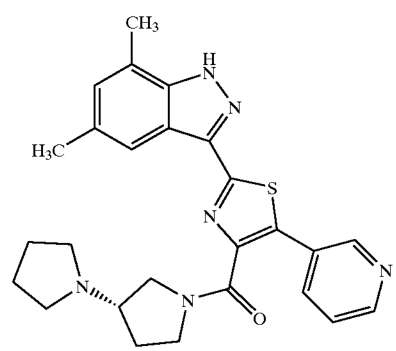 |
| 209. | 2-(7-Methyl-1H-indazol-3-yl)-5-pyridin-3-yl-thiazole-4-carboxylic acid methyl-(1-methyl-pyrrolidin-3-yl)-amide | 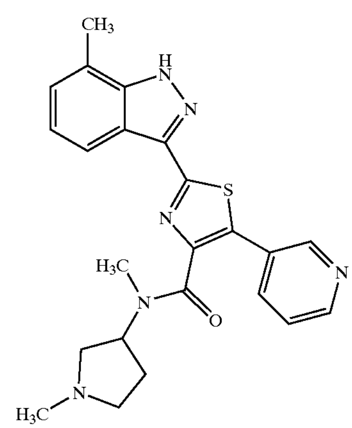 |

TABLE 1-continued

| No. | Name | Structure |
|---|---|---|
| 210. | 2-(5,7-Dimethyl-1H-indazol-3-yl)-5-pyridin-3-yl-thiazole-4-carboxylic acid methyl-(1-methyl-piperidin-4-yl)-amide | 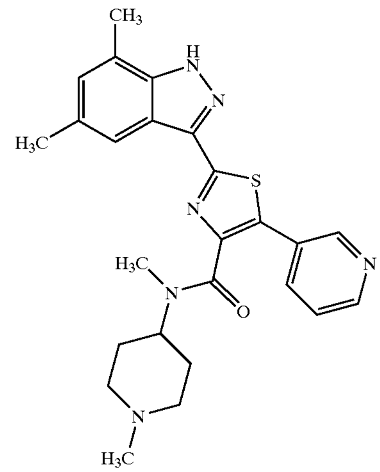 |
| 211. | 2-(7-Methyl-1H-indazol-3-yl)-5-pyridin-3-yl-thiazole-4-carboxylic acid methyl-(1-methyl-piperidin-4-yl)-amide | 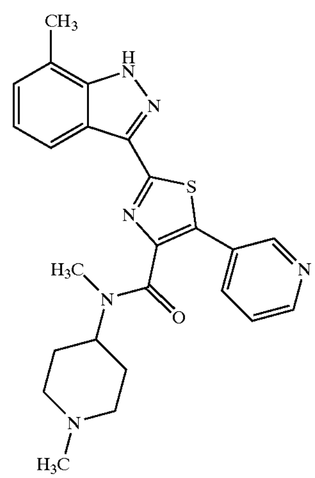 |
| 212. | 2-(7-Methyl-1H-indazol-3-yl)-5-pyridin-3-yl-thiazole-4-carboxylic acid (1,2,2,6,6-pentamethyl-piperidin-4-yl)-amide | 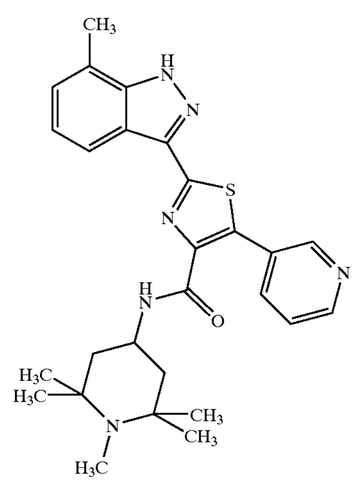 |

TABLE 1-continued

| No. | Name | Structure |
|---|---|---|
| 213. | (3-Diethylamino-azetidin-1-yl)-[2-(5,7-dimethyl-1H-indazol-3-yl)-5-pyridin-3-yl-thiazol-4-yl]-methanone | 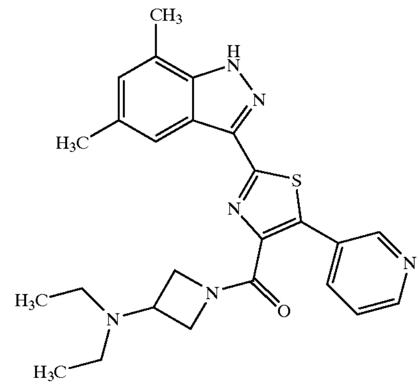 |
| 214. | [1,3']Bipyrrolidinyl-1'-yl-[2-(7-methyl-1H-indazol-3-yl)-5-pyridin-3-yl-thiazol-4-yl]-methanone | 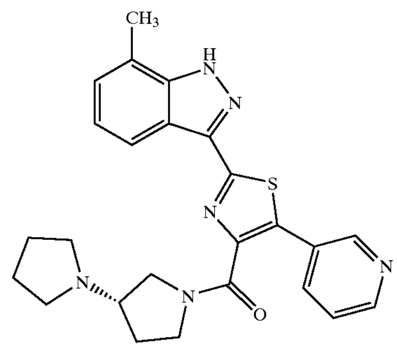 |
| 215. | [3-(Isopropyl-methyl-amino)-pyrrolidin-1-yl]-[2-(7-methyl-1H-indazol-3-yl)-5-pyridin-3-yl-thiazol-4-yl]-methanone | 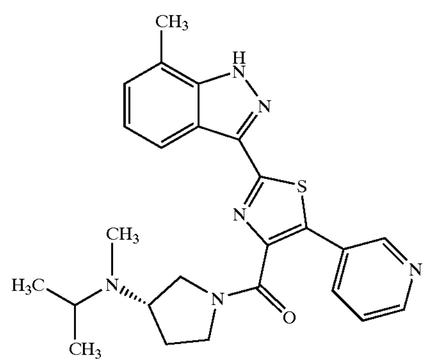 |
| 216. | [2-(7-Methyl-1H-indazol-3-yl)-5-pyridin-3-yl-thiazol-4-yl]-(3-morpholin-4-yl-azetidin-1-yl)-methanone | 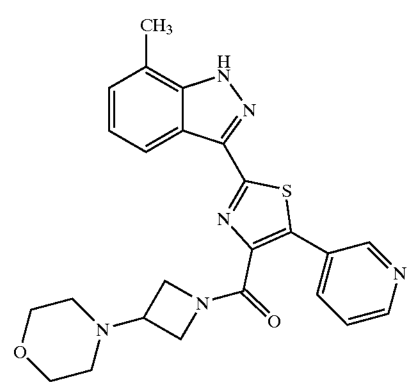 |

TABLE 1-continued

| No. | Name | Structure |
|---|---|---|
| 217. | 2-(7-Methyl-1H-indazol-3-yl)-5-pyridin-3-yl-thiazole-4-carboxylic acid (1-isopropyl-piperidin-4-yl)-amide | 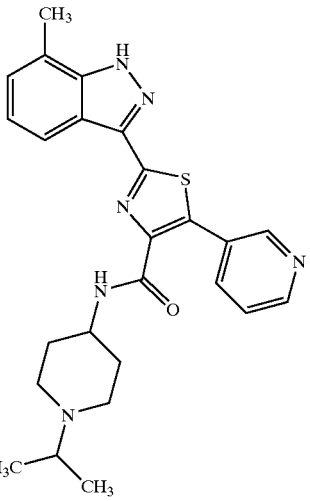 |

Methods of Using Compounds and Compositions

Preferred compounds of the formula (I) exhibit antimicrobial activity against a variety of pathogens. This invention is not bound by any theory of operation, but it is believed that compounds of the formula (I) exert their antimicrobial action by inhibiting gyrase B in the target bacteria in vivo and in vitro.

A preferred embodiment provides methods of treating or preventing a bacterial infection in a mammal, comprising administering to the mammal a therapeutically effective amount of a compound of the formula (I). Reference herein to the use of a compound of the formula (I) will be understood as including reference to pharmaceutical compositions thereof, as well as pharmaceutically acceptable salts, esters, solvates and/or prodrugs thereof. The prophylactic or therapeutic dose of the compounds of the present invention, in treatment of a bacterial infection will vary with the severity of the infection and the route by which the drug is administered, such as orally, topically, transdermally, and/or parenterally. The compounds of this invention are advantageously administered orally in either solid or liquid dosage forms, with the dose, and perhaps the dose frequency, varying according to the age, body weight, and response of the individual patient. In general, the total daily dose range of the present compounds for a 70 kg person is from about 1 mg to about 2000 mg, in single or divided doses, but those skilled in the art can readily determine the appropriate dose through standard methods.

Preferred compounds of the formula (I) have useful activity against a variety of organisms. The activity of the compounds can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3$^{rd}$ ed., published 1993 by the National Committee for Clinical Laboratory Standards, Villanova, Pa., USA. A number of the compounds of the formula (I) shown in Table 1 exhibit activity against one or more pathogenic bacteria such as Staphylococcus aureus, Staphylococcus epidermidis, Streptococcus pneumoniae, Streptococcus pyogenes, Enterococcus faecalis, Moraxella catarrhalis and H. influenzae. For example, Table 2 provides the names and structures of compounds of the formula (I) that were found to have a MIC of about 10 μM or less in the Methicillin-resistant Staphylococcus aureus assay conducted as described below in Examples 25–154.

EXAMPLES

General Chemistry Methods. Proton NMR spectra were run at 300 MHz on a Bruker Avance 300 spectrometer, and chemical shifts are reported in parts per million (δ) downfield from tetramethylsilane as internal standard. Atmospheric pressure ionization electrospray mass spectra and LCMS were recorded on an Agilent 1100 Series LC/MSD-SL 1946 D spectrometer equipped with an Agilent 100 series HPLC System. Silica gel 60 (230–400 mesh) from EM Science was used for column chromatography, and analytical or preparative thin-layer chromatography was conducted using EM Science Kieselgel 60 $F_{254}$ plates. An Agilent 1100 Series HPLC with an Agilent Zorbax Eclipse XDB-C8 (4.6×150 mm) reversed phase column was used for analytical HPLC analyses. Preparative RP-HPLC was performed on a Gilson instrument with a MetaSil AQUEOUS 10 m C18 column. The elution buffer was an A/B gradient; A=$H_2O$–0.1% trifluoroacetic acid, B=$CH_3$ CN–0.1% trifluoroacetic acid. Products were generally characterized by $^1$H-NMR, LC, and/or LC-MS.

For reactions performed under anhydrous conditions, glassware was either oven- or flame-dried and the reaction was run under a positive pressure of nitrogen. Anhydrous solvents were used as purchased from commercial sources. Except where noted, reagents were purchased from commercial sources and used without further purification. The reported yields are the actual isolated yields of purified material and are not optimized. The Examples 1–11 below describe the preparations of various specific compounds and are illustrative of the various materials and techniques that may be employed in the synthesis of the compounds of the formula (1). Examples 12–24 describe various steps in the synthesis of a particular compound of the formula (1). Table 1 provides the names and structures of various preferred compounds of the formula (I) prepared in accordance with the methods described herein. Examples 25–154 describe the Methicillin-resistant *Staphylococcus aureus* assay used to determine the activity of the compounds shown in Table 2.

Example 1

Dimethyl aniline (100 g, 82.5 mmoles; Scheme 1) was dissolved in 400 mL of dichloromethane and cooled to 0° C. To this solution was added dropwise acetyl chloride (71 mL, 1 mole) followed by a 200 mL solution of triethyl amine (140 mL, 1 mole). This solution was stirred until complete. Filter off the solid and pour the filtrate into brine, extract twice with dichloromethane, dry filter and concentrate to give 127.3 g (95% yield) of the acetylated amine as a tan solid. NMR data (300 MHz, $CDCl_3$) for 7-methyl indazoles: 7-methyl indazole: 8.14 (s, 1 H); 7.62 (d, 1 H, J=8.8 Hz); 7.18 (m, 1 H); 7.09 (m, 2 H); 2.6 (s, 3 H); 3-iodo-7-methyl indazole: 7.36 (d, 1 H, J=8.8 Hz); 7.24 (dd, 1 H, J=1 Hz, 2.55 (s, 3 H); 3-cyano-7-methyl indazole: 11 (bs, 1 H); 7.7 (m, 1 H), 7.3 (m, 2 H); H).

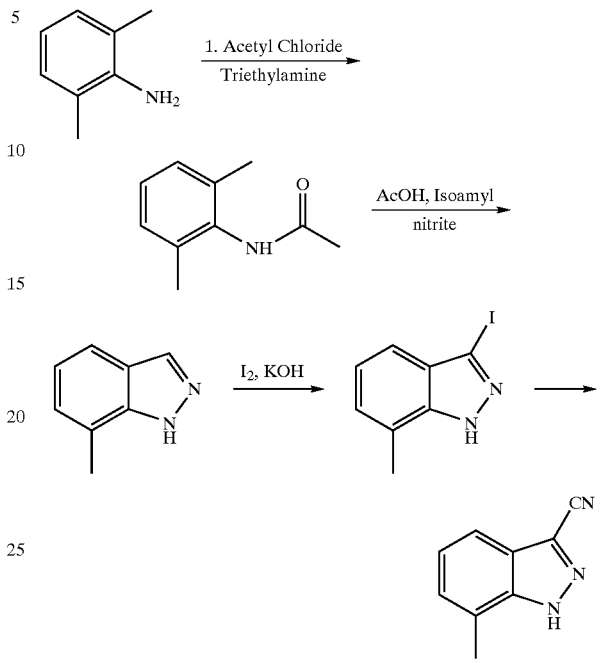

Scheme 1.
Synthesis of 3-cyanoindazoles

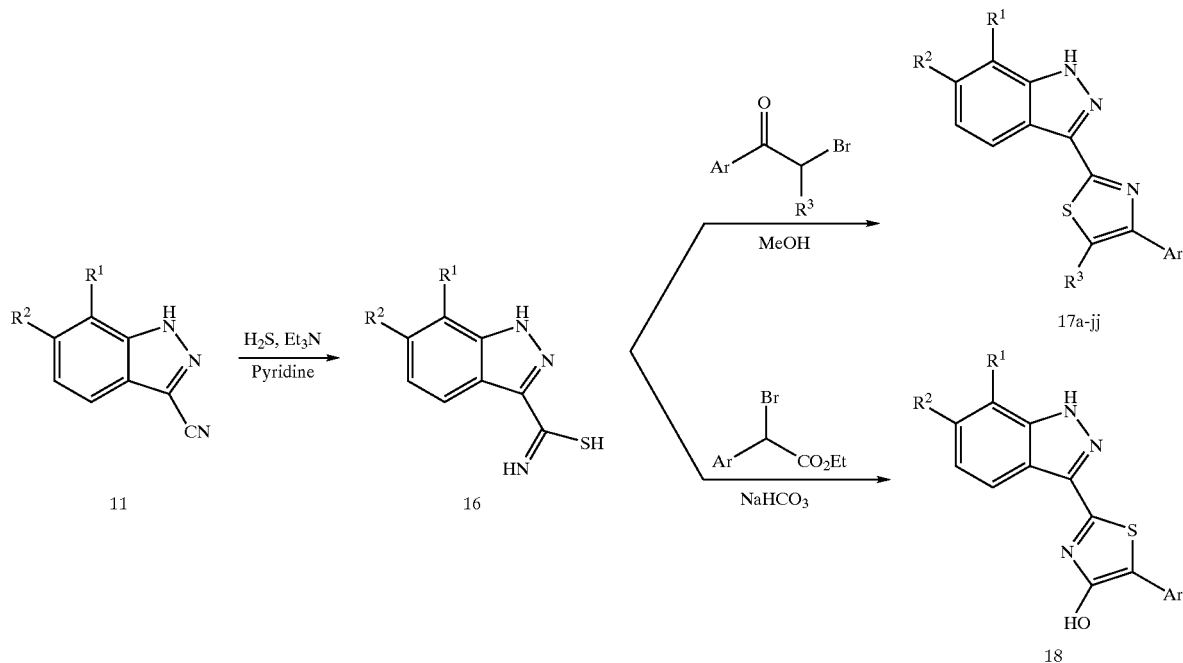

Scheme 2.
Synthesis of substituted thiazolyl indazoles

Example 2

Representative Thioamide Preparation 1H-indazole-3-carboximidothioic acid (16, $R^1=R^2=H$; Scheme 2). A solution of 1H-indazole-3-carbonitrile (11, $R^1=R^2=H$) (0.150 g, 1.05 mmol) in 20% $Et_3$ N/pyridine (101mL) was cooled to −78° C. Through this was then bubbled $H_2S$ gas for 20 minutes, and then the vessel was sealed and allowed to warm to room temperature and stir overnight. Residual $H_2S$ was removed in vacuo and the mixture concentrated. The resultant ivory colored solid was suspended in hexane, collected by filtration, and dried to provide 0.178 g, (95%) of product 16.

Examples 3–4

Representative Thiazole Preparations

3-[4-(4-bromo-phenyl)-5-methyl-thiazol-2-yl]-1H-indazole (17a, $R^1=R^2=H$, $R^3=CH_3$, Ar=3-bromophenyl; Scheme 2). A mixture of 1H-indazole-3-carboximidothioic acid (16, $R^1=R^2=H$) (354 mg, 2 mmol) and 2,4'-dibromopropiophenone (584 mg, 2 mmol) in dry MeOH (10 mL) was heated at 50° C for 20 h. The reaction mixture was filtered, the solids washed with MeOH and dried to give 430 mg (58%) of product 17a as a tan solid.

2-(1H-indazol-3-yl)-5-phenyl-thiazol-4-ol (18, $R^1=R^2=H$; Scheme 2). Similarly, 1H-indazole-3-carboximidothioic acid (16, $R^1=R^2=H$) (0.150 g, 0.85 mmol), methyl α-bromophenyl acetate (0.195 g, 0.85 mmol), and $NaHCO_3$ (0.142 g, 1.7 mmol) were dissolved in dry methanol and stirred overnight. The solution was concentrated, and the residue purified by preparative RP-HPLC providing 12 mg (5%) of the desired product 18 as an orange solid.

Examples 5–6

Representative Palladium-Mediated Aryl Amination

Scheme 3

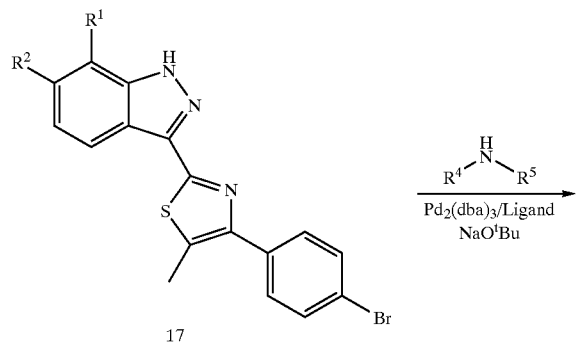

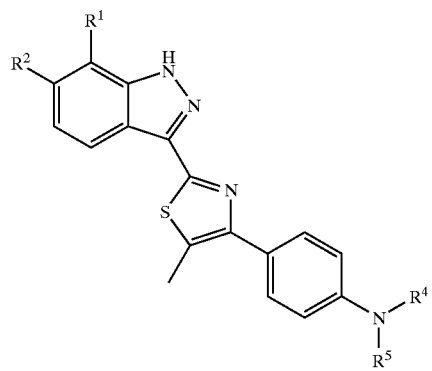

3-{5-Methyl-4-[4-(4-methyl-piperazin-1-yl)-phenyl]-thiazol-2-yl}-1H-indazole (19a, $R^1=R^2=H$, $R^4=R^5=$cyclo-$CH_2CH_2N(CH_3)CH_2CH_2$; Scheme 3). An oven-dried round-bottom flask was charged with 3-[4-(4-bromo-phenyl)-5-methyl-thiazol-2-yl]-1-1H-indazole (17, $R^1=R^2=H$, $R^3=CH_3$) (37 mg, 0.1 mmol), 1-methylpiperazine (67 µL, 0.6 mmol), NaO$^t$Bu (14 mg, 0.14 mmol) and anhydrous dimethyl ether (2 mL). The reaction mixture was evacuated and backfilled with $N_2$ several times. The catalyst, $Pd_2(dba)_3$ (9 mg, 0.01 mmol) and the ligand, 2-(dicyclohexylphosphino)biphenyl (14 mg, 0.04 mmol) were added. The reaction mixture was again evacuated and backfilled with $N_2$ and then heated at reflux overnight after which time HPLC analysis indicated complete consumption of starting material. The mixture was concentrated in vacuo, dissolved in EtOAc (20 mL) and washed with $H_2O$ (2×5 mL), brine (1×5 mL) and dried over anhydrous $Na_2SO_4$. Removal of solvent afforded the crude product that was purified by RP-HPLC to give 10 mg of product 19a (25%) as a light yellow solid.

3-[5-methyl-4-(4-morpholin-4-yl-phenyl)-thiazol-2-yl]-1H-indazole (19b, $R^1=R^2=H$, $R^4=R^5=$cyclo-$CH_2CH_2OCH_2CH_2$; Scheme 3). An oven-dried round-bottom flask was charged with (17, $R^1=R^2=H$, $R^3=CH_3$) (37 mg, 0.1 mmol), morpholine (52 µL, 0.6 mmol), NaOtBu (14 mg, 0.14 mmol) and anhydrous toluene (2 mL). The reaction mixture was evacuated and backfilled with $N_2$ several times. The catalyst, $Pd_2(dba)_3$ (9 mg, 0.01 mmol) and the ligand, BINAP (18 mg, 0.03 mmol) were added. The reaction mixture was again evacuated and backfilled with $N_2$ and then heated at reflux overnight after which time HPLC analysis indicated complete consumption of starting material. The mixture was concentrated in vacuo, dissolved in EtOAc (20 mL) and washed with $H_2O$ (2×5 mL), brine (1×5 mL) and dried over anhydrous $Na_2SO_4$. Removal of solvent affords the crude product 19b that was purified by RP-HPLC.

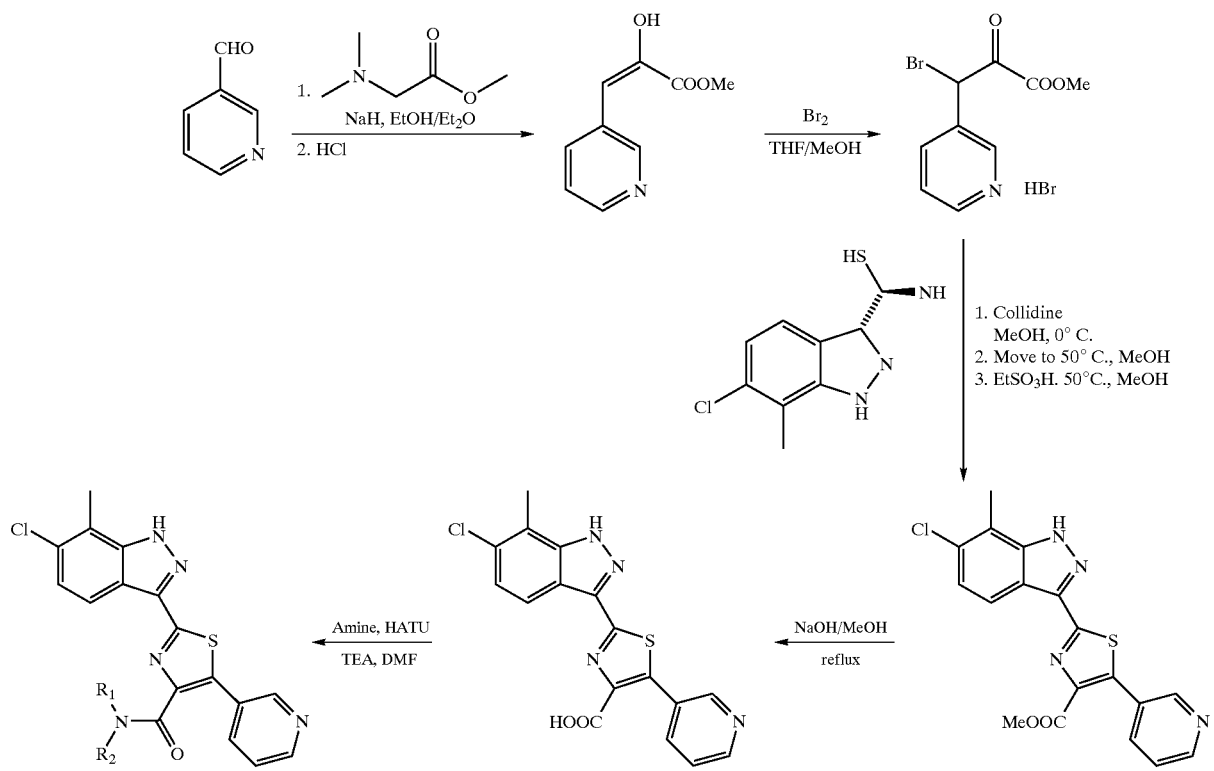

Scheme 4

Example 7
2-hydroxy-3-pyridin-3-yl-acrylic acid methyl ester (Scheme 4). To a mixture of dry ethanol (0.2 mL) and ether (20 mL) was added NaH (60% dispersion in oil, 800 mg, 20 mmol) at 0° C. and allowed it to stand for 10 min. After which, N,N-dimethylglycine methyl ester (3.5 g, 30 mmol) and 3-pyridine carboxyaldehyde (944 μL, 10 mmol) were added. The reaction mixture was stirred at 0° C. first and later at room temperature overnight. The mixture was diluted to ethyl acetate and washed with water. The organic layer was mixed with 1 N HCl and shaken well. Saturated NaHCO$_3$ solution was added to neutralize the aqueous layer, and the product was extracted three times with ethyl acetate. The combined organic layers were concentrated to give a solid mass, which was then treated with the minimum amount of ethyl acetate and filtered to give the product 2-hydroxy-3-pyridin-3-yl-acrylic acid methyl ester.

Example 8
3-bromo-2-oxo-3-pyridin-3-yl-propionic acid methyl ester hydrobromide, (Scheme 4). To a solution of 2-hydroxy-3-pyridin-3-yl-acrylic acid methyl ester (579 mg, 3 mmol, 1 equiv.) in 30 mL of THF was added bromine (154 μL, 3 mmol, 1 equiv.) in THF dropwise, followed by addition of methanol to dissolve the precipitate. The reaction mixture was allowed to stir at room temperature for 0.5 h and concentrated at room temperature with trituation a few times with THF and ethyl acetate. The product 3-bromo-2-oxo-3-pyridin-3-yl-propionic acid methyl ester hydrobromide was then dried under high vacuum and used without further purification.

Example 9
2-(6-chloro-7-methyl-1H-indazol-3-yl)-5-pyridin-3-yl-thiazole-4-carboxylic acid methyl ester (Scheme 4). To a round-bottom flask charged with 3-bromo-2-oxo-3-pyridin-3-yl-propionic acid methyl ester hydrobromide (obtained above, 353 mg, 1 mmol, 2 equiv.) and 5 mL of anhydrous methanol was added collidine (158 μL, 1.2 mmol, 2.4 equiv.) at 0° C., followed by the thioamide (112 mg, 0.5 mmol, 1 equiv.). The reaction mixture was then moved to 50° C., stirred for 2 h. LC-MS showed the complete consumption of the thioamide and the formation of a cyclized intermediate (before dehydration). At which point, ethanesulfonic acid (98 μL, 1.2 mmol, 2.4 equiv.) was added and the reaction mixture was stirred at 50° C. overnight. The reaction mixture was concentrated and the residue was purified by RP-HPLC or used for the next step (hydrolysis).

Example 10
2-(6-chloro-7-methyl-1H-indazol-3-yl)-5-pyridin-3-yl-thiazole-4-carboxylic acid (Scheme 4). The ester obtained above (2-(6-chloro-7-methyl-1H-indazol-3-yl)-5-pyridin-3-yl-thiazole-4-carboxylic acid methyl ester) was hydrolyzed in refluxing methanol in the presence of 1 N NaOH. The reaction mixture was then concentrated and diluted with water. HCl was then added to acidify the solution. The precipitate was filtered, washed by water. The solid was dried under high vacuum. The product was finally purified by RP-HPLC.

Example 11
2-(6-chloro-7-methyl-1H-indazol-3-yl)-5-pyridin-3-yl-thiazol-4-yl]-methanone hydrochloride. To a mixture of the acid, 2-(6-chloro-7-methyl-1H-indazol-3-yl)-5-pyridin-3-yl-thiazole-4-carboxylic acid (1 equiv.), triethyl amine (3 equiv.), the amine (5-10 equiv.) in DMF, was added O-(7-azabenzotriazol-1-yl)-1,1,3,3-tetramethyluronium hexafluorophosphate (1.4 equiv.). The reaction was completed usually within minutes. The product was purified by RP-HPLC. The trifluoroacetate salt was transferred to hydrochloride salt.
Scheme 5
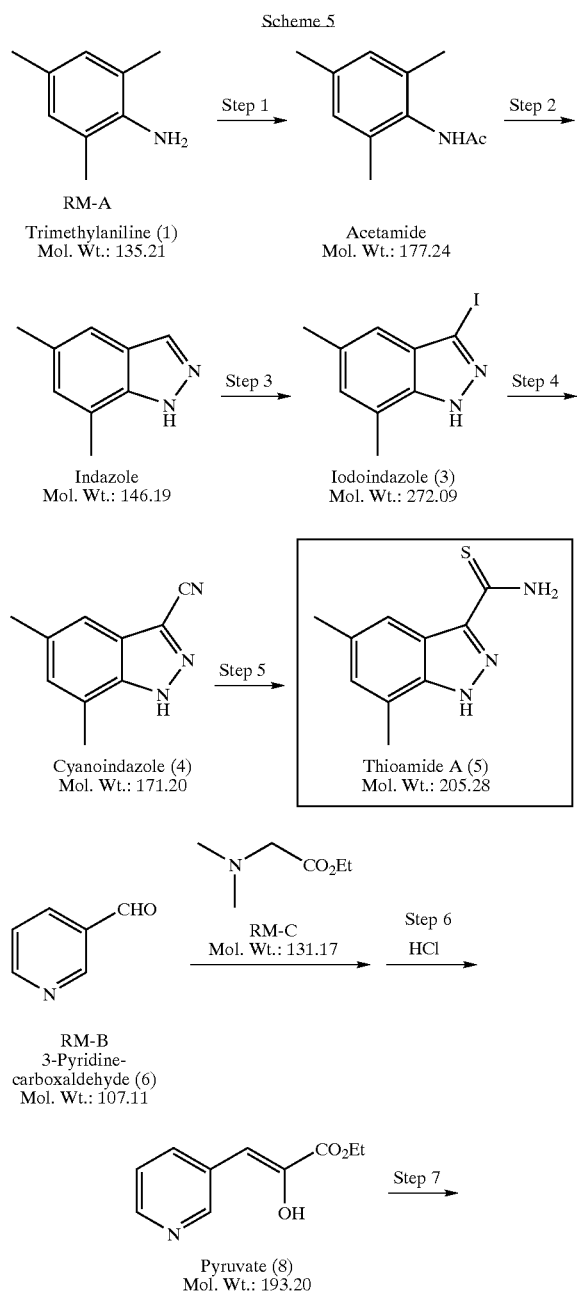
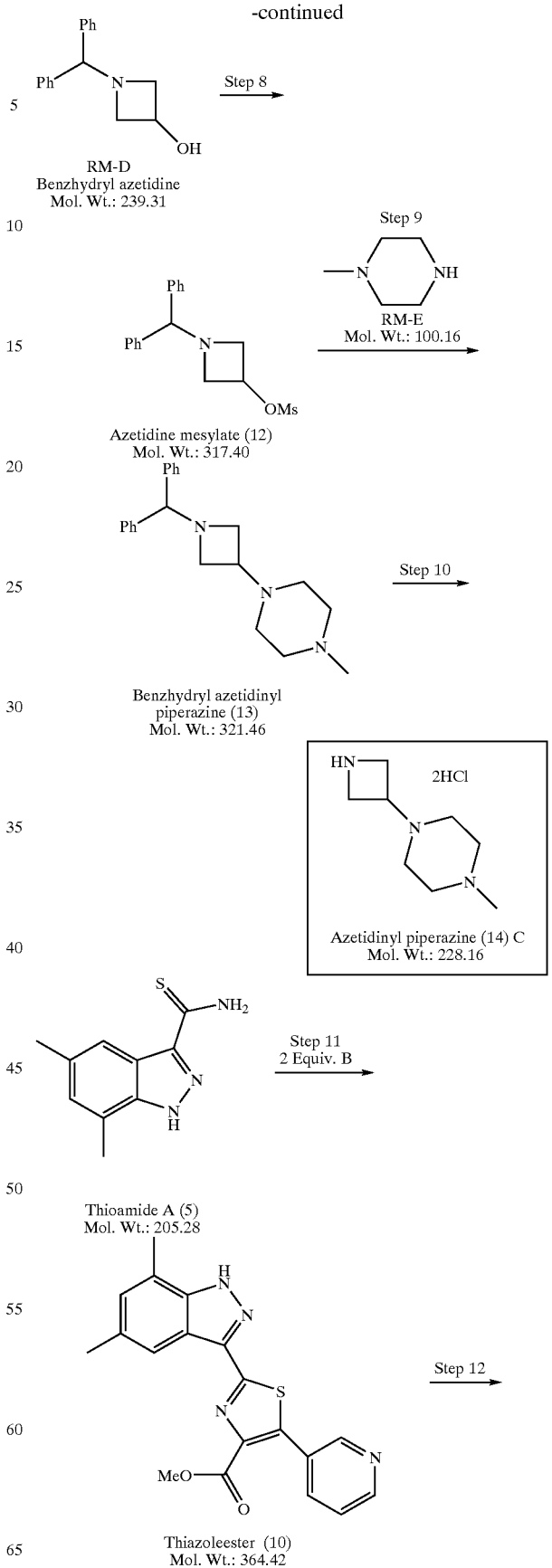

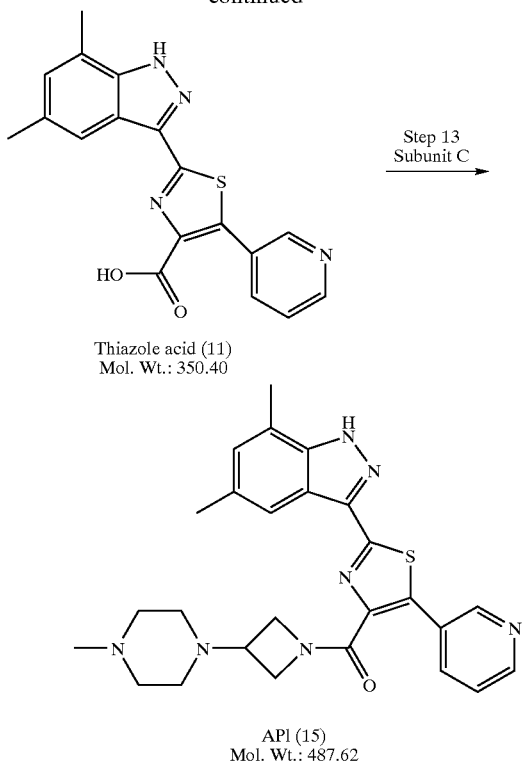

Thiazole acid (11)
Mol. Wt.: 350.40

Step 13
Subunit C

API (15)
Mol. Wt.: 487.62

Example 12

N-(2,4,6-trimethyl-phenyl)-acetamide (Scheme 5, step 1). A solution of 2,4,6-trimethyl-phenylamine (1) (50 g, 0.370 moles) in $CH_2Cl_2$ (500 mL) was cooled to 0° C. (ice-water bath). To this was added acetyl chloride (29.8 g, 27 mL, 380 mmol) during 5 minutes via an addition funnel; this was followed by portion-wise addition of $Et_3N$ (38.5 g, 53 mL, 380 mmol). The ice-bath was removed and the solution was allowed to warm to room temperature and stir for 2 h. The resultant ivory colored solid was collected by filtration and dried in vacuo. To remove residual $Et_3N.HCl$, the solid was suspended $H_2O$ (600 mL) stirred for 0.5 h, collected by filtration and dried to a constant weight. The original organic filtrate was washed with $H_2O$ (3×100 mL) and brine (1×100 mL), dried ($MgSO_4$), filtered and concentrated providing additional product. Combined with material collected from the water afforded 60.2 g (99% yield) of the desired acetamide. RP-HPLC Method: 2-100 B in 2 minutes.

Example 13

5,7-Dimethyl-1H-indazole (2) (Scheme 5, step 2). N-(2,4,6-trimethyl-phenyl)-acetamide (23.8 g, 133 mmol) (prepared as described in Example 12) was dissolved in a mixture of toluene (300 mL) and glacial AcOH (10.4 g, 173 mmol, 1.3 eq) and then treated slowly with isoamyl nitrite (20.3 g, 23.2 mL, 173 mmol, 1.3 eq). The mixture was heated at reflux overnight or until all the starting material was consumed as judged by TLC (30% EtOAc-hexanes). The solution was then poured into $H_2O$ (1.3 L) and extracted with EtOAc (2×300 mL). The combined organic extracts were then washed with saturated aq. $NaHCO_3$ solution (2×200 mL) and brine (1×100 mL). The extracts were dried (MgSO4), filtered, and concentrated to provide 19.5 g of 5,7-dimethyl-1H-indazole 2 as a red waxy solid. This material was carried on without additional purification. RP-HPLC Method: 2-100% B in 2 minutes Example 14

3-Iodo-5,7-dimethyl-1H-indazole (3) (Scheme 5, step 3). Indazole 2 (27.2 g, 186 mmol) in DMF (500 mL) was treated with iodine crystals (143.9 g, 567 mmol, 3 eq) and KOH (52.9 g, 945 mmol, 5 eq). The mixture was stirred at room temperature for 2 h or until complete as indicated by TLC (30% EtOAc-hexanes). The solution was concentrated to half volume, poured into 5% aq. $NHSO_3$ (250 mL) and extracted with $Et_2O$ (3×250 mL). The organic extracts were combined, washed with $H_2O$ (2×200 mL) and brine (1×200 mL), dried over (MgSO4), filtered and concentrated. The resultant dark solid was suspended in hot EtOAc (300 mL), treated with hexane (600 mL) and then allowed to cool for 2 h. The solids were collected by filtration, providing 17.50 g of crop 1. The filtrate was concentrated and crop 2 was isolated via silica gel plug filtration. (20% EtOAc-hexanes). Concentration of the appropriate "filtography" fractions afforded 9.5 g of material that was combined with crop 1 give a total of 27 g (53% overall yield from acetanilide) of 3-iodo-5,7-dimethyl-1H-indazole 3. RP-HPLC Method 2–100% B in 2 minutes.

Example 15

5,7-Dimethyl-1H-indazole-3-carbonitrile (4) (Scheme 5, step 4). Iodide 3 (20 g, 74.0 mmol) was dissolved in anhydrous NMP (300 mL). To this solution were added CuCN (19.9 g, 222 mmol, 3 eq) and NaCN (7.25 g, 148 mmol, 2 eq) and the mixture was heated at 130 ° C. for 18 h under an inert atmosphere. This solution was then poured into 0.25 M $KH_2PO_4$ (1.5 L) and $Et_2O$ (750 mL) and Celite (~100g) were added. The suspension was stirred vigorously for 0.5 h then filtered through a sintered glass funnel. The phases were separated and the aqueous layer extracted with $Et_2O$ (3×200 mL). The combined organic extracts were washed with $H_2O$ (2×200 mL), brine (1×200 mL), dried (MgSO4), filtered and concentrated provide 8.3g (65% yield) of 5,7-dimethyl-1H-indazole-3-carbonitrile 4. The nitrile was used as is for the next reaction. RP-HPLC Method: 2–100% B in 2 minutes.

Example 16

5,7-Dimethyl-1H-indazole-3-carboximidothioic acid A (5) (Scheme 5, step 5). A solution of nitrile 4 (3.90 g, 22.0 mmol) in 20% $Et_3N$-pyridine (v/v, 50 mL) was cooled to 0° C. (ice-water bath) and then saturated with $H_2S$ by bubbling $H_2S$ gas through for 5 minutes. The reaction vessel was sealed with stoppers and Parafilm, removed from the cooling bath, and stirred for 1.5 h, or until consumption of starting material was complete as indicated by TLC (50% EtOAc-hexanes). Upon completion, the solution was stirred under vacuum to remove excess $H_2S$ and then concentrated to leave a brown solid. The crude product was suspended in hexane (250–300 mL), collected by vacuum filtration and dried over $P_2O_5$ in vacuo to give 4.2 g, (93% yield) of A (5) as a yellow solid. RP-HPLC Method: 30–95% B in 4.5 minutes.

Example 17

2-Hydroxy-3-pyridin-3-yl-acrylic acid ethyl ester (8) (Scheme 5, step 6). A dry 1 L round bottomed flask was charged with anhydrous $Et_2O$ (500 mL) and cooled to 0° C. (ice-water bath). After having been rinsed with hexane, NaH (60% w/w suspension in mineral oil, 16 g, 400 mmol, 2 eq, weight before rinsing) was added followed by absolute EtOH (23.2 mL, 400 moles, 2 eq). After 10 minutes, a mixture of 3-pyridine carboxaldehyde (18.8 mL, 200 mmol, 1 eq) and N,N-dimethyl glycine ethyl ester (84.8 mL, 3 eq) (N,N-dimethyl glycine methyl ester also performs satisfactorily in this preparation) was added during 1 minute. This mixture was as stirred overnight at room temperature, heated at 30° C. for 1 h, and then transferred to a 2 L separation funnel. The mixture was diluted with EtOAc (500 mL) and $H_2O$ (500 mL) and the organic phase was transferred to a beaker and stirred with 1N HCl (500 mL) at room temperature for 10 minutes. The mixture was checked to confirm a pH=1 and then the phases were separated. The aqueous layer was retained and slowly neutralized by the addition of solid $NaHCO_3$. This solution was extracted with EtOAc (3×300 mL), the combined extracts dried ($Na_2SO_4$), filtered and concentrated to a yellow solid. Crystallization from EtOAc-Hexanes (4:1) provided 20.0 g (52% yield) of pale yellow 8. RP-HPLC Method 2–100% B.

Example 18

3-Bromo-2-oxo-3-pyridin-3-yl-propionic acid ethyl ester hydrobromide B (9) (Scheme 5, step 7). To a solution of the pyruvate 8 (19.3 g, 100.0 mmol) in dry THF (400 mL) was added bromine (5.12 mL, 100.0 mmol) dropwise, followed by the addition of methanol (~10 mL) to maintain homogeneity. The reaction mixture was stirred for 30 minutes at room temperature, and then concentrated in vacuo at a bath temperature at or below 25° C. The resulting solid was triturated with THF (50 mL) and EtOAc (50 mL) three times. The resulting bromo pyruvate hydrobromide was isolated as yellow foam after drying under high vacuum in quantitative yields. The solid was used without further purification. (Occasionally, the crude bromo pyruvate product dries to a sticky gum. In this event, the material was dried as thoroughly as possible, dissolved in MeOH (0.5 mmol/mL), and used as is in the next step.) RP-HPLC Method 30–95% B in 8 minutes.

Example 19

3-Bromo-2-oxo-3-pyridin-3-yl-propionic acid ethyl ester (10) (Scheme 5, step 11). Contained in a 2-neck round-bottomed flask a suspension of thioamide A (5) (4.5 g, 22.0 mmol) in dry MeOH (100 mL) was heated at 50° C. Separately, a solution of bromo-pyruvate B (9) (15.5 g, 44.0 mmol) in anhydrous MeOH (88 mL) was treated with collidine (10.2 mL, 77.0 mmol) at 0° C. The bromo pyruvate/collidine solution was added dropwise to the thioamide suspension maintained at 50° C. The mixture, becoming homogeneous during addition of the bromo-pyruvate solution, is heated at 50° C. for 2 h, or until consumption of thioamide is complete as judged by RP-HPLC-MS (the condensed, non-dehydrated intermediate is observable; expected mass+18). After this time, $EtSO_3H$ acid (6.3 mL, 77.0 mmol) was added and heating continued at 50° C. overnight. The mixture was concentrated and the oily residue treated with saturated aqueous sodium bicarbonate solution (~100 mL). The resultant solid is collected by vacuum filtration and rinsed with water (2×30 mL) and dried under vacuum. The solid is purified by silica gel-plug filtration: an initial eluent of 100% $CH_2Cl_2$ removes any nitrile 4 formed (typically 1–3%) and subsequent elution with 2–5% MeOH-$CH_2Cl_2$ provides the methyl and ethyl ester mixture. RP-HPLC Methods: 30–95% B in 8 minutes for the non-dehydrated intermediate. 10–95% B in 8 minutes for the dehydrated final product.

Example 20

2-(5,7-dimethyl-1H-indazol-3-yl)-5-pyridin-3-yl-thiazole-4-carboxylic acid (11) (Scheme 5, step 12). A solution of esters 10 (8 g, ~22 mmol) in MeOH (100 mL) and 1N NaOH (50 mL) was heated at reflux for 2 hours. The mixture was concentrated, acidified with 1N HCl (100 mL), and the resulting solid collected by vacuum filtration. The solid was rinsed with $H_2O$ (3×20 mL) and dried under high vacuum to give 7.9 g, (51%) overall from thioamide 5. RP-HPLC Method: 10–95% B in 8 minutes.

Example 21

Methanesulfonic acid 1-benzhydryl-azetidin-3-yl ester (12) (Scheme 5, step 8). To a solution of 1-benzhydryl-azetidin-3-ol (15.0 g, 62.7 mmol) in dry $CH_2Cl_2$ (1 mL) at 0° C. (ice-water bath) under nitrogen was added dry $Et_3N$ (25 mL, 94.0 mmol). To this was then added a solution of methanesulfonyl chloride (5.8 mL, 75.2 mmol) in dry $CH_2Cl_2$ (50 mL) dropwise via pressure equalizing addition funnel. Upon complete addition, the cooling bath was removed and the mixture was stirred for 2 h. The heterogeneous mixture was treated with $H_2O$ (70 mL), the layers were separated and the aqueous layer was extracted with $CH_2Cl_2$ (2×100 mL). The combined organic extracts were dried ($MgSO_4$), filtered and concentrated to leave a clear, colorless oil. Upon addition of hexanes (100 mL) the viscous oil product solidified and was collected by vacuum filtration. Drying under high vacuum provided 19.7 g (100% yield) of 12 as a colorless solid.

Example 22

1-(1-Benzhydryl-azetidin-3-yl)-4-methyl-piperazine (13) (Scheme 5, step 9). To a suspension of methanesulfonic acid 1-benzhydryl-azetidin-3-yl ester (12) (18 g, 56.7 mmol) in t-BuOH (150 mL) was added 1-methyl piperazine (17.04 g, 18.8 mL, 170.1 mmol) under an inert atmosphere. After heating at reflux temperature for 12 h, the mixture was concentrated to dryness, treated with saturated $NaHCO_3$ (250 mL) and extracted with EtOAc (3×250 mL). The combined organic layers were washed with $H_2O$ (1×250 mL) and brine (1×250 mL) and dried ($Na_2SO_4$). Filtration and removal of solvent left oil that was purified by silica gel (~300 g) filtration (first washed with EtOAc, then with 100% ammoniacal $CH_2Cl_2$–5% MeOH/ammoniacal $CH_2Cl_2$) to afford 7.6 g (42%) of 13 as a colorless, waxy solid. Ammoniacal $CH_2Cl_2$ is prepared as follows: concentrated $NH_4OH$ (100 mL) is extracted with $CH_2Cl_2$ (1×500 mL), the layers are separated, and the $CH_2Cl_2$ layer is dried and stored over anhydrous $K_2CO_3$.

Example 23

1-Azetidin-3-yl-4-methyl-piperazine dihydrochloride C (14) (Scheme 5, step 10). A mixture of 1-(1-benzhydryl-azetidin-3-yl)-4-methyl-piperazine (13) (1.13 g, 3.5 mmol), wet 20% $Pd(OH)_2/C$ (0.6 g) or wet 10% Pd/C degussa type (0.22 g), MeOH (50 ml) and 4N HCl in MeOH solution (1.8 ml, 7.0 mmol) was shaken under an $H_2$ gas (50 p.s.i.g.) for 12 h. The catalyst was removed by filtration over Celite; the filter bed was rinsed with MeOH (3×10 mL) and the filtrate evaporated to dryness, and the residue rinsed with a mixture of $Et_2O$ (2 mL) and hexanes (10 ml) to remove diphenylmethane. The product C (14) crystallized upon standing providing 0.77 g (96% yield) of colorless, hygroscopic material that was used as is in subsequent steps.

Example 24

[2-(5,7-Dimethyl-1H-indazol-3-yl)-pyridin-3-yl-thiazol-4-yl]-[3-(4-methyl-piperazin-1-yl)-azetidin-1-yl]- methanone (15) (Scheme 5, step 13). A mixture of acid 11 (1.04 g 3.07 mmol) and azetidine dihydrochloride C (14) (0.77 g, 3.37 mmol) in dry DMF (20 mL) was treated with dry Et$_3$N (2.14 mL, 15.34 mmol) under an inert atmosphere. To this was then added HATU (1.46 g, 3.84 mmol) in one portion. Efficient couplings have also been achieved using PyBop (1.4 equivalents based on 11) as the coupling agent. After stirring for 0.25 h, RP-HPLC indicates complete reaction. The mixture was transferred onto stirring concentrated NH$_4$OH (400 mL) and the resulting tan solid collected by vacuum filtration. Rinsing with H$_2$O (2×10 mL) and vacuum drying provided 0.64 g (44% yield) of 15 as the free base. Concentrating the filtrate, re-suspending in concentrated NH$_4$OH (7 mL) and collecting by vacuum filtration provided an additional 90 mg of 15.

Examples 25–154

Biological Assays

ATPase enzymatic assay: DNA gyrase B activities were determined by following the gyrase B-dependent release of inorganic phosphate from ATP hydrolysis and subsequent detection through use of a 7-methyl-6-thioguanosine/phosphorylase spectrophotometric assay. Assays were performed in 25 mM Tris-HCl buffer (pH 7.6), 2 mM MgCl$_2$, and 125 mM NaCl, 0.2 mM 7-methyl-6-thioguanosine, purine nucleoside phosphorylase (1 unit/mL), 0.4 mM ATP and various concentrations of the inhibitor compounds prepared in Me$_2$SO. The final Me$_2$SO concentration in each reaction was 2.5%. The compounds of the formula (D) shown in Table 1 were assayed against one or more of *Staphylococcus aureus, Staphylococcus epidermidis, Streptococcus pneumoniae, Streptococcus pyogenes, Enterococcus faecalis, Moraxella catarrhalis* and *H. influenzae*. The concentration of enzyme in the assay ranged from 65 nM for *E. faecalis* full-length gyrase B to 1 µM for *H. influenzae* full-length gyrase B. Reactions were initiated with the addition of ATP, and monitored at 360 nm at room temperature for 30 min.

Tight-binding kinetic analysis (Morrison, J. F. *Biochim. Biophys. Acta* 1969,185, 269–286)was used to determine $K_i$ if the concentration of inhibitor did not exceed that of enzyme.

Antimicrobial Activity Assay (MIC Determination)

Bacteria Preparations: Overnight bacterial colonies were suspended in 0.9% NaCl to a turbidity approximately comparable to the MacFarland's standard. The spectrometer was blanked (600 nm) using well-suspended standard. Into a cuvette was placed 0.5 mL of bacterial suspension and absorbance measured. A 0.9% NaCl solution was added to the cuvette, mixed and measured until the absorbance is 0. From this the dilution factor (to achieve an absorbance of 0) for the stock bacterial solution was calculated. A solution of bacteria at this dilution is defined as a stock of 1×10$^8$ bacteria/mL. A final concentration of 5×10$^5$ bacteria per well was used for MIC determinations.

Compound Preparation: Test compounds of the formula (I) were assayed over a wide range of concentrations using serial dilutions, dropping concentration by half at each step. Controls included wells containing no drug (uninhibited growth control), controls for no additive (no serum etc.), and controls for contamination (additives but no drugs or bacteria).

The compounds of the formula (I) shown in Table 1 were found to exhibit activity against one or more of *Staphylococcus aureus, Staphylococcus epidermidis, Streptococcus pneumoniae, Streptococcus pyogenes, Enterococcus faecalis, Moraxella catarrhalis* and *H. influenzae*. Table 2 provides the names and structures of compounds of the formula (I) that were found to have a MIC of about 10 µM or less in the Methicillin-resistant *Staphylococcus aureus* assay.

It will be appreciated by those skilled in the art that various omissions, additions and modifications may be made to the processes described above without departing from the scope of the invention, and all such modifications and changes are intended to fall within the scope of the invention, as defined by the appended claims.

TABLE 2

| NO. | STRUCTURE | NAME |
|---|---|---|
| 1. | 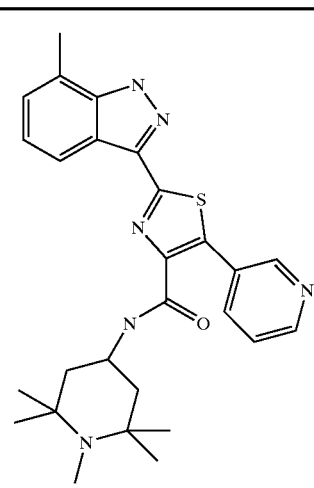 | 2-(7-Methyl-1H-indazol-3-yl)-5-pyridin-3-yl-thiazole-4-carboxylic acid (1,2,2,6,6-pentamethyl-piperidin-4-yl)-amide |

TABLE 2-continued

| NO. | STRUCTURE | NAME |
| --- | --- | --- |
| 2. | 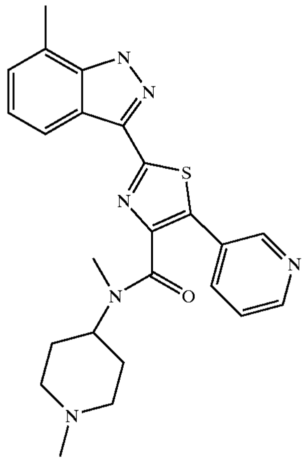 | 2-(7-Methyl-1H-indazol-3-yl)-5-pyridin-3-yl-thiazole-4-carboxylic acid methyl-(1-methyl-piperidin-4-yl)-amide |
| 3. | 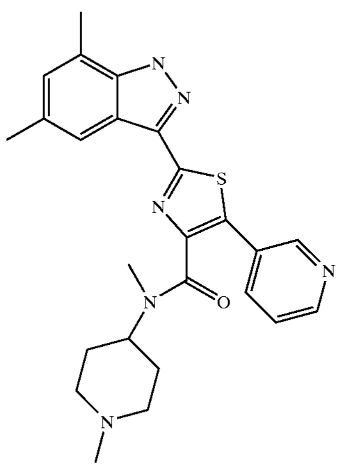 | 2-(5,7-Dimethyl-1H-indazol-3-yl)-5-pyridin-3-yl-thiazole-4-carboxylic acid methyl-(1-methyl-piperidin-4-yl)-amide |
| 4. | 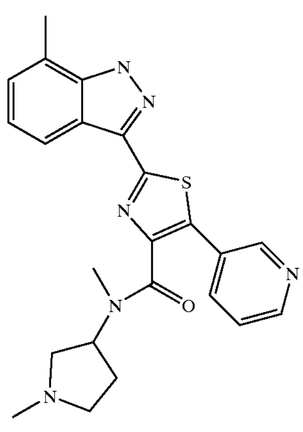 | 2-(7-Methyl-1H-indazol-3-yl)-5-pyridin-3-yl-thiazole-4-carboxylic acid methyl-(1-methyl-pyrrolidin-3-yl)-amide |

TABLE 2-continued

| NO. | STRUCTURE | NAME |
|---|---|---|
| 5. | 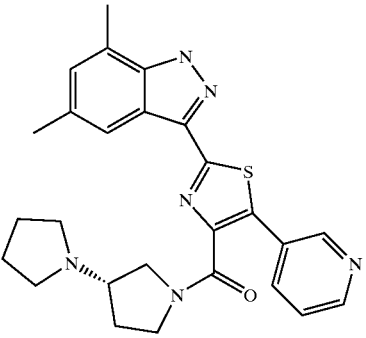 | [1,3']Bipyrrolidinyl-1'-yl-[2-(5,7-dimethyl-1H-indazol-3-yl)-5-pyridin-3-yl-thiazol-4-yl]-methanone |
| 6. | 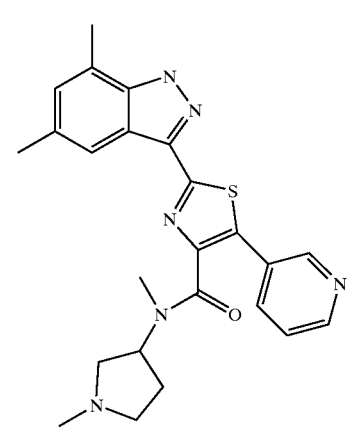 | 2-(5,7-Dimethyl-1H-indazol-3-yl)-5-pyridin-3-yl-thiazole-4-carboxylic acid methyl-(1-methyl-pyrrolidin-3-yl)-amide |
| 7. | 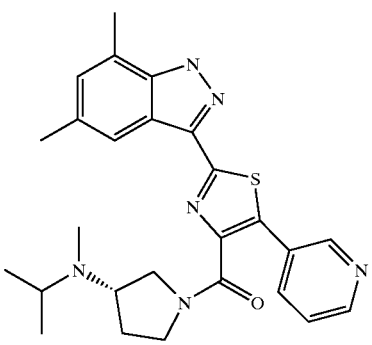 | [2-(5,7-Dimethyl-1H-indazol-3-yl)-5-pyridin-3-yl-thiazol-4-yl]-[3-(isopropyl-methyl-amino)-pyrrolidin-1-yl]-methanone |
| 8. | 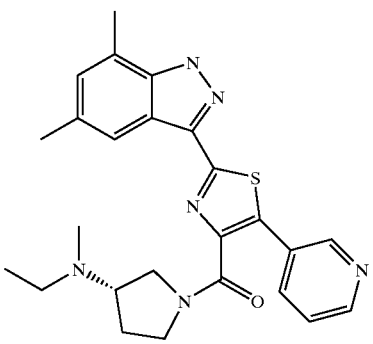 | [2-(5,7-Dimethyl-1H-indazol-3-yl)-5-pyridin-3-yl-thiazol-4-yl]-[3-(ethyl-methyl-amino)-pyrrolidin-1-yl]-methanone |

TABLE 2-continued

| NO. | STRUCTURE | NAME |
| --- | --- | --- |
| 9. | 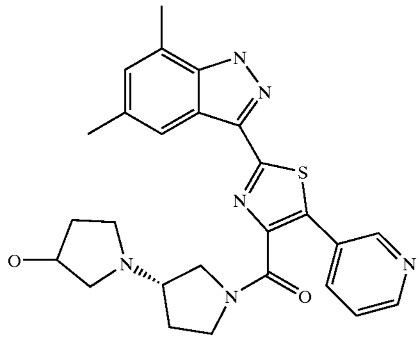 | [2-(5,7-Dimethyl-1H-indazol-3-yl)-5-pyridin-3-yl-thiazol-4-yl]-(3-hydroxy-[1,3']bipyrrolidinyl-1'-yl)-methanone |
| 10. | Chiral | [2-(5,7-Dimethyl-1H-indazol-3-yl)-5-pyridin-3-yl-thiazol-4-yl]-(3-morpholin-4-yl-pyrrolidin-1-yl)-methanone |
| 11. | 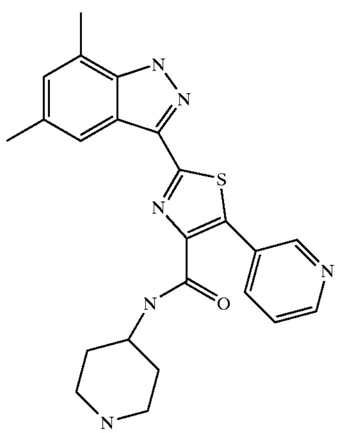 | 2-(5,7-Dimethyl-1H-indazol-3-yl)-5-pyridin-3-yl-thiazole-4-carboxylic acid piperidin-4-ylamide |
| 12. | 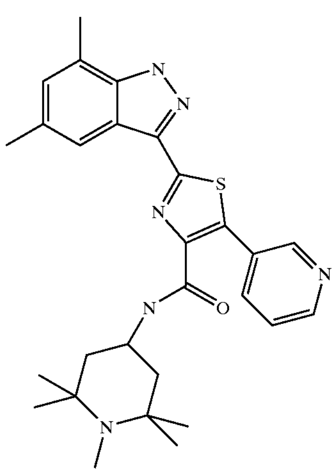 | 2-(5,7-Dimethyl-1H-indazol-3-yl)-5-pyridin-3-yl-thiazole-4-carboxylic acid(1,2,2,6,6-pentamethyl-piperidin-4-yl)-amide |

TABLE 2-continued

| NO. | STRUCTURE | NAME |
|---|---|---|
| 13. | 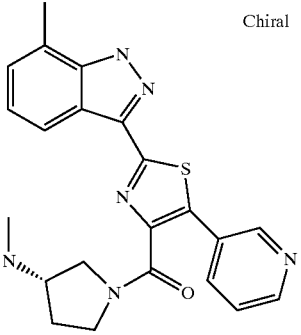 Chiral | (3-Methylamino-pyrrolidin-1-yl)-[2-(7-methyl-1H-indazol-3-yl)-5-pyridin-3-yl-thiazol-4-yl]-methanone |
| 14. | 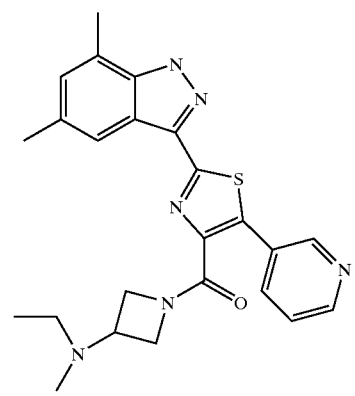 | [2-(5,7-Dimethyl-1H-indazol-3-yl)-5-pyridin-3-yl-thiazol-4-yl]-[3-(ethyl-methyl-amino)-azetidin-1-yl]-methanone |
| 15. | 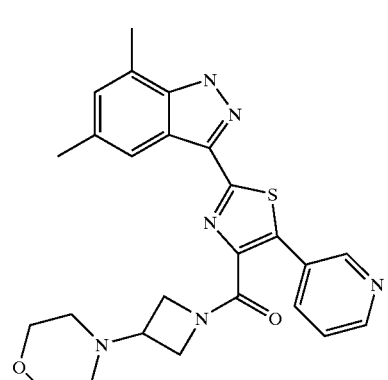 | [2-(5,7-Dimethyl-1H-indazol-3-yl)-5-pyridin-3-yl-thiazol-4-yl]-(3-morpholin-4-yl-azetidin-1-yl)-methanone |
| 16. | 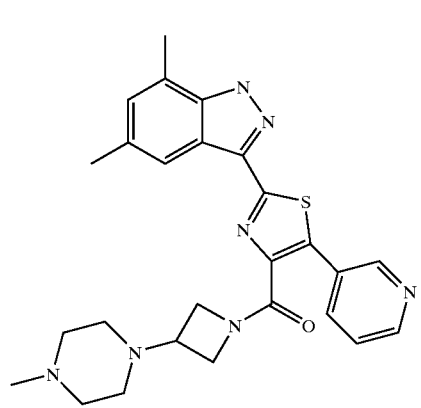 | [2-(5,7-Dimethyl-1H-indazol-3-yl)-5-pyridin-3-yl-thiazol-4-yl]-[3-(4-methyl-piperazin-1-yl)-azetidin-l-yl]-methanone |

TABLE 2-continued
| NO. | STRUCTURE | NAME |
|---|---|---|
| 17. | 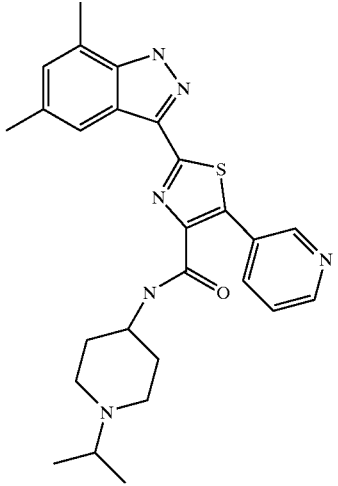 | 2-(5,7-Dimethyl-1H-indazol-3-yl)-5-pyridin-3-yl-thiazole-4-carboxylic acid (1-isopropyl-piperidin-4-yl)-amide |
| 18. | 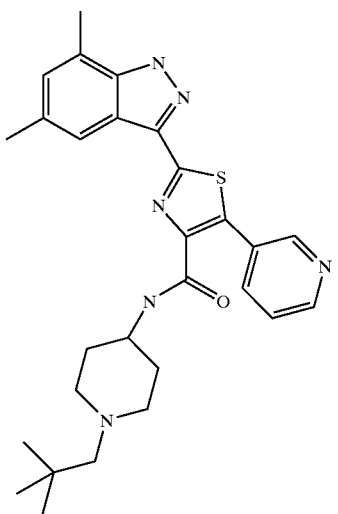 | 2-(5,7-Dimethyl-1H-indazol-3-yl)-5-pyridin-3-yl-thiazole-4-carboxylic acid [1-(2,2-dimethyl-propyl)-piperidin-4-yl]-amide |
| 19. | 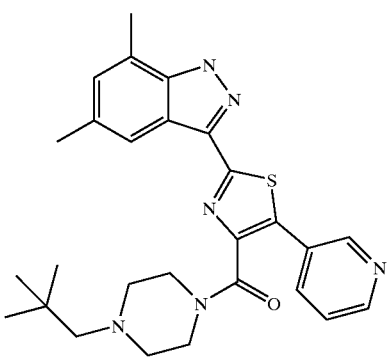 | [2-(5,7-Dimethyl-1H-indazol-3-yl)-5-pyridin-3-yl-thiazol-4-yl]-[4-(2,2-dimethyl-propyl)-piperazin-1-yl]-methanone |

TABLE 2-continued

| NO. | STRUCTURE | NAME |
|---|---|---|
| 20. | 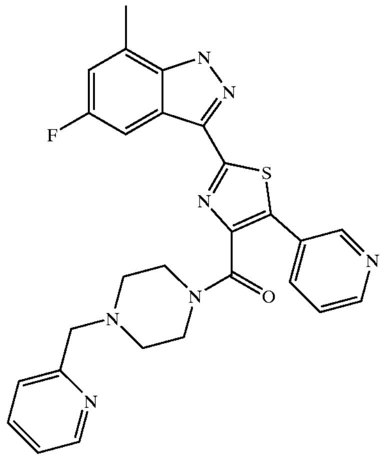 | [2-(5-Fluoro-7-methyl-1H-indazol-3-yl)-5-pyridin-3-yl-thiazol-4-yl]-(4-pyridin-2-ylmethyl-piperazin-1-yl)-methanone |
| 21. | 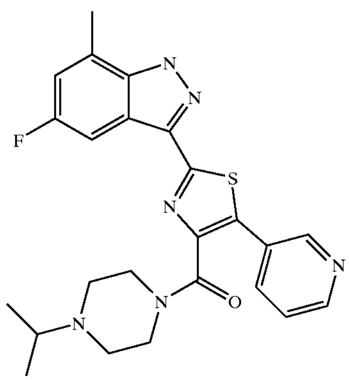 | [2-(5-Fluoro-7-methyl-1H-indazol-3-yl)-5-pyridin-3-yl-thiazol-4-yl]-(4-isopropyl-piperazin-1-yl)-methanone |
| 22. | 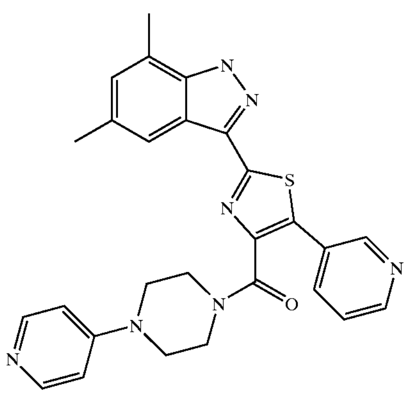 | [2-(5,7-Dimethyl-1H-indazol-3-yl)-5-pyridin-3-yl-thiazol-4-yl]-(4-pyridin-4-yl-piperazin-1-yl)-methanone |

TABLE 2-continued

| NO. | STRUCTURE | NAME |
| --- | --- | --- |
| 23. | 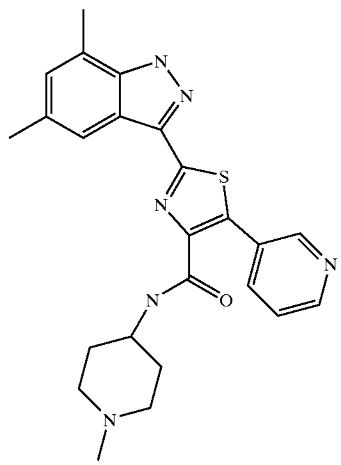 | 2-(5-Fluoro-7-methyl-1H-indazol-3-yl)-5-pyridin-3-yl-thiazole-4-carboxylic acid (1-methyl-piperidin-4-yl)-amide |
| 24. | 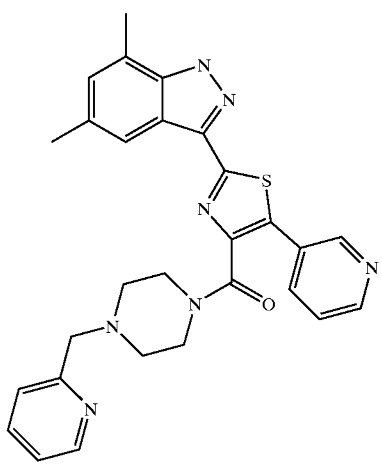 | [2-(5,7-Dimethyl-1H-indazol-3-yl)-5-pyridin-3-yl-thiazol-4-yl]-(4-pyridin-2-ylmethyl-piperazin-1-yl)-amide |
| 25. | 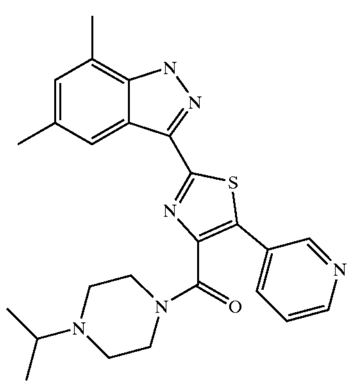 | [2-(5,7-Dimethyl-1H-indazol-3-yl)-5-pyridin-3-yl-thiazol-4-yl]-(4-iso-propyl-piperazin-1-yl)-methanone |

TABLE 2-continued
| NO. | STRUCTURE | NAME |
|---|---|---|
| 26. | 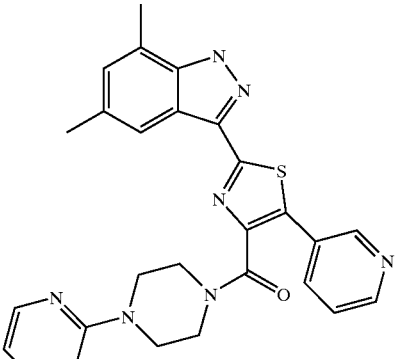 | [2-(5,7-Dimethyl-1H-indazol-3-yl)-5-pyridin-3-yl-thiazol-4-yl]-(4-pyridin-2-yl-piperazin-1-yl)-methanone |
| 27. | 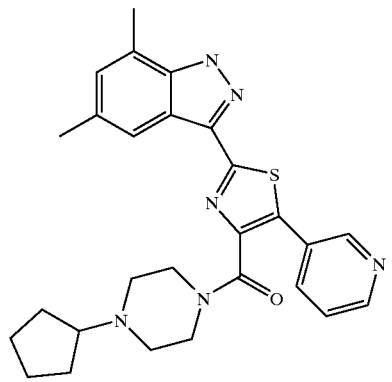 | (4-Cyclopentyl-piperazin-1-yl)-[2-(5,7-dimethyl-1H-indazol-3-yl)-5-pyridin-3-yl-thiazol-4-yl]-methanone |
| 28. | 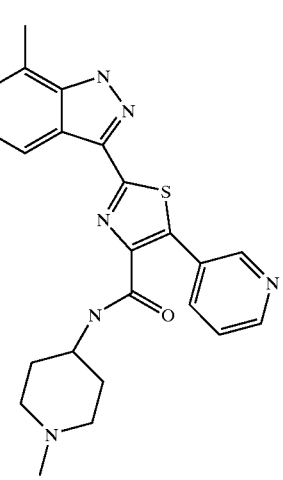 | 2-(5,7-Dimethyl-1H-indazol-3-yl)-5-pyridin-3-yl-thiazole-4-carboxylic acid (1-methyl-piperidin-4-yl)-amide |

TABLE 2-continued

| NO. | STRUCTURE | NAME |
|---|---|---|
| 29. | 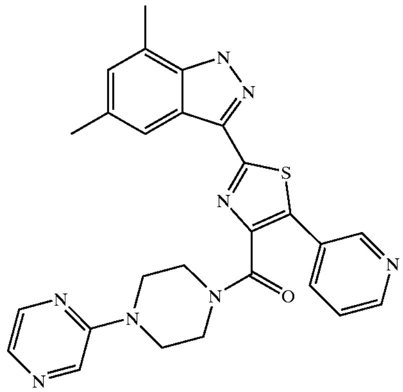 | [2-(5,7-Dimethyl-1H-indazol-3-yl)-5-pyridin-3-yl-thiazol-4-yl]-(2,3,5,6-tetrahydro-[1,2']bipyrazinyl-4-yl)-methanone |
| 30. | 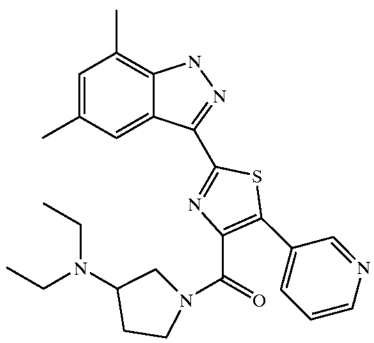 | (3-Diethylamino-pyrrolidin-1-yl)-[2-(5,7-dimethyl-1H-indazol-3-yl)-5-pyridin-3-yl-thiazol-4-yl]-methanone |
| 31. | 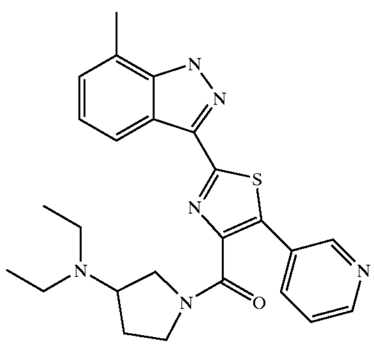 | (3-Diethylamino-pyrrolidin-1-yl)-[2-(7-methyl-1H-indazol-3-yl)-5-pyridin-3-yl-thiazol-4-yl]-methanone |
| 32. | 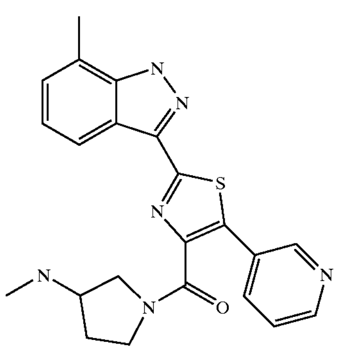 | (3-Methylamino-pyrrolidin-1-yl)-[2-(7-methyl-1H-indazol-3-yl)-5-pyridin-3-yl-thiazol-4-yl]-methanone |

TABLE 2-continued

| NO. | STRUCTURE | NAME |
|---|---|---|
| 33. | 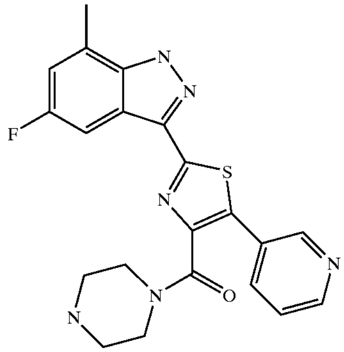 | [2-(5-Fluoro-7-methyl-1H-indazol-3-yl)-5-pyridin-3-yl-thiazol-4-yl]-piperazin-1-yl-methanone |
| 34. | 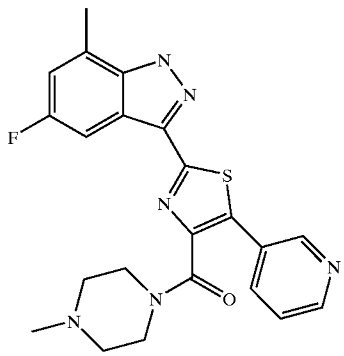 | [2-(5-Fluoro-7-methyl-1H-indazol-3-yl)-5-pyridin-3-yl-thiazol-4-yl]-(4-methyl-piperazin-1-yl)-methanone |
| 35. | Chiral | [2-(5,7-Dimethyl-1H-indazol-3-yl)-5-pyridin-3-yl-thiazol-4-yl]-(2-pyyrrolidin-1-ylmethyl-pyrrolidin-1-yl)-methanone |
| 36. | 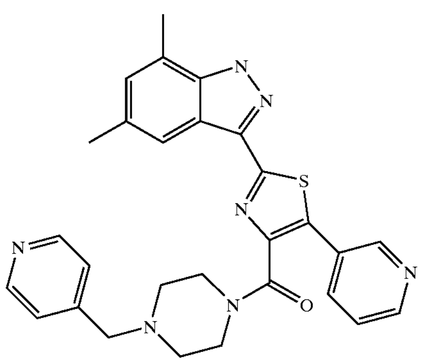 | [2-(5,7-Dimethyl-1H-indazol-3-yl)-5-pyridin-3-yl-thiazol-4-yl]-(4-pyridin-4-ylmethyl-piperazin-1-yl)-methanone |

TABLE 2-continued

| NO. | STRUCTURE | NAME |
| --- | --- | --- |
| 37. | 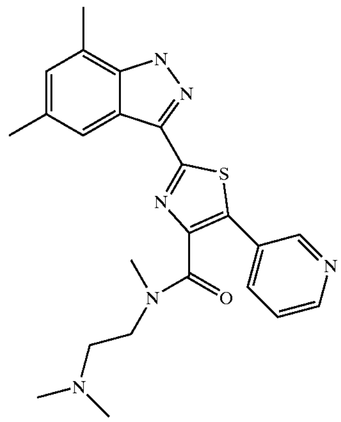 | 2-(5,7-Dimethyl-1H-indazol-3-yl)-5-pyridin-3-yl-thiazole-4-carboxylic acid (2-dimethylamino-ethyl)-methyl-amide |
| 38. | 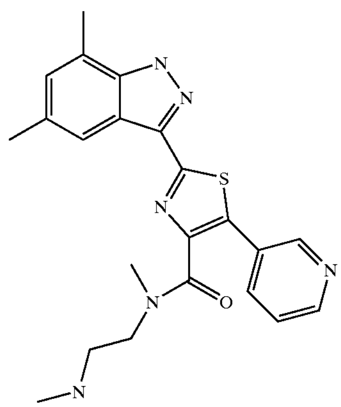 | 2-(5,7-Dimethyl-1H-indazol-3-yl)-5-pyridin-3-yl-thiazole-4-carboxylic acid methyl-(2-methylamino-ethyl)-amide |
| 39. | 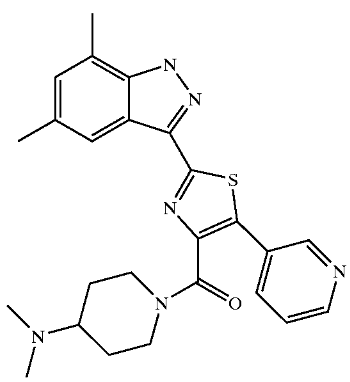 | (4-Dimethylamino-piperidin-1-yl)-[2-(5,7-dimethyl-1H-indazol-3-yl)-5-pyridin-3-yl-thiazol-4-yl]-methanone |
| 40. | 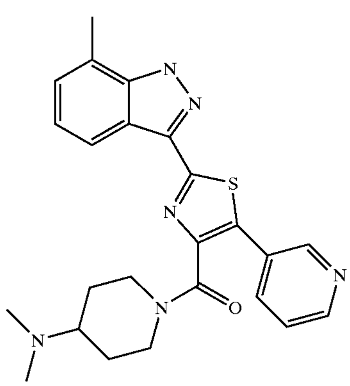 | (4-Dimethylamino-piperidin-1-yl)-[2-(7-methyl-1H-indazol-3-yl)-5-pyridin-3-yl-thiazol-4-yl]-methanone |

TABLE 2-continued

| NO. | STRUCTURE | NAME |
| --- | --- | --- |
| 41. | Chiral | (3-Dimethylamino-pyrrolidin-1-yl)-[2-2-(5-fluoro-7-methyl-1H-indazol-3-yl)-5-pyridin-3-yl-thiazol-4-yl]-methanone |
| 42. | Chiral | (3-Dimethylamino-pyrrolidin-1-yl)-[2-(7-methyl-1H-indazol-3-yl)-5-(6-methyl-pyridin-3-yl)-thiazol-4-yl]-methanone |
| 43. | 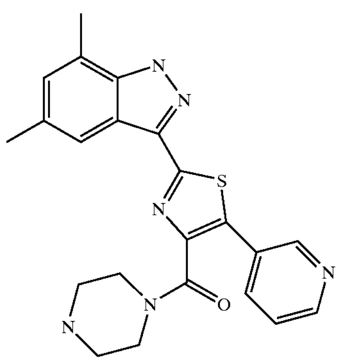 | [2-(5,7-Dimethyl-1H-indazol-3-yl)-5-pyridin-3-yi-thiazol-4-yl]-piperazin-1-yl-methanone |
| 44. | 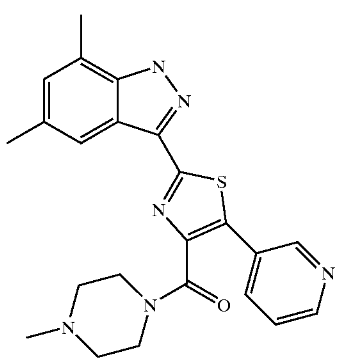 | [2-(5,7-Dimethyl-1H-indazol-3-yl)-5-pyridin-3-yl-thiazol-4-yl]-(4-methyl-piperazin-1-yl)-methanone |

TABLE 2-continued

| NO. | STRUCTURE | NAME |
|---|---|---|
| 45. | 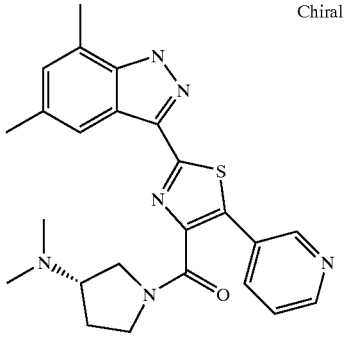 Chiral | (3-Dimethylamino-pyrrolidin-1-yl)-[2-2-(5,7-dimethyl-1H-indazol-3-yl)-5-pyridin-3-yl-thiazol-4-yl]-methanone |
| 46. | 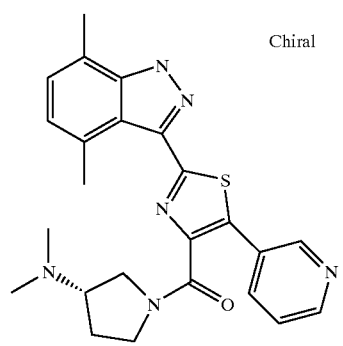 Chiral | (3-Dimethylamino-pyrrolidin-1-yl)-[2-2-(4,7-dimethyl-1H-indazol-3-yl)-5-pyridin-3-yl-thiazol-4-yl]-methanone |
| 47. | 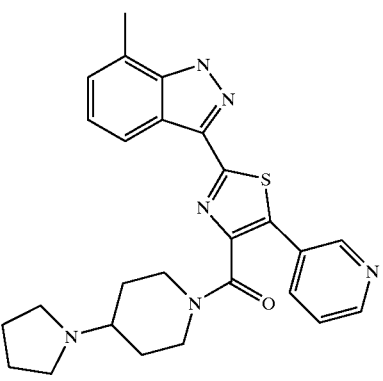 | [2-(7-Methyl-1H-indazol-3-yl)-5-pyridin-3-yl-thiazol-4-yl]-(4-pyrrolidin-1-yl-piperidin-1-yl)-methanone |
| 48. | 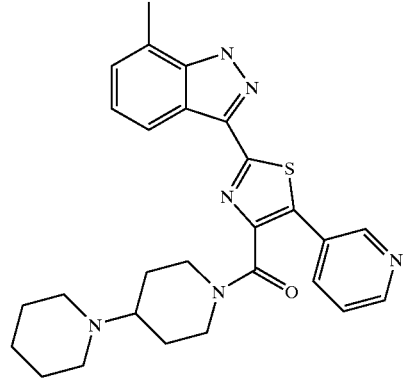 | [1,4']Bipiperidinyl-1'-yl-[2-(7-methyl-1H-indazol-3-yl)-5-pyridin-3-yl-thiazol-4-yl]-methanone |

TABLE 2-continued
| NO. | STRUCTURE | NAME |
| --- | --- | --- |
| 49. | 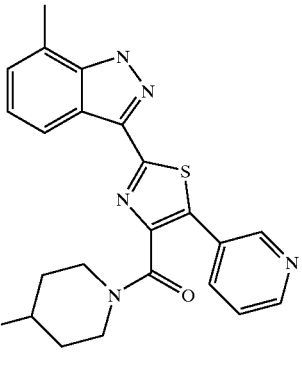 | [2-(7-Methyl-1H-indazol-3-yl)-5-pyridin-3-yl-thiazol-4-yl]-(4-morpholin-4-yl-piperidin-1-yl)-methanone |
| 50. | 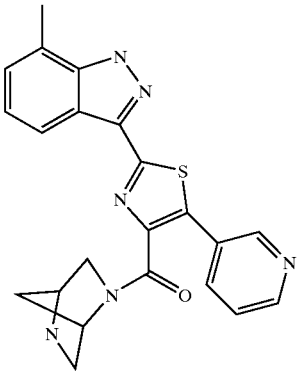 | (2,5-Diaza-bicyclo[2.2.1]hept-2-yl)-[2-(7-methyl-1H-indazol-3-yl)-5-pyridin-3-yl-thiazol-4-yl]-methanone |
| 51. | 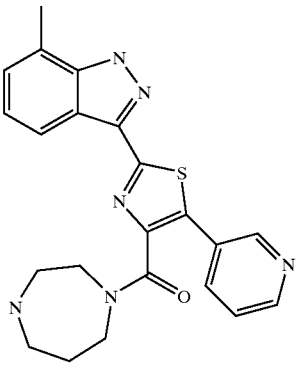 | [1,4]Diazepan-1-yl-[2-(7-methyl-1H-indazol-3-yl)-5-pyridin-3-yl-thiazol-4-yl]-methanone |
| 52. | 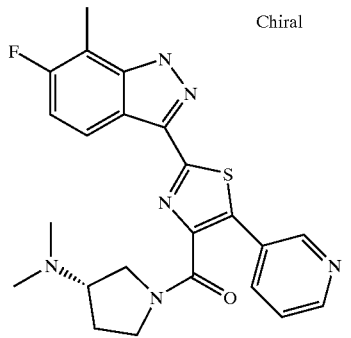 Chiral | (3-Dimethylamino-pyrrolidin-1-yl)-[2-(6-fluoro-7-methyl-1H-indazol-3-yl)-5-pyridin-3-yl-thiazol-4-yl]-methanone |

TABLE 2-continued

| NO. | STRUCTURE | NAME |
|---|---|---|
| 53. | 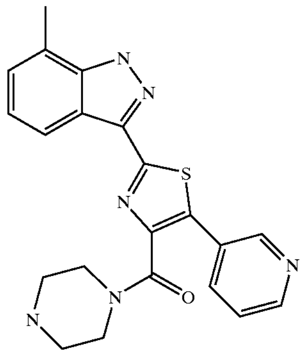 | [2-(7-Methyl-1H-indazol-3-yl)-5-pyridin-3-yl-thiazol-4-yl]-piperazin-1-yl-methanone |
| 54. | 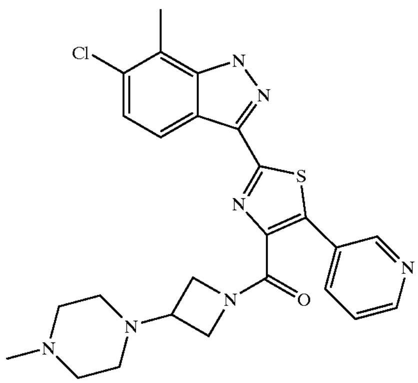 | [2-(6-Chloro-7-methyl-1H-indazol-3-yl)-5-pyridin-3-yl-tiazol-4-yl]-[3-(4-methyl-piperazin-1-yl)-azetidin-1-yl]-methanone |
| 55. | Chiral | (3-Dimethylamino-pyrrolidin-1-yl)-[2-2-(4-fluoro-7-methyl-1H-indazol-3-yl)-5-pyridin-3-yl-thiazol-4-yl]-methanone |
| 56. | 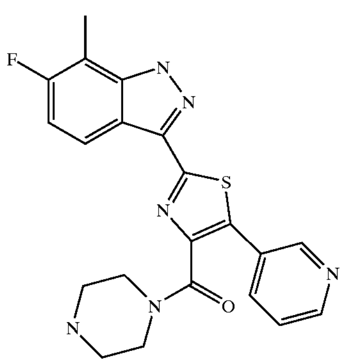 | [2-(6-Fluoro-7-methyl-1H-indazol-3-yl)-5-pyridin-3-yl-thiazol-4-yl]-piperazin-1-yl-methanone |

TABLE 2-continued
| NO. | STRUCTURE | NAME |
|---|---|---|
| 57. | 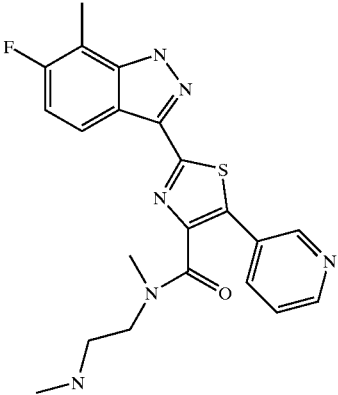 | 2-(6-Fluoro-7-methyl-1H-indazol-3-yl)-5-pyridin-3-yl-thiazole-4-carboxylic acid methyl-(2-methylamino-ethyl)-amide |
| 58. | 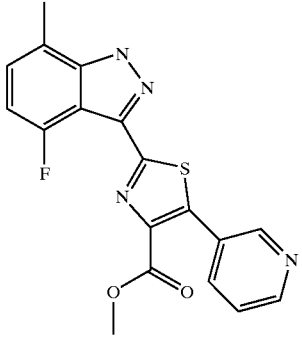 | 2-(4-Fluoro-7-methyl-1H-indazol-3-yl)-5-pyridin-3-yl-thiazole-4-carboxylic acid methyl ester |
| 59. | 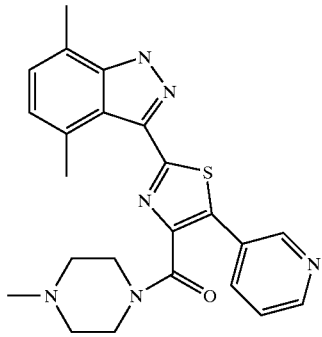 | [2-(4,7-Dimethyl-1H-indazol-3-yl)-5-pyridin-3-yl-thiazol-4-yl]-(4-methyl-piperazin-1-yl)-methanone |
| 60. | 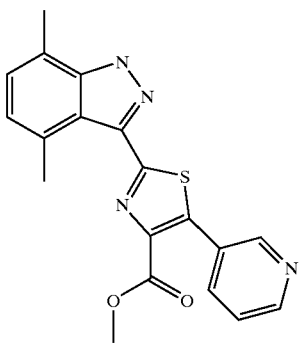 | 2-(4,7-Dimethyl-1H-indazol-3-yl)-5-pyridin-3-yl-thiazole-4-carboxylic acid methyl ester |

TABLE 2-continued

| NO. | STRUCTURE | NAME |
|---|---|---|
| 61. | 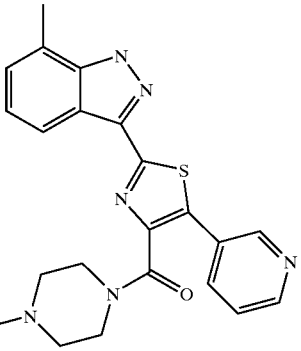 | [2-(7-Methyl-1H-indazol-3-yl)-5-pyridin-3-yl-thiazol-4-yl]-(4-pyridin-4-ylmethyl-piperazin-1-yl)-methanone |
| 62. | 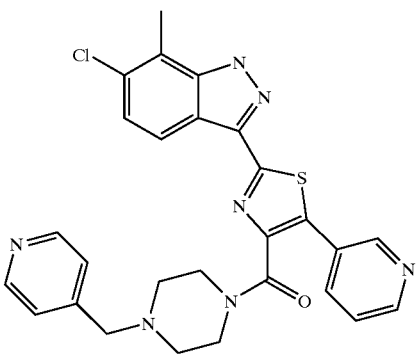 | [2-(6-Chloro-7-methyl-1H-indazol-3-yl)-5-pyridin-3-yl-thiazol-4-yl]-(4-pyridin-4-ylmethyl-piperazin-1-yl)-methanone |
| 63. | 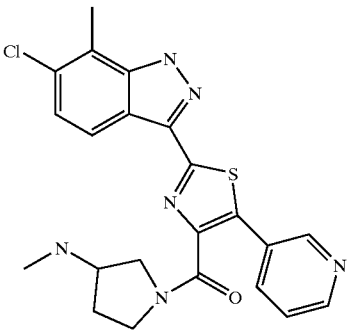 | [2-(6-Chloro-7-methyl-1H-indazol-3-yl)-5-pyridin-3-yl-thiazol-4-yl]-(3-methylamino-pyrrolidin-1-yl)-methanone |
| 64. | 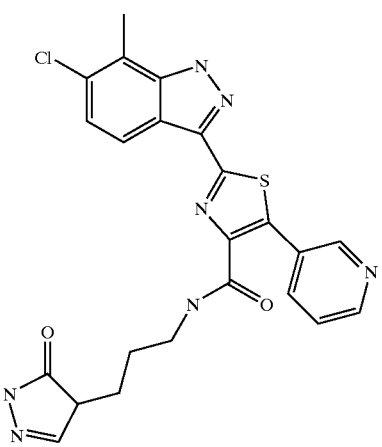 | 2-(6-Chloro-7-methyl-1H-indazol-3-yl)-5-pyridin-3-yl-thiazole-4-carboxylic acid [3-(5-oxo-4,5-dihydro-1H-pyrazol-4-yl)-propyl]-amide |

TABLE 2-continued
| NO. | STRUCTURE | NAME |
|---|---|---|
| 65. | 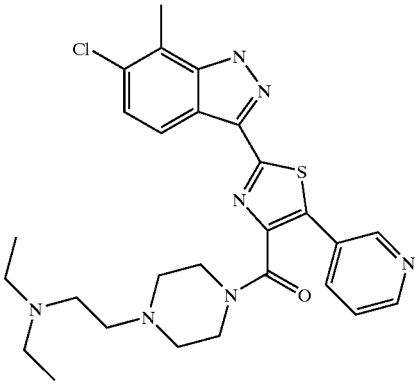 | [2-(6-Chloro-7-methyl-1H-indazol-3-yl)-5-pyridin-3-yl-thiazol-4-yl]-[4-(2-diethylamino-ethyl)-piperazin-1-yl]-methanone |
| 66. | 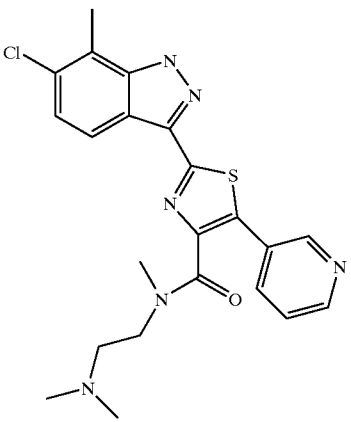 | 2-(6-Chloro-7-methyl-1H-indazol-3-yl)-5-pyridin-3-yl-thiazole-4-carboxylic acid (2-dimethylamino-ethyl)-methyl-amide |
| 67. | 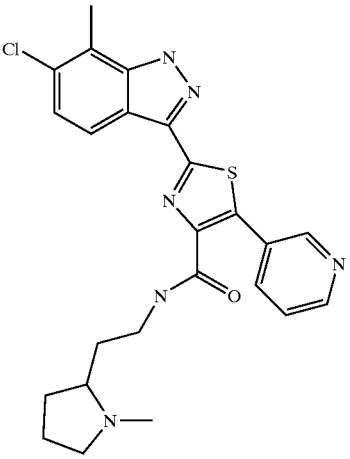 | 2-(6-Chloro-7-methyl-1H-indazol-3-yl)-5-pyridin-3-yl-thiazole-4-carboxylic acid [2-(1-methyl-pyrrolidin-2-yl)-ethyl]-amide |

| NO. | STRUCTURE | NAME |
|---|---|---|
| 68. | 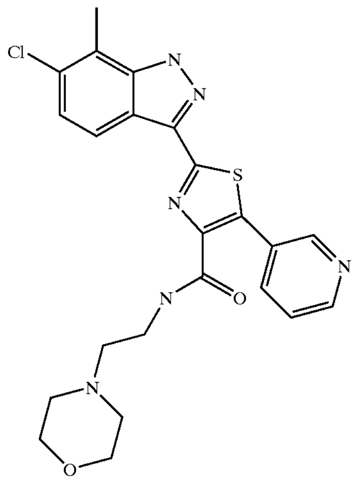 | 2-(6-Chloro-7-methyl-1H-indazol-3-yl)-5-pyridin-3-yl-thiazole-4-carboxylic acid (2-morpholin-4-yl-ethyl)-amide |
| 69. | 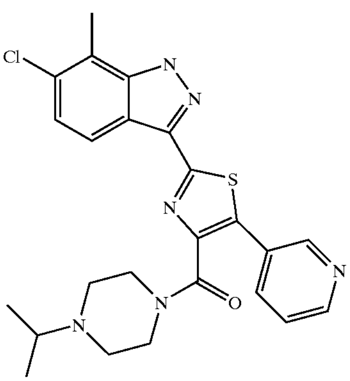 | [2-(6-Chloro-7-methyl-1H-indazol-3-yl)-5-pyridin-3-yl-thiazol-4-yl]-(4-isopropyl-piperazin-1-yl)-methanone |
| 70. | 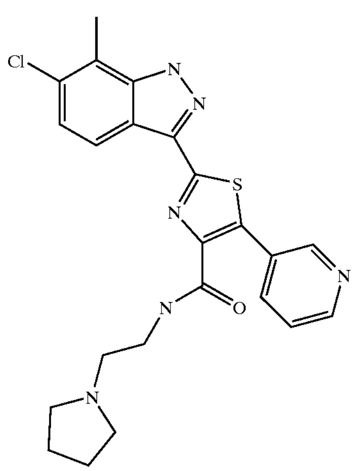 | 2-(6-Chloro-7-methyl-1H-indazol-3-yl)-5-pyridin-3-yl-thiazole-4-carboxylic acid (2-pyrrolidin-1-yl-ethyl)-amide |

TABLE 2-continued

| NO. | STRUCTURE | NAME |
|---|---|---|
| 71. | 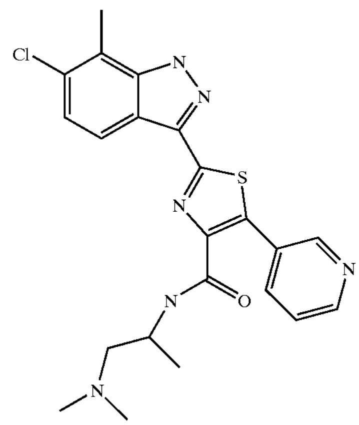 | 2-(6-Chloro-7-methyl-1H-indazol-3-yl)-5-pyridin-3-yl-thiazole-4-carboxylic acid (2-dimethylamino-1-methyl-ethyl)-amide |
| 72. | 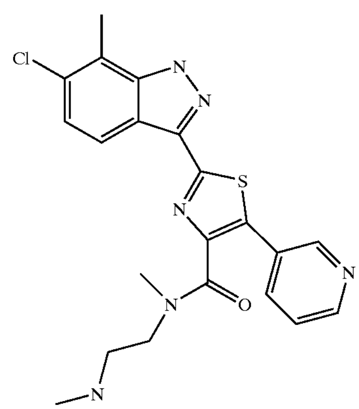 | 2-(6-Chloro-7-methyl-1H-indazol-3-yl)-5-pyridin-3-yl-thiazole-4-carboxylic acid methyl-(2-methylamino-ethyl)-amide |
| 73. | 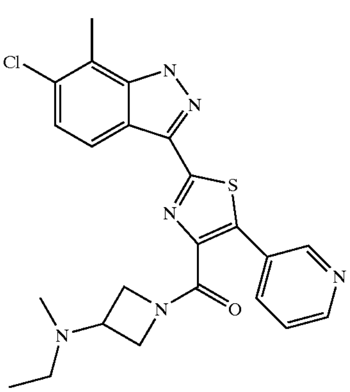 | [2-(6-Chloro-7-methyl-1H-indazol-3-yl)-5-pyridin-3-yl-thiazol-4-yl]-[3-(ethyl-methyl-amino)-azetidin-1-yl]-methanone |

TABLE 2-continued

| NO. | STRUCTURE | NAME |
|---|---|---|
| 74. | 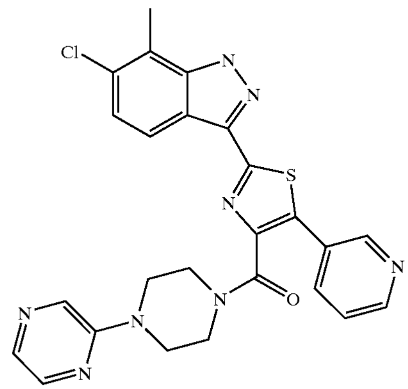 | [2-(6-Chloro-7-methyl-1H-indazol-3-yl)-5-pyridin-3-yl-thiazol-4-yl]-(2,3,5,6-tetrahydro-[1,2']bipyrazinyl-4-yl)-methanone |
| 75. | 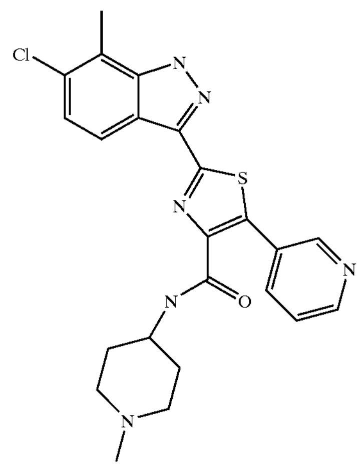 | 2-(6-Chloro-7-methyl-1H-indazol-3-yl)-5-pyridin-3-yl-thiazole-4-carboxylic acid (1-methyl-piperidin-4-yl)-amide |
| 76. | 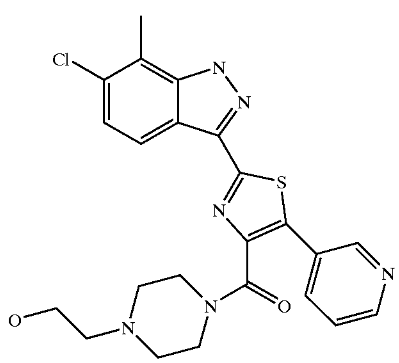 | [2-(6-Chloro-7-methyl-1H-indazol-3-yl)-5-pyridin-3-yl-thiazol-4-yl]-[4-(2-hydroxy-ethyl)-piperazin-1-yl]-methanone |
| 77. | 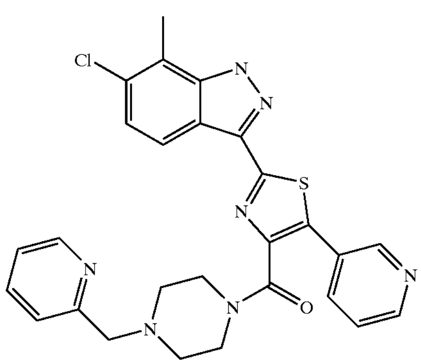 | [2-(6-Chloro-7-methyl-1H-indazol-3-yl)-5-pyridin-3-yl-thiazol-4-yl]-(4-pyridin-2-ylmethyl-piperazin-1-yl)-methanone |

TABLE 2-continued

| NO. | STRUCTURE | NAME |
| --- | --- | --- |
| 78. | 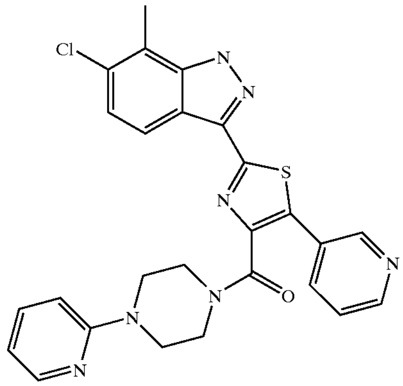 | [2-(6-Chloro-7-methyl-1H-indazol-3-yl)-5-pyridin-3-yl-thiazol-4-yl]-(4-pyridin-2-yl-piperazin-1-yl)-methanone |
| 79. | Chiral | (3-Dimethylamino-pyrrolidin-1-yl)-[2-(7-ethyl-1H-indazol-3-yl)-5-pyridin-3-yl-thiazol-4-yl]-methanone |
| 80. | 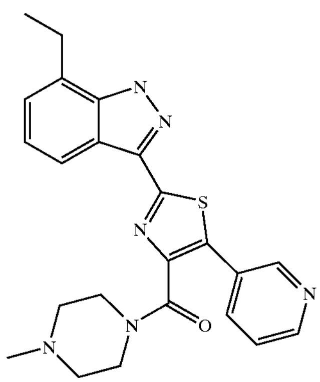 | [2-(7-Ethyl-1H-indazol-3-yl)-5-pyridin-3-yl-thiazol-4-yl]-(4-methyl-piperazin-1-yl)-methanone |
| 81. | Chiral | [2-(6-Chloro-7-methyl-1H-indazol-3-yl)-5-pyridin-3-yl-thiazol-4-yl]-(3-hydroxy-pyrrolidin-1-yl)-methanone |

TABLE 2-continued

| NO. | STRUCTURE | NAME |
| --- | --- | --- |
| 82. | 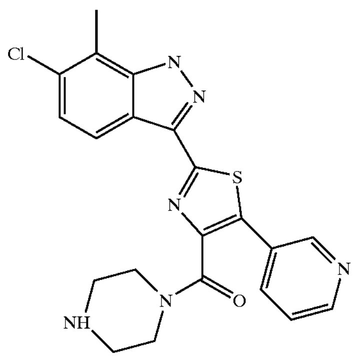 | [2-(6-Chloro-7-methyl-1H-indazol-3-yl)-5-pyridin-3-yl-thiazol-4-yl]-piperazin-1-yl-methanone |
| 83. | 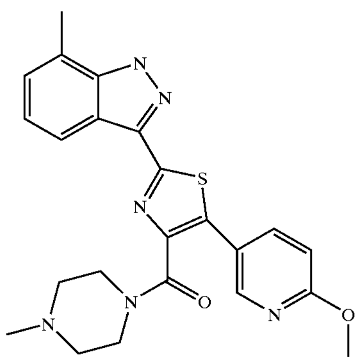 | [5-(6-Methoxy-pyridin-3-yl)-2-(7-methyl-1H-indazol-3-yl)-thiazol-4-yl]-(4-methyl-piperazin-1-yl)-methanone |
| 84. | 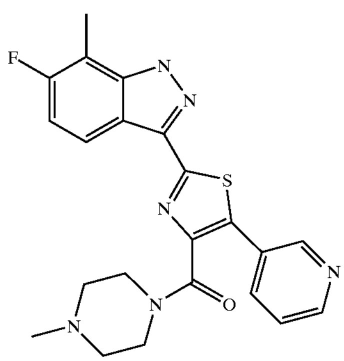 | [2-(6-Fluoro-7-methyl-1H-indazol-3-yl)-5-pyridin-3-yl-thiazol-4-yl]-(4-methyl-piperazin-1-yl)-methanone |
| 85. | 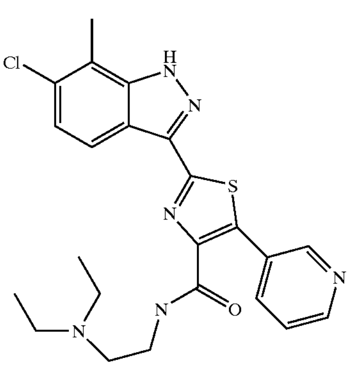 | 2-(6-Chloro-7-methyl-1H-indazol-3-yl)-5-pyridin-3-yl-thiazole-4-carboxylic acid (2-diethylamino-ethyl)-amide |

TABLE 2-continued

| NO. | STRUCTURE | NAME |
|---|---|---|
| 86. | 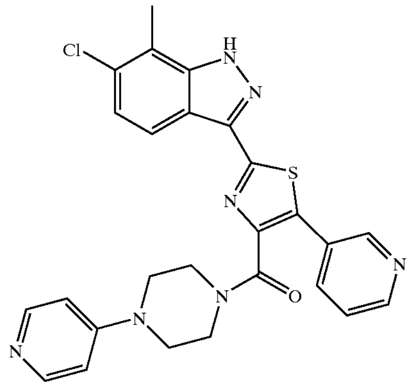 | [2-(6-Chloro-7-methyl-1H-indazol-3-yl)-5-pyridin-3-yl-thiazol-4-yl]-(4-pyridin-4-yl-piperazin-1-yl)-methanone |
| 87. | 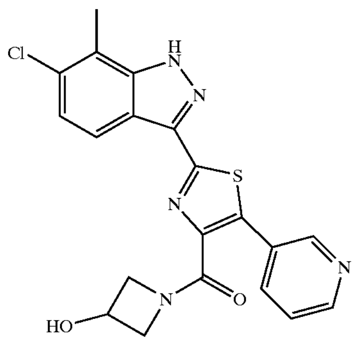 | [2-(6-Chloro-7-methyl-1H-indazol-3-yl)-5-pyridin-3-yl-thiazol-4-yl]-(3-hydroxy-azetidin-1-yl)-methanone |
| 88. | 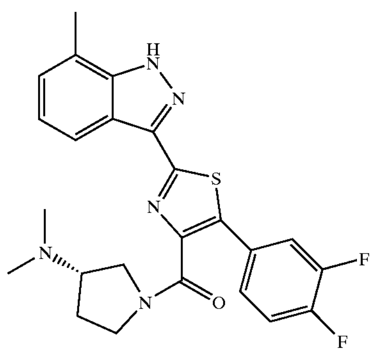 | [5-(3,4-Difluoro-phenyl)-2-(7-methyl-1H-indazol-3-yl)-thiazol-4-yl]-(3-dimethylamino-pyrrolidin-1-yl)-methanone |
| 89. | 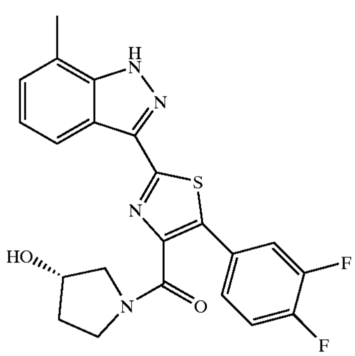 | [5-(3,4-Difluoro-phenyl)-2-(7-methyl-1H-indazol-3-yl)-thiazol-4-yl]-(3-hydroxy-pyrrolidin-1-yl)-methanone |

TABLE 2-continued
| NO. | STRUCTURE | NAME |
|---|---|---|
| 90. | 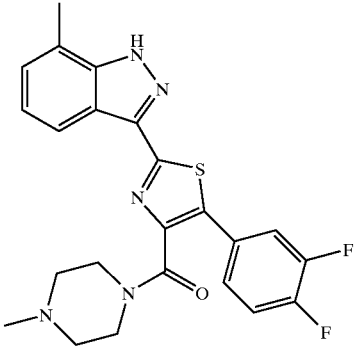 | [5-(3,4-Difluoro-phenyl)-2-(7-methyl-1H-indazol-3-yl)-thiazol-4-yl]-(4-methyl-piperazin-1-yl)-methanone |
| 91. | 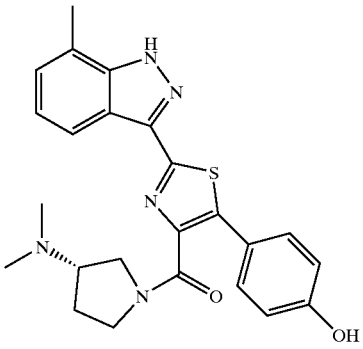 | (3-Dimethylamino-pyrrolidin-1-yl)-[5-(4-hydroxy-phenyl)-2-(7-methyl-1H-indazol-3-yl)-thiazol-4-yl]-methanone |
| 92. | 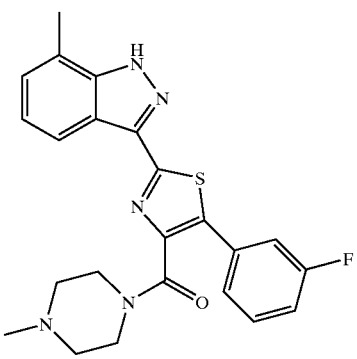 | [5-(3-Fluoro-phenyl)-2-(7-methyl-1H-indazol-3-yl)-thiazol-4-yl]-(4-methyl-piperazin-1-yl)-methanone |
| 93. | 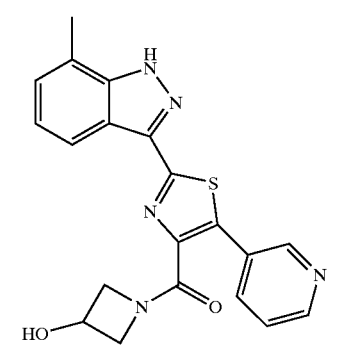 | (3-Hydroxy-azetidin-1-yl)-[2-(7-methyl-1H-indazol-3-yl)-5-pyridin-3-yl-thiazol-4-yl]-methanone |

TABLE 2-continued

| NO. | STRUCTURE | NAME |
| --- | --- | --- |
| 94. | 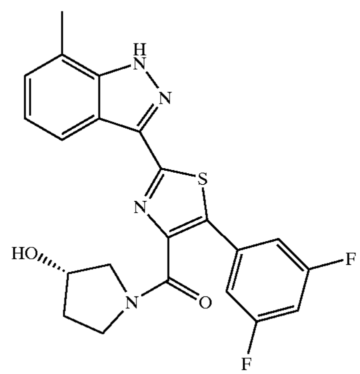 | [5-(3,5-Difluoro-phenyl)-2-(7-methyl-1H-indazol-3-yl)-thiazol-4-yl]-(3-hydroxy-pyrrolidin-1-yl)-methanone |
| 95. | 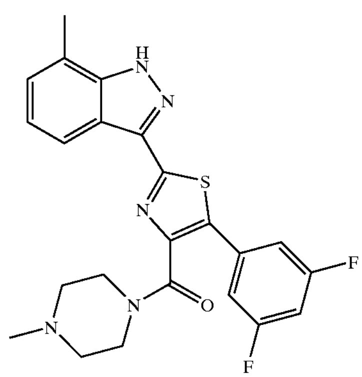 | [5-(3,5-Difluoro-phenyl)-2-(7-methyl-1H-indazol-3-yl)-thiazol-4-yl]-(4-methyl-piperazin-1-yl)-methanone |
| 96. | 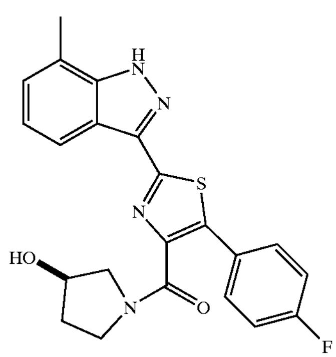 | [5-(4-Fluoro-phenyl)-2-(7-methyl-1H-indazol-3-yl)-thiazol-4-yl]-(3-hydroxy-pyrrolidin-1-yl)-methanone |
| 97. | 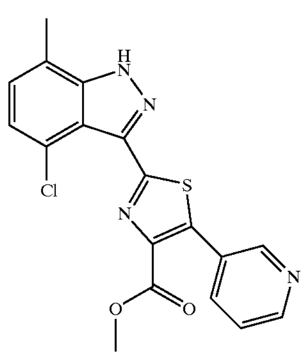 | 2-(4-Chloro-7-methyl-1H-indazol-3-yl)-5-pyridin-3-yl-thiazole-4-carboxylic acid methyl ester |

TABLE 2-continued

| NO. | STRUCTURE | NAME |
|---|---|---|
| 98. | 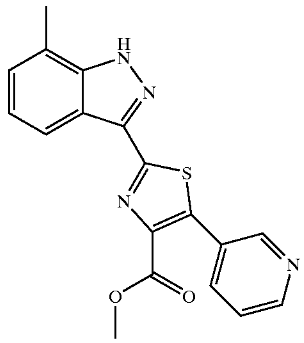 | 5-(4-Hydroxy-phenyl)-2-(7-methyl-1H-indazol-3-yl)-thiazole-4-carboxylic acid methyl ester |
| 99. | 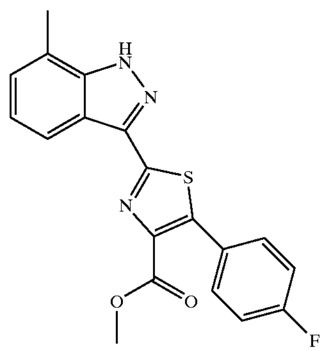 | 5-(4-Fluoro-phenyl)-2-(7-methyl-1H-indazol-3-yl)-thiazole-4-carboxylic acid methyl ester |
| 100. | 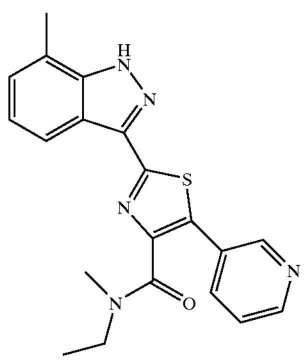 | 2-(7-Methyl-1H-indazol-3-yl)-5-pyridin-3-yl-thiazole-4-carboxylic acid ethyl-methyl-amide |
| 101. | 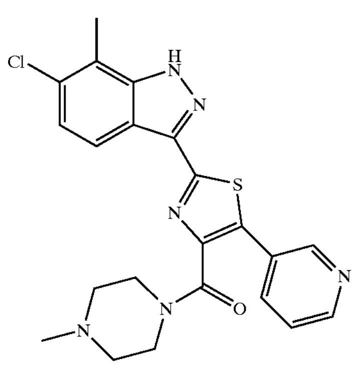 | [2-(6-Chloro-7-methyl-1H-indazol-3-yl)-5-pyridin-3-yl-thiazol-4-yl]-(4-methyl-piperazin-1-yl)-methanone |

TABLE 2-continued
| NO. | STRUCTURE | NAME |
|---|---|---|
| 102. | 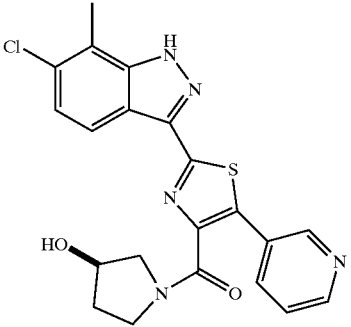 | [2-(6-Chloro-7-methyl-1H-indazol-3-yl)-5-pyridin-3-yl-thiazol-4-yl]-(3-hydroxy-pyrrolidin-1-yl)-methanone |
| 103. | 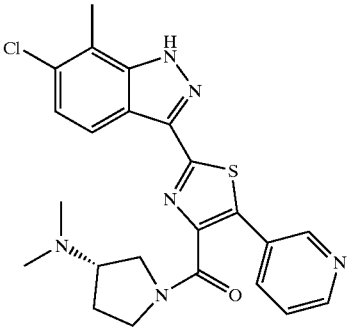 | [2-(6-Chloro-7-methyl-1H-indazol-3-yl)-5-pyridin-3-yl-thiazol-4-yl]-(3-dimethylamino-pyrrolidin-1-yl)-methanone |
| 104. | 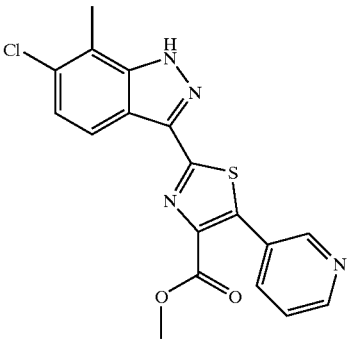 | 2-(6-Chloro-7-methyl-1H-indazol-3-yl)-5-pyridin-3-yl-thiazole-4-carboxylic acid methyl ester |
| 105. | 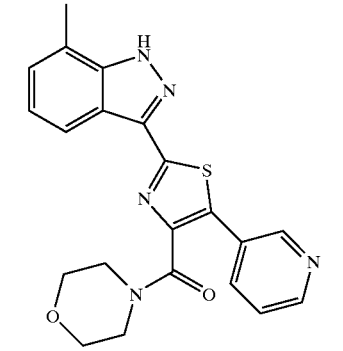 | [2-(7-Methyl-1H-indazol-3-yl)-5-pyridin-3-yl-thiazol-4-yl]-morpholin-4-yl-methanone |

TABLE 2-continued

| NO. | STRUCTURE | NAME |
|---|---|---|
| 106. | 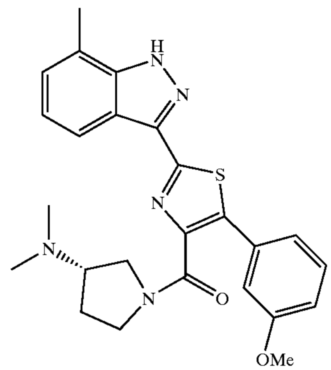 | (3-Dimethylamino-pyrrolidin-1-yl)-[5-5-(3-methoxy-phenyl)-2-(7-methyl-1H-indazol-3-yl)-thiazol-4-yl]-methanone |
| 107. | 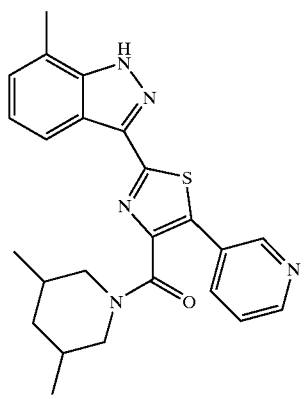 | (3,5-Dimethyl-piperidin-1-yl)-[2-(7-methyl-1H-indazol-3-yl)-5-pyridin-3-yl-thiazol-4-yl]-methanone |
| 108. | 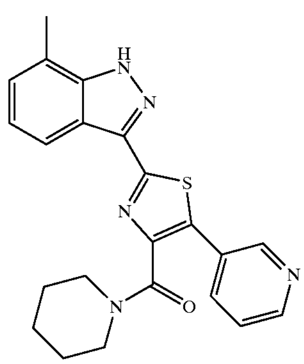 | [2-(7-Methyl-1H-indazol-3-yl)-5-pyridin-3-yl-thiazol-4-yl]-piperidin-1-yl-methanone |
| 109. | 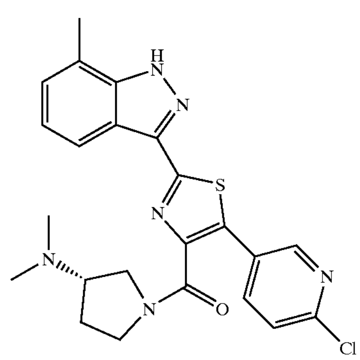 | [5-(6-Chloro-pyridin-3-yl)-2-(7-methyl-1H-indazol-3-yl)-thiazol-4-yl]-(3-dimethylamino-pyrrolidin-1-yl)-methanone |

TABLE 2-continued

| NO. | STRUCTURE | NAME |
|---|---|---|
| 110. | 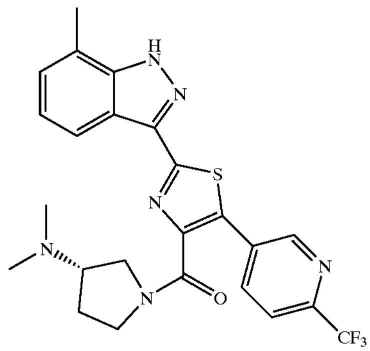 | (3-Dimethylamino-pyrrolidin-1-yl)-[2-2-(7-methyl-1H-indazol-3-yl)-5-(6-trifluoromethyl-pyridin-3-yl)-thiazol-4-yl]-methanone |
| 111. | 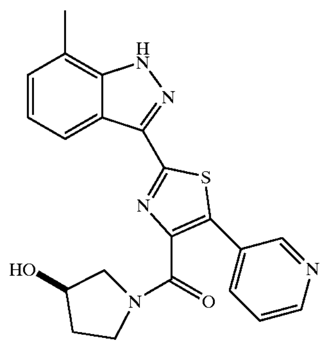 | (3-Hydroxy-pyrrolidin-1-yl)-[2-(7-methyl-1H-indazol-3-yl)-5-pyridin-3-yl-thiazol-4-yl]-methanone |
| 112. | 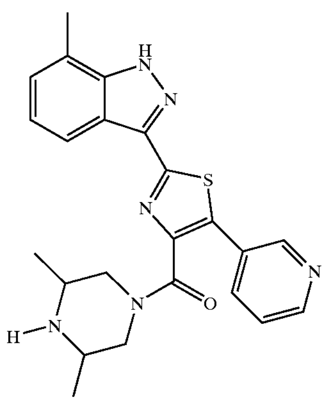 | (3,5-Dimethyl-piperazin-1-yl)-[2-(7-methyl-1H-indazol-3-yl)-5-pyridin-3-yl-thiazol-4-yl]-methanone |
| 113. | 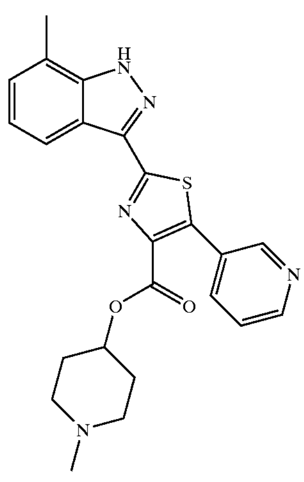 | 2-(7-Methyl-1H-indazol-3-yl)-5-pyridin-3-yl-thiazole-4-carboxylic acid 1-methyl-pipendin-4-yl ester |

TABLE 2-continued

| NO. | STRUCTURE | NAME |
|---|---|---|
| 114. | 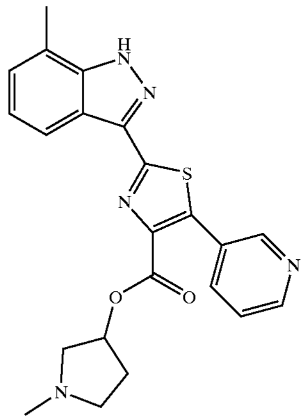 | 2-(7-Methyl-1H-indazol-3-yl)-5-pyridin-3-yl-thiazole-4-carboxylic acid 1-methyl-pyrrolidin-3-yl ester |
| 115. | 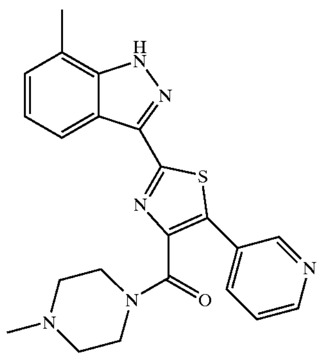 | [2-(7-Methyl-1H-indazol-3-yl)-5-pyridin-3-yl-thiazol-4-yl]-(4-methyl-piperazin-1-yl)-methanone |
| 116. | 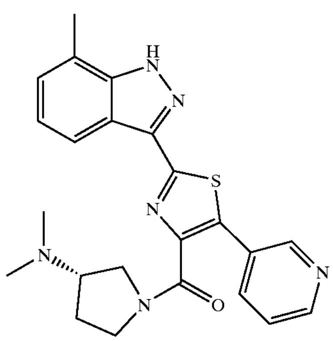 | (3-Dimethylamino-pyrrolidin-1-yl)-[2-(7-methyl-1H-indazol-3-yl)-5-pyridin-3-yl-thiazol-4-yl]-methanone |
| 117. | 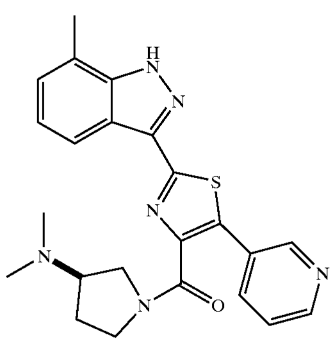 | (3-Dimethylamino-pyrrolidin-1-yl)-[2-(7-methyl-1H-indazol-3-yl)-5-pyridin-3-yl-thiazol-4-yl]-methanone |

TABLE 2-continued

| NO. | STRUCTURE | NAME |
|---|---|---|
| 118. | 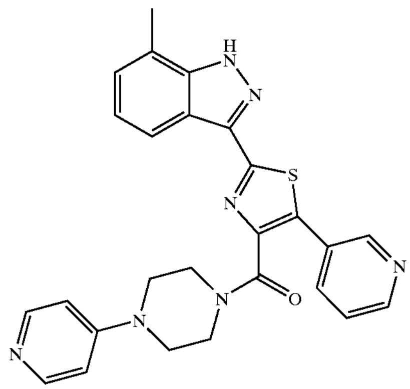 | [2-(7-Methyl-1H-indazol-3-yl)-5-pyridin-3-yl-thiazol-4-yl]-(4-pyridin-4-yl-piperazin-1-yl)-methanone |
| 119. | 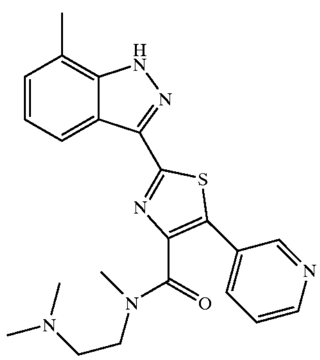 | 2-(7-Methyl-1H-indazol-3-yl)-5-pyridin-3-yl-thiazole-4-carboxylic acid (2-dimethylamino-ethyl)-methyl-amide |
| 120. | 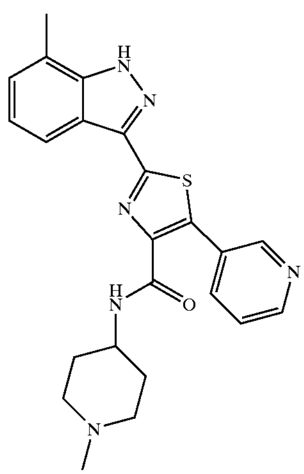 | 2-(7-Methyl-1H-indazol-3-yl)-5-pyridin-3-yl-thiazole-4-carboxylic acid (1-methyl-piperidin-4-yl)-amide |
| 121. | 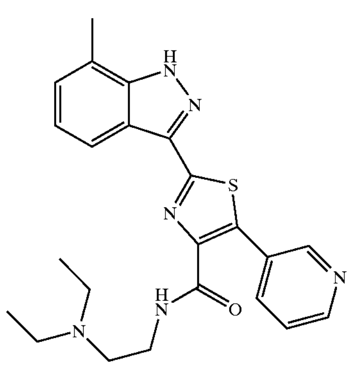 | 2-(7-Methyl-1H-indazol-3-yl)-5-pyridin-3-yl-thiazole-4-carboxylic acid (2-diethylamino-ethyl)-amide |

TABLE 2-continued
| NO. | STRUCTURE | NAME |
|---|---|---|
| 122. | 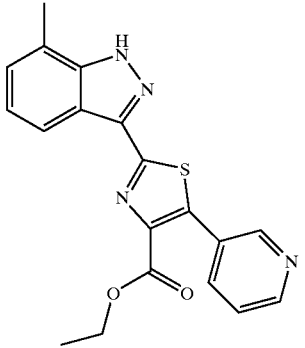 | 2-(7-Methyl-1H-indazol-3-yl)-5-pyridin-3-yl-thiazole-4-carboxylic acid ethyl ester |
| 123. | 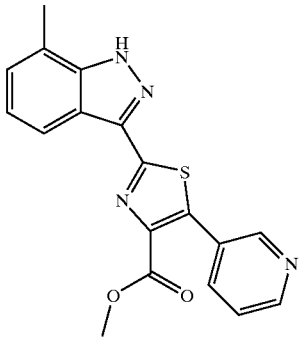 | 2-(7-Methyl-1H-indazol-3-yl)-5-pyridin-3-yl-thiazole-4-carboxylic acid methyl ester |
| 124. | 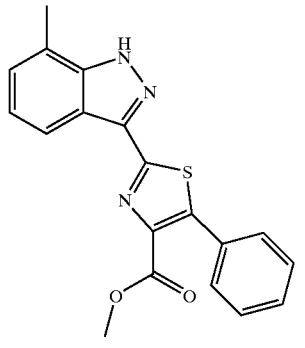 | 2-(7-Methyl-1H-indazol-3-yl)-5-phenyl-thiazole-4-carboxylic acid methyl ester |
| 125. | 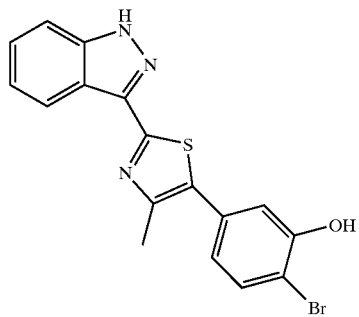 | 2-Bromo-5-[2-(1H-indazol-3-yl)-4-methyl-thiazol-5-yl]-phenol |

TABLE 2-continued

| NO. | STRUCTURE | NAME |
|---|---|---|
| 126. | 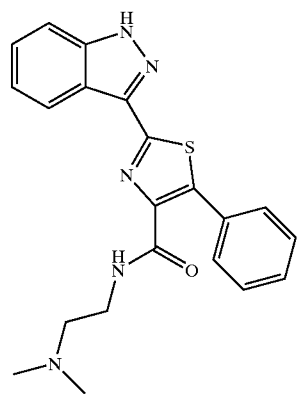 | 2-(1H-Indazol-3-yl)-5-phenyl-thiazole-4-carboxylic acid (2-dimethylamino-ethyl)-amide |
| 127. | 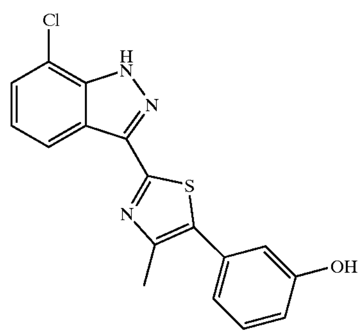 | 3-[2-(7-Chloro-1H-indazol-3-yl)-4-methyl-thiazol-5-yl]-phenol |
| 128. | 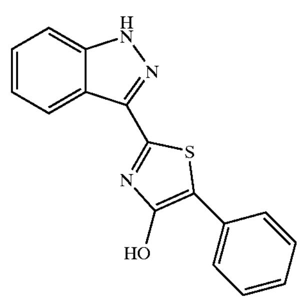 | 2-(1H-Indazol-3-yl)-5-phenyl-thiazol-4-ol |
| 129. | 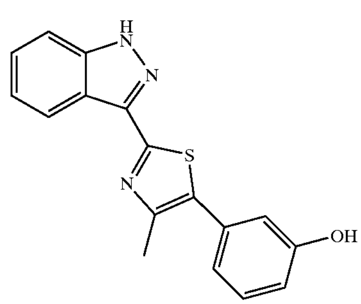 | 3-[2-(1H-Indazol-3-yl)-4-methyl-thiazol-5-yl]-phenol |

TABLE 2-continued

| NO. | STRUCTURE | NAME |
|---|---|---|
| 130. | 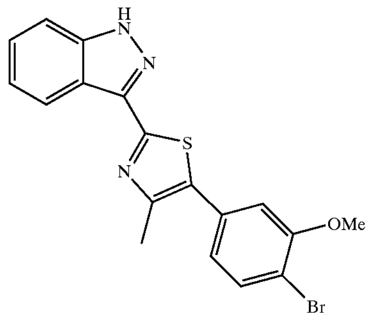 | 3-[5-(4-Bromo-3-methoxy-phenyl)-4-methyl-thiazol-2-yl]-1H-indazole |

What is claimed is:

1. A compound comprising an indazolyl group and a thiazolyl group, the compound being represented by the structure

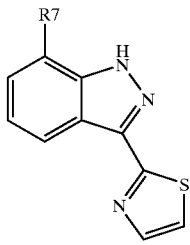

wherein R7 is selected from the group consisting of $C_{1-C6}$ hydrocarbon, lower alkoxy, lower thioalkoxy, CN, $NO_2$, halogen, $CF_3$, and $OCF_3$; and
wherein the $C_{1-C6}$ hydrocarbon, indazolyl group, and thiazolyl group are optionally substituted on carbon;
or a pharmaceutically acceptable salt, ester, solvate or prodrug thereof.

2. The compound of claim 1, wherein R7 is selected from the group consisting of methyl, ethyl, propyl, allyl, F, Cl, and Br.

3. The compound of claim 2, wherein the propyl is cyclopropyl.

4. The compound of claim 2, wherein R7 is selected from the group consisting of methyl, ethyl, F, and Cl.

5. The compound of claim 4, wherein R7 is methyl.

6. The compound of claim 1, wherein the indazolyl group bears at least one substituent selected from the group consisting of optionally substituted $C_1$–$C_6$ hydrocarbon, optionally substituted heterocycle, lower alkoxy, CN, $NO_2$, F, Cl, Br, $CF_3$, and $OCF_3$.

7. The compound of claim 6, wherein the indazolyl bears at least one substituent selected from the group consisting of optionally substituted $C_1$–$C_6$ hydrocarbon, F, and Cl.

8. The compound of claim 7, wherein the indazolyl group bears at least one substituent selected from the group consisting of methyl, ethyl, propyl, allyl, methylcyclopropyl, F, and Cl.

9. The compound of claim 8, wherein the indazolyl group bears at least one substituent selected from the group consisting of methyl, ethyl, F, and Cl.

10. The compound of claim 1, wherein the thiazolyl group bears at least one substituent selected from the group consisting of optionally substituted $C_1$–$C_{10}$ hydrocarbon, optionally substituted $C_1$–$C_{10}$ heterocycle, optionally substituted carboxamido, optionally substituted aminocarboxy, optionally substituted $C_1$–$C_6$ alkoxy, optionally substituted $C_1$–$C_6$ alkoxycarbonyl, OH, and COOH.

11. The compound of claim 10, wherein the thiazolyl group bears at least one substituent selected from the group consisting of methyl, ethyl, OH, COOH, $COOCH_3$, and $COOCH_2CH_3$.

12. The compound of claim 10, wherein the thiazolyl group bears at least one substituent selected from the group consisting of optionally substituted $C_1$–$C_{10}$ hydrocarbon, optionally substituted $C_1$–$C_6$ alkoxycarbonyl, COOH, OH, $COOR^3$, and $CONR^8R^9$,
wherein $R^3$ is selected from the group consisting of optionally substituted heterocycle and $C_1$–$C_6$ alkyl substituted by heterocycle;
wherein $R^8$ and $R^9$ are independently selected from the group consisting of H, optionally substituted heterocycle, and optionally substituted $C_1$–$C_6$ hydrocarbon or;
wherein $R^8$ and $R^9$ may together form a four-, five-, or six-membered optionally substituted heterocyclic ring including the N atom to which $R^8$ and $R^9$ are attached; and
wherein for said ring one to three carbon atoms may optionally each independently be replaced by an atom selected from the group consisting of N, O, and S.

13. The compound of claim 10, wherein the thiazolyl group bears two substituents, each of which is independently selected from the group consisting of optionally substituted $C_1$–$C_{10}$ hydrocarbon, COOH, optionally substituted $C_1$–$C_6$ alkoxycarbonyl, OH, $COOR^3$, and $CONR^8R^9$,
wherein $R^3$ is selected from the group consisting of optionally substituted heterocycle and $C_1$–$C_6$ alkyl substituted by heterocycle;
wherein $R^8$ and $R^9$ are independently selected from the group consisting of H, optionally substituted heterocycle, and optionally substituted $C_1$–$C_6$ hydrocarbon, or,
wherein $R^8$ and $R^9$ may together form a four-, five-, or six-membered optionally substituted heterocyclic ring including the N atom to which R and R' are attached; and
wherein for said ring one to three carbon atoms may optionally each independently be replaced by an atom selected from the group consisting of N, O, and S.

14. The compound of claim 12, wherein the substituent is selected from the group consisting of methyl, ethyl, OH, phenyl, COOH, $COOCH_3$, and $COOCH_2CH_3$.

15. The compound of claim 12, wherein the thiazolyl group is attached to a carbonyl carbon of at least one substituent represented by a structure selected from the group consisting of

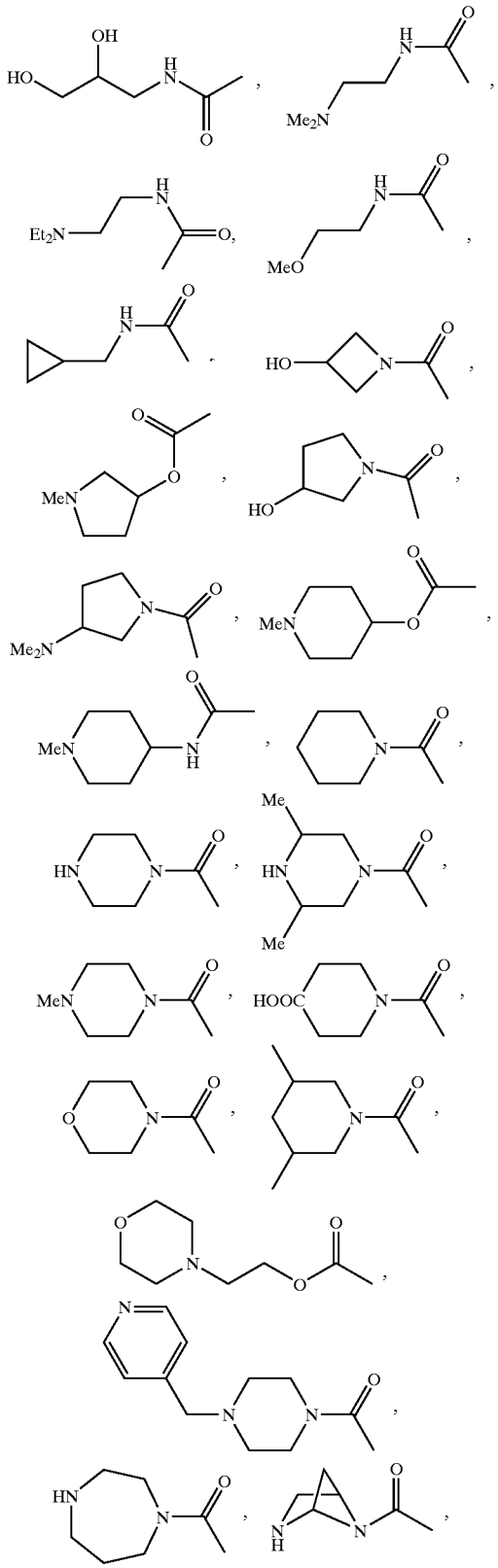

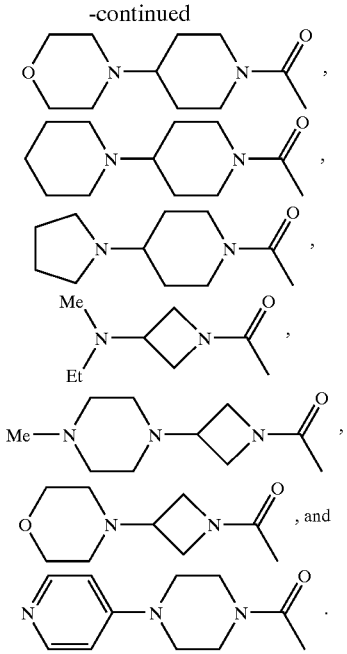

16. The compound of claim 10, wherein the substituent is selected from the group consisting of phenyl and pyridyl,
wherein the phenyl is optionally substituted with at least one substituent selected from the group consisting of OH, $OCH_3$, F, Cl, Br, optionally substituted piperazin-1-yl, and optionally substituted morpholin-4-yl; and
wherein the pyridyl is optionally substituted with at least one substituent selected from the group consisting of $C_1$–$C_6$ alkyl, F, Cl, Br, I, $CF_3$, 3,5-dimethyl-piperazin-1-yl, and morpholin-4-yl.

17. The compound of claim 16, wherein the optionally substituted phenyl is selected from the group consisting of 3-hydroxyphenyl, 4-hydroxyphenyl, 3-methoxyphenyl, 3-fluorophenyl, 4-fluorophenyl, 4-fluoro-3-hydroxy-phenyl, 3,4-difluoro-phenyl, 3,5-difluoro-phenyl, 4-bromo-3-methoxy-phenyl, 4-(4-methyl-piperazin-1-yl)-phenyl, and 4-(morpholin-4-yl)-phenyl.

18. The compound of claim 16, wherein the pyridyl is selected from the group consisting of pyridin-3-yl, 6-methyl-pyridin-3-yl, 6-chloro-pyridin-3-yl, and 6-trifluoromethyl-pyridin-3-yl.

19. The compound of claim 1, wherein the compound is (3-dimethylamino-pyrrolidin-1-yl)-[2-(7-methyl-1H-indazol-3-yl)-5-pyridin-3-yl-thiazol-4-yl]-methanone.

20. The compound of claim 1, wherein the compound is (3-(S)-dimethylamino-pyrrolidin-1-yl)-[2-(7-methyl-1H-indazol-3-yl)-5-pyridin-3-yl-thiazol-4-yl]-methanone.

21. The compound of claim 1, wherein the compound is (3-dimethylamino-pyrrolidin-1-yl)-[2-(6-fluoro-7-methyl-1H-indazol-3-yl)-5-pyridin-3-yl-thiazol-4-yl]-methanone.

22. The compound of claim 1, wherein the compound is (3-(S)-dimethylamino-pyrrolidin-1-yl)-[2-(6-fluoro-7-methyl-1H-indazol-3-yl)-5-pyridin-3-yl-thiazol-4-yl]-methanone.

23. The compound of claim 1, wherein the compound is a (3-dimethylamino-pyrrolidin-1-yl)-[2-(6-fluoro-7-methyl-1H-indazol-3-yl)-5-pyridin-3-yl-thiazol-4-yl]-methanone in which the pyridyl is methyl substituted.

24. The compound of claim 1, wherein the compound is (3-dimethylamino-pyrrolidin-1-yl)-[2-(7-methyl-1H-indazol-3-yl)-5-(6-methyl-pyridin-3-yl)-thiazol-4-yl]-methanone.

25. The compound of claim 1, wherein the compound is (3-(S)-dimethylamino-pyrrolidin-1-yl)-[2-(7-methyl-1H-indazol-3-yl)-5-(6-methyl-pyridin-3-yl)-thiazol-4-methanone.

26. The compound of claim 1, wherein the compound is (3-dimethylamino-pyrrolidin-1-yl)-[2-(6-fluoro-7-methyl-1H-indazol-3-yl)-5-(6-methyl-pyridin-3-yl)-thiazol-4-yl]-methanone.

27. The compound of claim 1, wherein the compound is (3-(S)-dimethylamino-pyrrolidin-1-yl)-[2-(6-fluoro-7-methyl-1H-indazol-3-yl)-5-(6-methyl-pyridin-3-yl)-thiazol-4-yl]-methanone.

28. The compound of claim 1, wherein the compound is [2-(5,7-dimethyl-1H-indazol-3-yl)-5-pyridin-3-yl-thiazol-4-yl]-(4-methyl-piperazin-1-yl)-methanone.

29. The compound of claim 1, wherein the compound is 1-[2-(5,7-dimethyl-1H-indazol-3-yl)-5-pyridin-3-yl-thiazol-4-yl]-2-(1-methyl-piperidin-4-yl)-ethanone.

30. The compound of claim 1, wherein the compound is [2-(5,7-dimethyl-1H-indazol-3-yl)-5-pyridin-3-yl-thiazol-4-yl]-[3-(4-methyl-piperazin-1-yl)-azetidin-1-yl]-methanone.

31. The compound of claim 1, wherein the compound is [2-(5,7-dimethyl-1H-indazol-3-yl)-5-pyridin-3-yl-thiazol-4-yl]-(3-morpholin-4-yl-azetidin-1-yl)-methanone.

32. The compound of claim 1, wherein the compound is [2-(5,7-dimethyl-1H-indazol-3-yl)-5-pyridin-3-yl-thiazol-4-yl]-[3-(ethyl-methyl-amino)-azetidin-yl]-methanone.

33. The compound of claim 1 that is synthetically produced.

34. The isolated, purified compound of claim 1.

35. A composition comprising the compound of claim 1 and a pharmaceutically acceptable carrier.

* * * * *